US012708772B2

(12) United States Patent
Lu

(10) Patent No.: US 12,708,772 B2
(45) Date of Patent: Aug. 18, 2026

(54) ACCESSING SPINAL NETWORK TO ENABLE RESPIRATORY FUNCTION

(71) Applicant: The Regents of the University of California, Oakland, CA (US)

(72) Inventor: Daniel C. Lu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/740,323

(22) PCT Filed: Jul. 11, 2016

(86) PCT No.: PCT/US2016/041802
§ 371 (c)(1),
(2) Date: Dec. 27, 2017

(87) PCT Pub. No.: WO2017/011410
PCT Pub. Date: Jan. 19, 2017

(65) Prior Publication Data
US 2018/0185642 A1 Jul. 5, 2018

Related U.S. Application Data

(60) Provisional application No. 62/191,892, filed on Jul. 13, 2015.

(51) Int. Cl.
*A61N 1/36* (2006.01)
*A61N 1/05* (2006.01)
(Continued)

(52) U.S. Cl.
CPC .............. *A61N 1/3611* (2013.01); *A61N 1/05* (2013.01); *A61N 1/0551* (2013.01);
(Continued)

(58) Field of Classification Search
CPC .......... A61N 1/3611; A61N 1/36; A61N 1/05; A61N 1/36175; A61N 1/0551; A61N 2/02;
(Continued)

(56) References Cited

U.S. PATENT DOCUMENTS 2,868,343 A 1/1959 Sproul
3,543,761 A 12/1970 Bradley
(Continued)

FOREIGN PATENT DOCUMENTS

AU 2012204526 A1 7/2013
CA 2649663 A1 11/2007
(Continued)

OTHER PUBLICATIONS

Vital Signs—Cleveland Clinic—Nov. 22, 2021—https://my.clevelandclinic.org/health/articles/10881-vital-signs.*
(Continued)

*Primary Examiner* — Rex R Holmes
(74) *Attorney, Agent, or Firm* — Quarles & Brady LLP

(57) ABSTRACT

In various embodiments, methods are provided for improving, and/or regulating, and/or restoring respiration in a subject with a respiratory deficiency. In certain embodiments the methods involve neuromodulating the cervical spinal cord of a subject by administering transcutaneous stimulation to the cervical spinal cord or a region thereof at a frequency and intensity sufficient to regulate and/or to restore respiration; and/or neuromodulating the cervical spinal cord of a subject by administering epidural stimulation to the cervical spinal cord or a region thereof at a frequency and intensity sufficient to regulate and/or to restore respiration; and/or neuromodulating the cervical
(Continued)

spinal cord of a subject with a magnetic stimulator at a frequency and intensity sufficient to regulate and/or to restore respiration.

14 Claims, 22 Drawing Sheets

(51) Int. Cl.
*A61N 2/00* (2006.01)
*A61N 2/02* (2006.01)

(52) U.S. Cl.
CPC ......... *A61N 1/36175* (2013.01); *A61N 2/006* (2013.01); *A61N 2/02* (2013.01); *A61N 1/3615* (2013.01); *A61N 1/36171* (2013.01)

(58) Field of Classification Search
CPC ... A61N 2/006; A61N 1/36171; A61N 1/3615
See application file for complete search history.

(56) References Cited

U.S. PATENT DOCUMENTS 3,650,277 A 3/1972 Sjostrand et al.
3,662,758 A 5/1972 Glover
3,724,467 A 4/1973 Avery et al.
4,044,774 A 8/1977 Corbin et al.
4,102,344 A 7/1978 Conway et al.
4,141,365 A 2/1979 Fischell et al.
4,285,347 A 8/1981 Hess
4,340,063 A 7/1982 Maurer
4,379,462 A 4/1983 Borkan et al.
4,398,537 A 8/1983 Holmbo
4,414,986 A 11/1983 Dickhudt et al.
4,538,624 A 9/1985 Tarjan
4,549,556 A 10/1985 Tajan et al.
4,559,948 A 12/1985 Liss et al.
4,569,352 A 2/1986 Petrofsky et al.
4,573,481 A 3/1986 Bullara et al.
4,724,842 A 2/1988 Charters
4,800,898 A 1/1989 Hess et al.
4,934,368 A 6/1990 Lynch
4,969,452 A 11/1990 Petrofsky et al.
5,002,053 A 3/1991 Garcia-Rill et al.
5,031,618 A 7/1991 Mullett
5,066,272 A 11/1991 Eaton et al.
5,081,989 A 1/1992 Graupe et al.
5,121,754 A 6/1992 Mullett
5,344,439 A 9/1994 Otten
5,354,320 A 10/1994 Schaldach et al.
5,366,813 A 11/1994 Berlin
5,374,285 A 12/1994 Vaiani et al.
5,417,719 A 5/1995 Hull et al.
5,476,441 A 12/1995 Durfee et al.
5,562,718 A 10/1996 Palermo
5,643,330 A 7/1997 Holsheimer et al.
5,733,322 A 3/1998 Starkebaum
5,983,141 A 11/1999 Sluijter et al.
6,058,331 A 5/2000 King
6,066,163 A 5/2000 John
6,104,957 A 8/2000 Alo et al.
6,122,548 A 9/2000 Starkebaum et al.
6,308,103 B1 10/2001 Gielen
6,319,241 B1 11/2001 King et al.
6,463,327 B1 * 10/2002 Lurie .................. A61H 31/005
607/42
6,470,213 B1 10/2002 Alley
6,500,110 B1 12/2002 Davey et al.
6,503,231 B1 1/2003 Prausnitz et al.
6,505,074 B2 1/2003 Boveja et al.
6,516,227 B1 2/2003 Meadows et al.
6,551,849 B1 4/2003 Kenney
6,587,724 B2 7/2003 Mann
6,662,053 B2 12/2003 Borkan
6,666,831 B1 12/2003 Edgerton et al.
6,685,729 B2 2/2004 Gonzalez
6,748,276 B1 6/2004 Daignault, Jr. et al.
6,819,956 B2 11/2004 DiLorenzo
6,839,594 B2 1/2005 Cohen et al.
6,862,479 B1 3/2005 Whitehurst et al.
6,871,099 B1 3/2005 Whitehurst et al.
6,878,112 B2 4/2005 Linberg et al.
6,892,098 B2 5/2005 Ayal et al.
6,895,280 B2 5/2005 Meadows et al.
6,895,283 B2 5/2005 Erickson et al.
6,937,891 B2 8/2005 Leinders et al.
6,950,706 B2 9/2005 Rodriguez et al.
6,975,907 B2 12/2005 Zanakis et al.
6,988,006 B2 1/2006 King et al.
6,999,820 B2 2/2006 Jordan
7,020,521 B1 3/2006 Brewer et al.
7,024,247 B2 4/2006 Gliner et al.
7,035,690 B2 4/2006 Goetz
7,047,084 B2 5/2006 Erickson et al.
7,065,408 B2 6/2006 Herman et al.
7,096,070 B1 8/2006 Jenkins et al.
7,110,820 B2 9/2006 Tcheng et al.
7,127,287 B2 10/2006 Duncan et al.
7,127,296 B2 10/2006 Bradley
7,127,297 B2 10/2006 Law et al.
7,149,773 B2 12/2006 Haller et al.
7,153,242 B2 12/2006 Goffer
7,184,837 B2 2/2007 Goetz
7,200,443 B2 4/2007 Faul
7,209,787 B2 4/2007 DiLorenzo
7,228,179 B2 6/2007 Campen et al.
7,239,920 B1 7/2007 Thacker et al.
7,251,529 B2 7/2007 Greenwood-Van Meerveld
7,252,090 B2 8/2007 Goetz
7,313,440 B2 12/2007 Miesel et al.
7,324,853 B2 1/2008 Ayal et al.
7,330,760 B2 2/2008 Heruth et al.
7,337,005 B2 2/2008 Kim et al.
7,337,006 B2 2/2008 Kim et al.
7,340,298 B1 3/2008 Barbut
7,381,192 B2 6/2008 Brodard et al.
7,415,309 B2 8/2008 McIntyre
7,463,927 B1 12/2008 Chaouat
7,463,928 B2 12/2008 Lee et al.
7,467,016 B2 12/2008 Colborn
7,493,170 B1 2/2009 Segel et al.
7,496,404 B2 2/2009 Meadows et al.
7,502,652 B2 3/2009 Gaunt et al.
7,536,226 B2 5/2009 Williams et al.
7,544,185 B2 6/2009 Bengtsson
7,584,000 B2 9/2009 Erickson
7,590,454 B2 9/2009 Garabedian et al.
7,603,178 B2 10/2009 North et al.
7,620,502 B2 11/2009 Selifonov et al.
7,628,750 B2 12/2009 Cohen et al.
7,647,115 B2 1/2010 Levin et al.
7,660,636 B2 2/2010 Castel et al.
7,697,995 B2 4/2010 Cross et al.
7,725,193 B1 5/2010 Chu
7,729,781 B2 6/2010 Swoyer et al.
7,734,340 B2 6/2010 De Ridder
7,734,351 B2 6/2010 Testerman et al.
7,742,037 B2 6/2010 Sako et al.
7,769,463 B2 8/2010 Katsnelson
7,797,057 B2 9/2010 Harris
7,801,601 B2 9/2010 Maschino et al.
7,813,803 B2 10/2010 Heruth et al.
7,813,809 B2 10/2010 Strother et al.
7,840,270 B2 11/2010 Ignagni et al.
7,856,264 B2 12/2010 Firlik et al.
7,877,146 B2 1/2011 Rezai et al.
7,890,182 B2 2/2011 Parramon et al.
7,949,395 B2 5/2011 Kuzma
7,949,403 B2 5/2011 Palermo et al.
7,987,000 B2 7/2011 Moffitt et al.
7,991,465 B2 8/2011 Bartic et al.
8,019,427 B2 9/2011 Moffitt
8,050,773 B2 11/2011 Zhu
8,108,051 B2 1/2012 Cross, Jr. et al.

(56) References Cited

U.S. PATENT DOCUMENTS 8,108,052 B2 1/2012 Boling
8,131,358 B2 3/2012 Moffitt et al.
8,135,473 B2 3/2012 Miesel et al.
8,155,750 B2 4/2012 Jaax et al.
8,168,481 B2 5/2012 Hanaoka et al.
8,170,660 B2 5/2012 Dacey, Jr. et al.
8,190,262 B2 5/2012 Gerber et al.
8,195,304 B2 6/2012 Strother et al.
8,214,048 B1 7/2012 Whitehurst et al.
8,229,565 B2 7/2012 Kim et al.
8,239,038 B2 8/2012 Wolf, II
8,260,436 B2 9/2012 Gerber et al.
8,271,099 B1 9/2012 Swanson
8,295,936 B2 10/2012 Wahlstrand et al.
8,311,644 B2 11/2012 Moffitt et al.
8,326,569 B2 12/2012 Lee et al.
8,332,029 B2 12/2012 Glukhovsky et al.
8,332,047 B2 12/2012 Libbus et al.
8,346,366 B2 1/2013 Arle et al.
8,352,036 B2 1/2013 DiMarco et al.
8,355,791 B2 1/2013 Moffitt
8,355,797 B2 1/2013 Caparso et al.
8,364,273 B2 1/2013 De Ridder
8,369,961 B2 2/2013 Christman et al.
8,374,696 B2 2/2013 Sanchez et al.
8,412,345 B2 4/2013 Moffitt
8,428,728 B2 4/2013 Sachs
8,442,655 B2 5/2013 Moffitt et al.
8,452,406 B2 5/2013 Arcot-Krishmamurthy et al.
8,543,200 B2 9/2013 Lane et al.
8,588,884 B2 11/2013 Hegde et al.
8,700,145 B2 4/2014 Kilgard et al.
8,712,546 B2 4/2014 Kim et al.
8,740,825 B2 6/2014 Ehrenreich et al.
8,750,957 B2 6/2014 Tang et al.
8,768,481 B2 7/2014 Lane
8,805,542 B2 8/2014 Tai et al.
9,072,891 B1 7/2015 Rao
9,079,039 B2 7/2015 Carlson et al.
9,101,769 B2 8/2015 Edgerton et al.
9,205,259 B2 12/2015 Kim et al.
9,205,260 B2 12/2015 Kim et al.
9,205,261 B2 12/2015 Kim et al.
9,248,291 B2 2/2016 Mashiach
9,272,139 B2 3/2016 Hamilton et al.
9,272,143 B2 3/2016 Libbus et al.
9,283,391 B2 3/2016 Ahmed
9,314,630 B2 4/2016 Levin et al.
9,393,409 B2 7/2016 Edgerton et al.
9,409,023 B2 8/2016 Burdick et al.
9,415,218 B2 8/2016 Edgerton et al.
9,421,365 B2 8/2016 Sumners et al.
9,597,517 B2 3/2017 Moffitt
9,610,442 B2 4/2017 Yoo et al.
9,802,052 B2 10/2017 Marnfeldt
9,895,545 B2 2/2018 Rao et al.
9,993,642 B2 6/2018 Gerasimenko et al.
10,092,750 B2 10/2018 Edgerton et al.
10,124,166 B2 11/2018 Edgerton et al.
10,137,299 B2 11/2018 Lu et al.
10,449,371 B2 10/2019 Serrano Carmona
10,751,533 B2 8/2020 Edgerton et al.
10,773,074 B2 9/2020 Liu et al.
10,806,927 B2 10/2020 Edgerton et al.
10,806,935 B2 10/2020 Rao et al.
11,097,122 B2 8/2021 Lu
11,123,312 B2 9/2021 Lu et al.
11,266,850 B2 3/2022 Prouza et al.
11,400,284 B2 8/2022 Gerasimenko et al.
2001/0016266 A1 8/2001 Okazaki et al.
2001/0032992 A1 10/2001 Wendt
2002/0042814 A1 4/2002 Fukasawa et al.
2002/0052539 A1 5/2002 Haller et al.
2002/0055779 A1 5/2002 Andrews
2002/0083240 A1 6/2002 Hoese et al.
2002/0111661 A1 8/2002 Cross et al.
2002/0115945 A1 8/2002 Herman et al.
2002/0188332 A1 12/2002 Lurie et al.
2002/0193843 A1 12/2002 Hill et al.
2003/0032992 A1 2/2003 Thacker et al.
2003/0078633 A1 4/2003 Firlik et al.
2003/0093021 A1 5/2003 Goffer
2003/0093131 A1 5/2003 Loeb et al.
2003/0100933 A1 5/2003 Ayal et al.
2003/0114894 A1 6/2003 Dar et al.
2003/0158583 A1 8/2003 Burnett et al.
2003/0220679 A1 11/2003 Han
2003/0233137 A1 12/2003 Paul, Jr.
2004/0039425 A1 2/2004 Greenwood-Van Meerveld
2004/0044380 A1 3/2004 Bruninga et al.
2004/0111118 A1 6/2004 Hill et al.
2004/0111126 A1 6/2004 Tanagho et al.
2004/0122483 A1 6/2004 Nathan et al.
2004/0127954 A1 7/2004 McDonald, III
2004/0133248 A1 7/2004 Frei et al.
2004/0138518 A1 7/2004 Rise et al.
2004/0172027 A1 9/2004 Speitling et al.
2004/0172097 A1 9/2004 Brodard et al.
2004/0181263 A1 9/2004 Balzer et al.
2004/0267320 A1 12/2004 Taylor et al.
2005/0004622 A1 1/2005 Cullen et al.
2005/0061315 A1 3/2005 Lee et al.
2005/0070982 A1 3/2005 Heruth et al.
2005/0075669 A1 4/2005 King
2005/0075678 A1 4/2005 Faul
2005/0090756 A1 4/2005 Wolf et al.
2005/0101827 A1 5/2005 Delisle
2005/0102007 A1 5/2005 Ayal et al.
2005/0113882 A1 5/2005 Cameron et al.
2005/0119713 A1 6/2005 Whitehurst et al.
2005/0125045 A1 6/2005 Brighton et al.
2005/0209655 A1 9/2005 Bradley et al.
2005/0231186 A1 10/2005 Saavedra Barrera et al.
2005/0246004 A1 11/2005 Cameron et al.
2005/0277999 A1 12/2005 Strother et al.
2005/0278000 A1 12/2005 Strother et al.
2006/0003090 A1 1/2006 Rodger et al.
2006/0015153 A1 1/2006 Gliner et al.
2006/0018360 A1 1/2006 Tai et al.
2006/0041225 A1 2/2006 Wallace et al.
2006/0041295 A1 2/2006 Osypka
2006/0089696 A1 4/2006 Olsen et al.
2006/0100671 A1 5/2006 Ridder
2006/0111754 A1 5/2006 Rezai et al.
2006/0122678 A1 6/2006 Olsen et al.
2006/0142337 A1 6/2006 Ikeura et al.
2006/0142816 A1 6/2006 Fruitman et al.
2006/0142822 A1 6/2006 Tulgar
2006/0149333 A1 7/2006 Tanagho et al.
2006/0149337 A1 7/2006 John
2006/0189839 A1 8/2006 Laniado et al.
2006/0195153 A1 8/2006 DiUbaldi et al.
2006/0239482 A1 10/2006 Hatoum
2006/0241356 A1 10/2006 Flaherty
2006/0282127 A1 12/2006 Zealear
2007/0004567 A1 1/2007 Shetty et al.
2007/0016097 A1 1/2007 Farquhar et al.
2007/0016266 A1 1/2007 Paul
2007/0016329 A1 1/2007 Herr et al.
2007/0021513 A1 1/2007 Agee et al.
2007/0027495 A1 2/2007 Gerber
2007/0047852 A1 3/2007 Sharp et al.
2007/0049814 A1 3/2007 Muccio
2007/0055337 A1 3/2007 Tanrisever
2007/0060954 A1 3/2007 Cameron et al.
2007/0060980 A1 3/2007 Strother et al.
2007/0067003 A1 3/2007 Sanchez et al.
2007/0073357 A1 3/2007 Rooney et al.
2007/0083240 A1 4/2007 Peterson et al.
2007/0100389 A1 5/2007 Jaax et al.
2007/0121702 A1 5/2007 LaGuardia et al.
2007/0121709 A1 5/2007 Ittogi
2007/0142874 A1 6/2007 John
2007/0150023 A1 6/2007 Ignagni et al.

(56) References Cited

U.S. PATENT DOCUMENTS

2007/0150034 A1 6/2007 Rooney et al.
2007/0156172 A1 7/2007 Alvarado
2007/0156179 A1 7/2007 S.E.
2007/0156200 A1 7/2007 Kornet et al.
2007/0168008 A1 7/2007 Olsen
2007/0179534 A1 8/2007 Firlik et al.
2007/0179579 A1 8/2007 Feler et al.
2007/0191709 A1 8/2007 Swanson
2007/0208381 A1 9/2007 Hill et al.
2007/0233204 A1 10/2007 Lima et al.
2007/0255372 A1 11/2007 Metzler et al.
2007/0265621 A1 11/2007 Matthis et al.
2007/0265679 A1 11/2007 Bradley et al.
2007/0265691 A1 11/2007 Swanson
2007/0276449 A1 11/2007 Gunter et al.
2007/0276450 A1 11/2007 Meadows et al.
2007/0293910 A1 12/2007 Strother et al.
2008/0002227 A1 1/2008 Tsujimoto
2008/0004674 A1 1/2008 King et al.
2008/0009927 A1 1/2008 Vilims
2008/0021513 A1 1/2008 Thacker et al.
2008/0027346 A1 1/2008 Litt et al.
2008/0046049 A1 2/2008 Skubitz et al.
2008/0051851 A1 2/2008 Lin
2008/0071325 A1 3/2008 Bradley
2008/0077192 A1 3/2008 Harry et al.
2008/0103579 A1 5/2008 Gerber
2008/0105185 A1 5/2008 Kuhlman
2008/0140152 A1 6/2008 Imran et al.
2008/0140162 A1 6/2008 Goetz et al.
2008/0140169 A1 6/2008 Imran
2008/0147143 A1 6/2008 Popovic et al.
2008/0154329 A1 6/2008 Pyles et al.
2008/0183224 A1 7/2008 Barolat
2008/0200749 A1 8/2008 Zheng et al.
2008/0207985 A1 8/2008 Farone
2008/0208287 A1 8/2008 Palermo et al.
2008/0215113 A1 9/2008 Pawłowicz
2008/0221653 A1 9/2008 Agrawal et al.
2008/0224226 A1 9/2008 Suzuki et al.
2008/0228241 A1 9/2008 Sachs
2008/0228250 A1 9/2008 Mironer
2008/0234121 A1 9/2008 Kim et al.
2008/0234791 A1 9/2008 Arle et al.
2008/0279896 A1 11/2008 Heinen et al.
2008/0294211 A1 11/2008 Moffitt
2009/0012436 A1 1/2009 Lanfermann et al.
2009/0024997 A1 1/2009 Kobayashi
2009/0093854 A1 4/2009 Leung et al.
2009/0112281 A1 4/2009 Miyazawa et al.
2009/0118365 A1 5/2009 Benson, III et al.
2009/0131995 A1 5/2009 Sloan et al.
2009/0157141 A1 6/2009 Chiao et al.
2009/0198305 A1 8/2009 Naroditsky et al.
2009/0204173 A1 8/2009 Fang et al.
2009/0229166 A1 9/2009 Sawrie
2009/0270960 A1 10/2009 Zhao et al.
2009/0281529 A1 11/2009 Carriazo
2009/0281599 A1 11/2009 Thacker et al.
2009/0293270 A1 12/2009 Brindley et al.
2009/0299166 A1 12/2009 Nishida et al.
2009/0299167 A1 12/2009 Seymour
2009/0306491 A1 12/2009 Haggers
2010/0004715 A1 1/2010 Fahey
2010/0010646 A1 1/2010 Drew et al.
2010/0023103 A1 1/2010 Elborno
2010/0029040 A1 2/2010 Nomoto
2010/0042193 A1 2/2010 Slavin
2010/0070007 A1 3/2010 Parker et al.
2010/0114205 A1 5/2010 Donofrio et al.
2010/0114239 A1 5/2010 McDonald et al.
2010/0125313 A1 5/2010 Lee et al.
2010/0137938 A1 6/2010 Kishawi et al.
2010/0145428 A1 6/2010 Cameron et al.
2010/0152811 A1 6/2010 Flaherty
2010/0166546 A1 7/2010 Mahan et al.
2010/0168820 A1 7/2010 Maniak et al.
2010/0185253 A1* 7/2010 Dimarco .............. A61N 1/0553 607/42
2010/0198298 A1 8/2010 Glukhovsky et al.
2010/0217355 A1 8/2010 Tass et al.
2010/0228310 A1* 9/2010 Shuros ................ A61N 1/0551 607/17
2010/0241191 A1 9/2010 Testerman et al.
2010/0268299 A1 10/2010 Farone
2010/0274312 A1 10/2010 Alataris et al.
2010/0280570 A1 11/2010 Sturm et al.
2010/0305660 A1 12/2010 Hegi et al.
2010/0312304 A1 12/2010 York et al.
2010/0318168 A1 12/2010 Bighetti
2010/0331925 A1 12/2010 Peterson
2011/0006793 A1 1/2011 Peschke et al.
2011/0009919 A1 1/2011 Carbunaru et al.
2011/0016081 A1 1/2011 Basak et al.
2011/0029040 A1 2/2011 Walker et al.
2011/0029044 A1 2/2011 Hyde et al.
2011/0034277 A1 2/2011 Brandes
2011/0034977 A1 2/2011 Janik et al.
2011/0040349 A1 2/2011 Graupe
2011/0054567 A1 3/2011 Lane et al.
2011/0054568 A1 3/2011 Lane et al.
2011/0054570 A1 3/2011 Lane
2011/0054579 A1 3/2011 Kumar et al.
2011/0077660 A1 3/2011 Janik et al.
2011/0082515 A1 4/2011 Libbus et al.
2011/0084489 A1 4/2011 Kaplan
2011/0093043 A1 4/2011 Torgerson et al.
2011/0112601 A1 5/2011 Meadows et al.
2011/0125203 A1 5/2011 Simon et al.
2011/0130804 A1 6/2011 Lin et al.
2011/0152967 A1 6/2011 Simon et al.
2011/0160810 A1 6/2011 Griffith
2011/0166546 A1 7/2011 Jaax et al.
2011/0184482 A1 7/2011 Eberman et al.
2011/0184488 A1 7/2011 De Ridder
2011/0184489 A1 7/2011 Nicolelis et al.
2011/0202107 A1 8/2011 Sunagawa et al.
2011/0208265 A1 8/2011 Erickson et al.
2011/0213266 A1 9/2011 Williams et al.
2011/0218590 A1 9/2011 DeGIORGIO et al.
2011/0218594 A1 9/2011 Doran et al.
2011/0224153 A1 9/2011 Levitt et al.
2011/0224665 A1 9/2011 Crosby et al.
2011/0224752 A1 9/2011 Rolston et al.
2011/0224753 A1 9/2011 Palermo et al.
2011/0224757 A1 9/2011 Zdeblick et al.
2011/0230101 A1 9/2011 Tang et al.
2011/0230701 A1 9/2011 Simon et al.
2011/0230702 A1* 9/2011 Honour .................. A61N 2/006 600/13
2011/0231326 A1 9/2011 Marino
2011/0237221 A1 9/2011 Prakash et al.
2011/0237921 A1 9/2011 Askin, III et al.
2011/0245734 A1 10/2011 Wagner et al.
2011/0276107 A1 11/2011 Simon et al.
2011/0288609 A1 11/2011 Tehrani et al.
2011/0295100 A1 12/2011 Rolston et al.
2012/0006793 A1 1/2012 Swanson
2012/0011222 A1 1/2012 Yasukawa et al.
2012/0011950 A1 1/2012 Kracke
2012/0013041 A1 1/2012 Cao et al.
2012/0013126 A1 1/2012 Molloy
2012/0016448 A1 1/2012 Lee
2012/0029528 A1 2/2012 Macdonald et al.
2012/0035684 A1 2/2012 Thompson et al.
2012/0041518 A1 2/2012 Kim et al.
2012/0052432 A1 3/2012 Matsuura
2012/0053645 A1 3/2012 Ayanoor-Vitikkate et al.
2012/0071250 A1 3/2012 O'Neil et al.
2012/0071950 A1 3/2012 Archer
2012/0083709 A1 4/2012 Parker et al.
2012/0101326 A1 4/2012 Simon et al.
2012/0109251 A1 5/2012 Lebedev et al.
2012/0109295 A1 5/2012 Fan

(56) References Cited

U.S. PATENT DOCUMENTS

2012/0116476 A1 5/2012 Kothandaraman
2012/0123223 A1 5/2012 Freeman et al.
2012/0123293 A1 5/2012 Shah et al.
2012/0126392 A1 5/2012 Kalvesten et al.
2012/0136408 A1 5/2012 Grill et al.
2012/0165899 A1 6/2012 Gliner
2012/0172222 A1 7/2012 Artigas Puerto
2012/0172246 A1 7/2012 Nguyen et al.
2012/0172946 A1 7/2012 Altaris et al.
2012/0179222 A1 7/2012 Jaax et al.
2012/0185020 A1 7/2012 Simon et al.
2012/0197338 A1 8/2012 Su et al.
2012/0203055 A1 8/2012 Pletnev
2012/0203131 A1 8/2012 DiLorenzo
2012/0221073 A1 8/2012 Southwell et al.
2012/0232615 A1 9/2012 Barolat et al.
2012/0252874 A1 10/2012 Feinstein et al.
2012/0259380 A1 10/2012 Pyles
2012/0271372 A1 10/2012 Osorio
2012/0277824 A1 11/2012 Li
2012/0277834 A1 11/2012 Mercanzini et al.
2012/0283697 A1 11/2012 Kim et al.
2012/0283797 A1 11/2012 De Ridder
2012/0302821 A1 11/2012 Burnett
2012/0310305 A1 12/2012 Kaula et al.
2012/0310315 A1 12/2012 Savage et al.
2012/0330321 A1 12/2012 Johnson et al.
2012/0330391 A1 12/2012 Bradley et al.
2013/0012853 A1 1/2013 Brown
2013/0013041 A1 1/2013 Glukhovsky et al.
2013/0026640 A1 1/2013 Ito et al.
2013/0030312 A1 1/2013 Keel et al.
2013/0030319 A1 1/2013 Hettrick et al.
2013/0030501 A1 1/2013 Feler et al.
2013/0035745 A1 2/2013 Ahmed et al.
2013/0053734 A1 2/2013 Barriskill et al.
2013/0053922 A1 2/2013 Ahmed et al.
2013/0066392 A1 3/2013 Simon et al.
2013/0066411 A1 3/2013 Thacker et al.
2013/0085317 A1 4/2013 Feinstein
2013/0085361 A1 4/2013 Mercanzini et al.
2013/0096640 A1 4/2013 Possover
2013/0096661 A1 4/2013 Greenberg et al.
2013/0096662 A1 4/2013 Swanson
2013/0110196 A1 5/2013 Alataris et al.
2013/0116751 A1 5/2013 Moffitt et al.
2013/0123568 A1 5/2013 Hamilton et al.
2013/0123659 A1 5/2013 Bartol et al.
2013/0138167 A1 5/2013 Bradley et al.
2013/0165991 A1 6/2013 Kim et al.
2013/0197408 A1 8/2013 Goldfarb et al.
2013/0204324 A1 8/2013 Thacker et al.
2013/0211477 A1 8/2013 Cullen et al.
2013/0237948 A1 9/2013 Donders et al.
2013/0253222 A1 9/2013 Nakao
2013/0253229 A1 9/2013 Sawant et al.
2013/0253299 A1 9/2013 Weber et al.
2013/0253611 A1 9/2013 Lee et al.
2013/0268016 A1 10/2013 Xi et al.
2013/0268021 A1 10/2013 Moffitt
2013/0281890 A1 10/2013 Mishelevich
2013/0289446 A1 10/2013 Stone et al.
2013/0289664 A1 10/2013 Johanek
2013/0289667 A1 10/2013 Wacnik et al.
2013/0296965 A1 11/2013 Mokelke et al.
2013/0303873 A1 11/2013 Voros et al.
2013/0304159 A1 11/2013 Simon et al.
2013/0310211 A1 11/2013 Wilton et al.
2013/0310911 A1 11/2013 Tai et al.
2014/0005753 A1 1/2014 Carbunaru
2014/0031893 A1 1/2014 Walker et al.
2014/0046407 A1 2/2014 Ben-Ezra et al.
2014/0058292 A1 2/2014 Alford et al.
2014/0058490 A1 2/2014 DiMarco
2014/0066950 A1 3/2014 Macdonald et al.
2014/0067007 A1 3/2014 Drees et al.
2014/0067354 A1 3/2014 Kaula et al.
2014/0074190 A1 3/2014 Griffith
2014/0081011 A1 3/2014 Vaught et al.
2014/0081071 A1 3/2014 Simon et al.
2014/0088674 A1 3/2014 Bradley
2014/0100633 A1 4/2014 Mann et al.
2014/0107397 A1 4/2014 Simon et al.
2014/0107398 A1 4/2014 Simon et al.
2014/0114374 A1 4/2014 Rooney et al.
2014/0142652 A1 5/2014 Francois et al.
2014/0163640 A1 6/2014 Edgerton et al.
2014/0172045 A1 6/2014 Yip et al.
2014/0180361 A1 6/2014 Burdick et al.
2014/0213842 A1 7/2014 Simon et al.
2014/0228905 A1 8/2014 Bolea
2014/0236257 A1 8/2014 Parker et al.
2014/0243923 A1 8/2014 Doan et al.
2014/0277271 A1 9/2014 Chan et al.
2014/0296752 A1 10/2014 Edgerton et al.
2014/0303901 A1 10/2014 Sadeh
2014/0316484 A1 10/2014 Edgerton et al.
2014/0316503 A1 10/2014 Tai et al.
2014/0324118 A1 10/2014 Simon et al.
2014/0330067 A1 11/2014 Jordan
2014/0330335 A1 11/2014 Errico et al.
2014/0336722 A1 11/2014 Rocon De Lima et al.
2014/0357936 A1 12/2014 Simon et al.
2015/0005840 A1 1/2015 Pal et al.
2015/0065559 A1 3/2015 Feinstein et al.
2015/0066111 A1 3/2015 Blum et al.
2015/0165226 A1 6/2015 Simon et al.
2015/0182784 A1 7/2015 Barriskill et al.
2015/0190634 A1 7/2015 Rezai et al.
2015/0196231 A1 7/2015 Ziaie et al.
2015/0217120 A1 8/2015 Nandra et al.
2015/0231396 A1 8/2015 Burdick et al.
2015/0265830 A1* 9/2015 Simon .................... A61N 2/008 600/13
2015/0328462 A1 11/2015 Griffith
2016/0001096 A1 1/2016 Mishelevich
2016/0030737 A1 2/2016 Gerasimenko et al.
2016/0030748 A1 2/2016 Edgerton et al.
2016/0030750 A1 2/2016 Bokil et al.
2016/0045727 A1 2/2016 Rezai et al.
2016/0045731 A1 2/2016 Simon et al.
2016/0074663 A1 3/2016 De Ridder
2016/0121109 A1* 5/2016 Edgerton ........... A61N 1/36003 607/45
2016/0121114 A1 5/2016 Simon et al.
2016/0121116 A1 5/2016 Simon et al.
2016/0121121 A1 5/2016 Mashiach
2016/0143588 A1 5/2016 Hoitink et al.
2016/0157389 A1 6/2016 Hwang
2016/0175586 A1 6/2016 Edgerton et al.
2016/0220813 A1 8/2016 Edgerton et al.
2016/0235977 A1 8/2016 Lu et al.
2016/0271413 A1 9/2016 Vallejo et al.
2016/0279418 A1 9/2016 Courtine et al.
2016/0279429 A1 9/2016 Hershey et al.
2016/0310739 A1 10/2016 Burdick et al.
2016/0339239 A1 11/2016 Yoo et al.
2017/0007831 A1 1/2017 Edgerton et al.
2017/0128729 A1 5/2017 Netoff et al.
2017/0157389 A1 6/2017 Tai et al.
2017/0157396 A1 6/2017 Dixon et al.
2017/0161454 A1 6/2017 Grill et al.
2017/0165497 A1 6/2017 Lu
2017/0173326 A1 6/2017 Bloch et al.
2017/0246450 A1* 8/2017 Liu ........................ B05D 1/005
2017/0246452 A1 8/2017 Liu et al.
2017/0266455 A1 9/2017 Steinke
2017/0274209 A1 9/2017 Edgerton et al.
2017/0296837 A1 10/2017 Jin
2017/0354819 A1 12/2017 Bloch et al.
2017/0361093 A1 12/2017 Yoo et al.
2018/0008826 A1 1/2018 Dimarco
2018/0056078 A1 3/2018 Kashyap et al.
2018/0085583 A1 3/2018 Zhang et al.

(56) References Cited

U.S. PATENT DOCUMENTS

2018/0104479 A1 4/2018 Grill et al.
2018/0110992 A1 4/2018 Parramon et al.
2018/0117334 A1 5/2018 Jung
2018/0125416 A1 5/2018 Schwarz et al.
2018/0178008 A1 6/2018 Bouton et al.
2018/0185648 A1 7/2018 Nandra et al.
2018/0193655 A1 7/2018 Zhang et al.
2018/0229037 A1 8/2018 Edgerton et al.
2018/0229038 A1 8/2018 Burdick et al.
2018/0236240 A1 8/2018 Harkema et al.
2018/0256906 A1 9/2018 Pivonka et al.
2018/0280693 A1 10/2018 Edgerton et al.
2018/0353755 A1 12/2018 Edgerton et al.
2018/0361146 A1 12/2018 Gerasimenko et al.
2019/0022371 A1 1/2019 Chang et al.
2019/0033622 A1 1/2019 Olgun et al.
2019/0160294 A1 5/2019 Peterson et al.
2019/0167987 A1 6/2019 Lu et al.
2019/0192852 A1 6/2019 De Ridder
2019/0192864 A1 6/2019 Koop et al.
2019/0247650 A1 8/2019 Tran
2019/0269917 A1 9/2019 Courtine et al.
2019/0381313 A1 12/2019 Lu
2019/0381328 A1 12/2019 Wechter et al.
2020/0155865 A1 5/2020 Lu
2020/0228901 A1 7/2020 Baek
2021/0069052 A1 3/2021 Burke
2021/0187278 A1 6/2021 Lu
2021/0236837 A1 8/2021 Lu
2021/0378991 A1 12/2021 Lu et al.
2022/0161042 A1 5/2022 Lu
2022/0233848 A1 7/2022 Gad et al.
2022/0313993 A1 10/2022 Gerasimenko et al.

FOREIGN PATENT DOCUMENTS

CA 2 823 592 A1 7/2012
CA 2 856 202 A1 5/2013
CA 2 864 473 A1 5/2013
CN 101227940 A 7/2008
CN 103263727 A 8/2013
CN 104307098 A 1/2015
EP 0630987 A1 12/1994
EP 2130326 A1 12/2009
EP 2141851 A2 1/2010
EP 2160127 A1 3/2010
EP 2178319 A1 4/2010
EP 2192897 A1 6/2010
EP 2226114 A1 9/2010
EP 2258496 A1 12/2010
EP 2361631 A1 8/2011
EP 2368401 A1 9/2011
EP 2387467 A1 11/2011
EP 2396995 A1 12/2011
EP 2397788 A1 12/2011
EP 2445990 A2 5/2012
EP 2471518 A2 7/2012
EP 2475283 A1 7/2012
EP 2486897 A2 8/2012
EP 2626051 A1 8/2013
EP 2628502 A1 8/2013
EP 2661307 A2 11/2013
EP 2688642 A2 1/2014
EP 2810689 A1 12/2014
EP 2810690 A1 12/2014
EP 2868343 A1 5/2015
EP 2966422 A1 1/2016
EP 2968940 A1 1/2016
EP 3184145 A1 6/2017
EP 3323468 A1 5/2018
EP 3328481 A1 6/2018
EP 3527258 A1 8/2019
JP H03-26620 A 2/1991
JP 3184145 B2 7/2001
JP 2002517283 A 6/2002
JP 2002200178 A 7/2002
JP 2004065529 A 3/2004
JP 2007-526798 A 9/2007
JP 2008067917 A 3/2008
JP 2008-543429 A 12/2008
JP 2011502586 A 1/2011
JP 2012515060 A 7/2012
JP 2013508119 A 3/2013
JP 2014514043 A 6/2014
JP 2016506255 A 3/2016
JP 6132856 B2 5/2017
JP 2017104685 A 6/2017
JP 2017525509 A 9/2017
JP 2018524113 A 8/2018
RU 2130326 C1 5/1999
RU 2141851 C1 11/1999
RU 2160127 C1 12/2000
RU 2178319 C2 1/2002
RU 2192897 C2 11/2002
RU 2001102533 11/2002
RU 2226114 C1 3/2004
RU 2258496 C2 8/2005
RU 2361631 C2 7/2009
RU 2368401 C1 9/2009
RU 2387467 C1 4/2010
RU 2396995 C2 8/2010
RU 2397788 C2 8/2010
RU 2445990 C1 3/2012
RU 2471518 C2 1/2013
RU 2475283 C2 2/2013
RU 2661307 C1 7/2018
WO WO 97/047357 A1 12/1997
WO WO-0234331 A2 5/2002
WO WO-02092165 A1 11/2002
WO WO-03005887 A2 1/2003
WO WO 03/026735 A2 4/2003
WO WO 03/092795 A1 11/2003
WO WO 2004/087116 A2 10/2004
WO WO-2005002663 A2 1/2005
WO WO 2005/051306 A2 6/2005
WO WO 2005/065768 A1 7/2005
WO WO 2005/087307 A2 9/2005
WO WO 2006/138069 A1 12/2006
WO WO-2006135751 A2 12/2006
WO WO 2007/007058 A1 1/2007
WO WO 2007/012114 A1 2/2007
WO WO-2007047852 A2 4/2007
WO WO-2007081764 A2 7/2007
WO WO 2007/107831 A2 9/2007
WO WO-2008075294 A1 6/2008
WO WO 2008/109862 A1 9/2008
WO WO-2008070807 A3 9/2008
WO WO 2008/121891 A1 10/2008
WO WO 2009/042217 A1 4/2009
WO WO 2009/111142 A2 9/2009
WO WO-2010021977 A1 2/2010
WO WO 2010/055421 A1 5/2010
WO WO-2010083308 A1 7/2010
WO WO 2010/114998 A1 10/2010
WO WO 2010/124128 A1 10/2010
WO WO-2011005607 A1 1/2011
WO WO-2011136875 A1 11/2011
WO WO-2012050200 A1 4/2012
WO WO-2012075195 A1 6/2012
WO WO-2012080964 A1 6/2012
WO WO 2012/094346 A2 7/2012
WO WO 2012/100260 A2 7/2012
WO WO 2012/129574 A2 9/2012
WO WO 2013/071307 A1 5/2013
WO WO 2013/071309 A1 5/2013
WO WO-2013152124 A1 10/2013
WO WO 2013/188965 A1 12/2013
WO WO-2014005075 A1 1/2014
WO WO-2014031142 A1 2/2014
WO WO-2014089299 A2 6/2014
WO 2014144785 A1 9/2014
WO WO-2014149895 A1 9/2014
WO WO-2014205356 A2 12/2014
WO WO-2014209877 A1 12/2014

(56) References Cited

FOREIGN PATENT DOCUMENTS

| | | | |
|---|---|---|---|
| WO | WO-2015000800 | A1 | 1/2015 |
| WO | WO 2015/048563 | A2 | 4/2015 |
| WO | WO-2015063127 | A1 | 5/2015 |
| WO | WO-2015106286 | A1 | 7/2015 |
| WO | WO 2016/029159 | A2 | 2/2016 |
| WO | 2016033369 | A1 | 3/2016 |
| WO | WO 2016/033372 | A1 | 3/2016 |
| WO | WO-2016064761 | A1 | 4/2016 |
| WO | WO-2016110804 | A1 | 7/2016 |
| WO | WO-2016112398 | A1 | 7/2016 |
| WO | WO-2016172239 | A1 | 10/2016 |
| WO | WO 2017/011410 | A1 | 1/2017 |
| WO | WO 2017/024276 | A1 | 2/2017 |
| WO | WO 2017/035512 | A1 | 3/2017 |
| WO | WO 2017/044904 | A1 | 3/2017 |
| WO | WO-2017058913 | A1 | 4/2017 |
| WO | WO-2017062508 | A1 | 4/2017 |
| WO | WO-2017117450 | A1 | 7/2017 |
| WO | WO-2017146659 | A1 | 8/2017 |
| WO | WO-2018039296 | A2 | 3/2018 |
| WO | WO 2018/106843 | A1 | 6/2018 |
| WO | WO 2018/140531 | A1 | 8/2018 |
| WO | WO 2018/217791 | A1 | 11/2018 |
| WO | WO-2019211314 | A1 | 11/2019 |
| WO | WO 2020/041502 | A1 | 2/2020 |
| WO | WO 2020/041633 | A1 | 2/2020 |
| WO | WO 2020/236946 | A1 | 11/2020 |

OTHER PUBLICATIONS

U.S. Office Action dated Apr. 8, 2015 issued in U.S. Appl. No. 14/355,812.
U.S. Final Office Action dated Sep. 21, 2015 issued in U.S. Appl. No. 14/355,812.
U.S. Notice of Allowance dated Apr. 13, 2016 issued in U.S. Appl. No. 14/355,812.
U.S. Office Action dated Oct. 18, 2016 issued in U.S. Appl. No. 15/208,529.
U.S. Final Office Action dated Jul. 13, 2017 issued in U.S. Appl. No. 15/208,529.
U.S. Office Action dated Jul. 27, 2018 issued in U.S. Appl. No. 15/208,529.
U.S. Final Office Action dated Apr. 19, 2019 issued in U.S. Appl. No. 15/208,529.
U.S. Office Action dated Oct. 28, 2019 issued in U.S. Appl. No. 15/208,529.
U.S. Office Action dated Oct. 3, 2017 issued in U.S. Appl. No. 15/025,201.
U.S. Notice of Allowance dated Aug. 1, 2018 issued in U.S. Appl. No. 15/025,201.
U.S. Office Action dated Jul. 13, 2016 issued in U.S. Appl. No. 14/775,618.
U.S. Final Office Action dated Apr. 25, 2017 issued in U.S. Appl. No. 14/775,618.
U.S. Notice of Allowance dated Jan. 18, 2018 issued in U.S. Appl. No. 14/775,618.
U.S. Office Action dated Jan. 8, 2020 issued in U.S. Appl. No. 15/975,678.
U.S. Office Action dated Oct. 31, 2019 issued in U.S. Appl. No. 15/750,499.
U.S. Office Action dated Jul. 22, 2019 issued in U.S. Appl. No. 15/506,696.
U.S. Office Action dated Jun. 4, 2019 issued in U.S. Appl. No. 15/505,053.
U.S. Office Action dated Apr. 17, 2019 issued in U.S. Appl. No. 15/344,381.
U.S. Final Office Action dated Dec. 30, 2019 issued in U.S. Appl. No. 15/344,381.
PCT International Search Report dated Jul. 30, 2012 issued in PCT/US2012/020112.
PCT International Preliminary Report on Patentability and Written Opinion dated Jul. 10, 2013 issued in PCT/US2012/020112.
PCT International Search Report and Written Opinion dated Mar. 19, 2013 issued in PCT/US2012/064878.
PCT International Preliminary Report on Patentability dated May 22, 2014 issued in PCT/US2012/064878.
Australian Patent Examination Report No. 1 dated Jul. 11, 2016 issued in AU 2012334926.
Canadian Office Action dated Aug. 31, 2018 issued in CA 2,864,473.
Canadian Office Action dated Jul. 30, 2019 issued in CA 2,864,473.
European Communication pursuant to Rule 114(2) EPC regarding observations by a third party dated Mar. 27, 2015 issued in EP 12 847 885.6.
European Extended Search Report dated May 6, 2015 issued in EP 12 847 885.6.
European Office Action dated Apr. 15, 2016 issued in EP 12 847 885.6.
European Reply to Communication of Apr. 15, 2016 dated Oct. 24, 2016 in EP 12 847 885.6.
European Second Office Action dated Feb. 16, 2017 issued in EP 12 847 885.6.
PCT Declaration of Non-Establishment of International Search Report and Written Opinion dated Dec. 24, 2014 issued in PCT/US2014/057886.
PCT International Preliminary Report on Patentability and Written Opinion dated Apr. 7, 2016 issued in PCT/US2014/057886.
Australian Examination report No. 1 dated Jan. 11, 2019 issued in AU 2014324660.
Australian Examination report No. 2 dated Nov. 7, 2019 issued in AU 2014324660.
Australian Examination report No. 3 dated Jan. 6, 2020 issued in AU 2014324660.
European Extended Search Report dated May 10, 2017 issued in EP 14849355.4.
European Office Action dated Jul. 20, 2018 issued in EP 14849355.4.
PCT International Search Report and Written Opinion dated Aug. 6, 2014 issued in PCT/US2014/029340.
PCT International Preliminary Report on Patentability dated Sep. 24, 2015 issued in PCT/US2014/029340.
Australian Patent Examination Report No. 1 dated May 11, 2018 issued in AU 2014228794.
Australian Patent Examination Report No. 1 dated Jan. 6, 2020 issued in AU 2019206059.
European Extended Search Report dated Nov. 8, 2016 issued in EP 14765477.6.
European Office Action dated Nov. 14, 2018 issued in EP 14765477.6.
European Office Action dated Sep. 27, 2019 issued in EP 14765477.6.
PCT International Search Report and Written Opinion dated Dec. 5, 2016 issued in PCT/US2016/045898.
PCT International Preliminary Report on Patentability and Written Opinion dated Feb. 15, 2018 issued in PCT/US2016/045898.
European Extended Search Report dated Dec. 13, 2018 issued in EP 16833973.7.
PCT International Search Report and Written Opinion dated Dec. 8, 2015 issued in PCT/US2015/047268.
PCT International Preliminary Report on Patentability and Written Opinion dated Feb. 28, 2017 issued in PCT/US2015/047268.
Australian Patent Examination Report No. 1 dated Jul. 18, 2019 issued in AU 2015308779.
European Extended Search Report dated Mar. 1, 2018 issued in EP 15836927.2.
PCT International Search Report and Written Opinion dated Dec. 3, 2015 issued in PCT/US2015/047272.
PCT International Preliminary Report on Patentability and Written Opinion dated Feb. 28, 2017 issued in PCT/US2015/047272.
PCT Declaration of Non-Establishment of International Search Report and Written Opinion dated Dec. 1, 2015 issued in PCT/US2015/046378.
PCT International Preliminary Report on Patentability and Written Opinion dated Feb. 21, 2017 issued in PCT/US2015/046378.

(56) References Cited

OTHER PUBLICATIONS

Australian Patent Examination Report No. 1 dated Jun. 14, 2019 issued in AU 2015305237.
European Extended Search Report dated Apr. 4, 2018 issued in EP 15834593.4.
European Office Action dated Jul. 17, 2019 issued in EP 15834593.4.
PCT International Search Report and Written Opinion dated Sep. 12, 2016 issued in PCT/US2016/041802.
PCT International Preliminary Report on Patentability and Written Opinion dated Jan. 25, 2018 issued in PCT/US2016/041802.
European Extended Search Report dated Feb. 19, 2019 issued in EP 16825005.8.
PCT International Search Report and Written Opinion dated Dec. 5, 2016 issued in PCT/US2016/049129.
PCT International Preliminary Report on Patentability and Written Opinion dated Mar. 8, 2018 issued in PCT/US2016/049129.
PCT International Search Report and Written Opinion dated Mar. 12, 2018 issued in PCT/US2018/015098.
PCT International Preliminary Report on Patentability and Written Opinion dated Jul. 30, 2019 issued in PCT/US2018/015098.
PCT International Search Report and Written Opinion dated Aug. 31, 2018 issued in PCT/US2018/033942.
PCT International Preliminary Report on Patentability and Written Opinion dated Nov. 26, 2019 issued in PCT/US2018/033942.
PCT International Search Report dated Mar. 19, 2013 issued in PCT/US2012/064874.
PCT International Search Report dated Mar. 19, 2013 issued in PCT/US2012/064878.
PCT International Search Report dated Sep. 3, 2012 issued in PCT/US2012/022257.
PCT International Search Report dated Oct. 31, 2012 issued in PCT/US2012/030624.
Andersson, et al., (2003) "CNS Involvement in Overactive Bladder." *Drugs,* 63(23):2595-2611.
Angeli et al. (2014) "Altering spinal cord excitability enables voluntary movements after chronic complete paralysis in humans" *Brain* 137: 1394-1409.
Courtine, Grégoire et al. (2007) "Modulation of multisegmental monosynaptic responses in a variety of leg muscles during walking and running in humans," *J Physiol.* 582.3:1125-1139.
Danner S.M., Hofstoetter U.S., Ladenbauer J., Rattay F., and Minassian K. (Mar. 2011) "Can the human lumbar posterior columns be stimulated by transcutaneous spinal cord stimulation? A modeling study" *Europe PMC Funders Author Manuscripts, Artif Organs* 35(3):257-262, 12 pp.
DeSantana et al. (Dec. 2008) "Effectiveness of Transcutaneous Electrical Nerve Stimulation for Treatment of Hyperalgesia and Pain," *Curr Rheumatol Rep.* 10(6):492-499, 12 pp.
Dubinsky, Richard M. and Miyasaki, Janis, "Assessment: Efficacy of transcutaneous electric nerve stimulation in the treatment of pain in neurologic disorders (an evidence-based review)," Report of the Therapeutics and Technology Assessment Subcommittee of the American Academy of Neurology, (2010) *Neurology,* 74:173-176.
Edgerton and Harkema (2011) "Epidural stimulation of the spinal cord in spinal cord injury: current status and future challenges" *Expert Rev Neurother.* 11(10): 1351-1353. doi: 10.1586/ern.11.129 [NIH Public Access—Author Manuscript—5 pages].
Fong et al. (2009) "Recovery of control of posture and locomotion after a spinal cord injury: solutions staring US in the face," *Progress in Brain Research,* Elsevier Amsterdam, NL, 175:393-418.
Ganley et al., (2005) "Epidural Spinal Cord Stimulation Improves Locomoter Performance in Low Asia C, Wheelchair-Dependent, Spinal Cord-Injured Individuals: Insights from Metabolic Response," *Top. Spinal Cord Inj. Rehabil;*11(2):50-63.
Gerasimenko Y., Gorodnichev R., Machueva E., Pivovarova E., Semyenov D., Savochin A., Roy R.R., and Edgerton V.R., (Mar. 10, 2010) "Novel and Direct Access to the Human Locomotor Spinal Circuitry," *J Neurosci.* 30(10):3700-3708, PMC2847395.
Gerasimenko Y.P., Ichiyama R.M., Lavrov I.A., Courtine G., Cai L., Zhong H., Roy R.R., and Edgerton V.R. (2007) "Epidural Spinal Cord Stimulation Plus Quipazine Administration Enable Stepping in Complete Spinal Adult Rats," *J Neurophysiol.* 98:2525-2536.
Harkema et al. (2011) "Effect of Epidural stimulation of the lumbosacral spinal cord on voluntary movement, standing, and assisted stepping after motor complete paraplegia: a case study" *Lancet* 377(9781): 1938-1947; NIH Public Access Author Manuscript 17 pages [doi:10.1016/S0140-6736(11)60547-3].
Herman R., He J., D'Luzansky S., Willis W., Dilli S., (2002) "Spinal cord stimulation facilitates functional walking in a chronic, incomplete spinal cord injured," *Spinal Cord.* 40:65-68.
Hofstoetter, U.S. et al. (Aug. 2008) "Modification of Reflex Responses to Lumbar Posterior Root Stimulation by Motor Tasks in Healthy Subjects," *Artif Organs,* 32(8):644-648.
Ichiyama et al. (2005) "Hindlimb stepping movements in complete spinal rats induced by epidural spinal cord stimulation" *Neuroscience Letters,* 383:339-344.
Kapetanakis, et al. (2017) "Cauda Equina Syndrome Due to Lumbar Disc Herniation: a Review of Literature," *Folia Medica,* 59(4): 377-86.
Kitano K., Koceja D.M. (2009) "Spinal reflex in human lower leg muscles evoked by transcutaneous spinal cord stimulation," *J Neurosci Methods.* 180:111-115.
Minasian et al. (2010) "Transcutaneous stimulation of the human lumbar spinal cord: Facilitating locomotor output in spinal cord injury," *Conf. Proceedings Soc. for Neurosci.,* Abstract No. 286.19, 1 page.
Minassian et al. (Aug. 2011) "Transcutaneous spinal cord stimulation," *International Society for Restorative Neurology,* http://restorativeneurology.org/resource-center/assessments/transcutaneous-lumbar-spinal-cord-stimulation/; http://restorativeneurology.org/wp-content/uploads/2011/08/Transcutaneous-spinal-cord-stimulation_long.pdf, 6 pp.
Minassian et al. (Mar. 2007) "Posterior root-muscle reflexes elicited by transcutaneous stimulation of the human lumbosacral cord," *Muscle & Nerve* 35:327-336.
Nandra et al., (2014) "Microelectrode Implants for Spinal Cord Stimulation in Rats," *Thesis, California Institute of Technology,* Pasadena, California, Defended on Sep. 24, 2014, 104 pages.
Nandra et al., (Jan. 23, 2011) "A Parylene-Based Microelectrode Arrary Implant for Spinal Cord Stimulation in Rats," *Conf. Proc. IEEE Eng. Med. Biol. Soc.,* pp. 1007-1010.
Rodger et al., (2007) "High Density Flexible Parylene-Based Multielectrode Arrays for Retinal and Spinal Cord Stimulation," Transducers & Eurosensors, Proc. Of the 14th International Conference on Solid-State Sensors, Actuators and Microsystems, Lyon, France, Jun. 10-14, 2007, *IEEE,* pp. 1385-1388.
Seifert et al. (Nov. 1, 2002) "Restoration of Movement Using Functional Electrical Stimulation and Bayes' Theorem," *The Journal of Neuroscience,* 22(1):9465-9474.
Tanabe et al. (2008) "Effects of transcutaneous electrical stimulation combined with locomotion-like movement in the treatment of post-stroke gait disorder: a single-case study," 30(5):411-416 abstract, 1 page.
Wang, et al. (2017) "Incidence of C5 nerve root palsy after cervical surgery," *Medicine,* 96(45), 14 pages.
Ward, Alex R. (Feb. 2009) "Electrical Stimulation Using Kilohertz-Frequency Alternating Current," (2009) *Phys Ther.*89(2):181-190 [published online Dec. 18, 2008].
U.S. Notice of Allowance dated Jun. 17, 2020 issued in U.S. Appl. No. 15/208,529.
U.S. Office Action dated Apr. 10, 2020 issued in U.S. Appl. No. 16/200,467.
U.S. Final Office Action dated Jul. 29, 2020 issued in U.S. Appl. No. 15/975,678.
U.S. Final Office Action dated Aug. 6, 2020 issued in U.S. Appl. No. 15/750,499.
U.S. Notice of Allowance dated May 4, 2020 issued in U.S. Appl. No. 15/506,696.
U.S. Notice of Allowance dated Feb. 13, 2020 issued in U.S. Appl. No. 15/505,053.

(56) References Cited

OTHER PUBLICATIONS

U.S. 2nd Notice of Allowance dated Jun. 4, 2020 issued in U.S. Appl. No. 15/505,053.
U.S. Office Action dated Aug. 4, 2020 issued in U.S. Appl. No. 15/344,381.
Canadian Office Action dated Aug. 14, 2020 issued in CA 2,864,473.
Canadian Office Action dated May 7, 2020 issued in CA 2,906,779.
Australian Patent Examination Report No. 2 dated May 20, 2020 issued in AU 2015308779.
Australian Patent Examination Report No. 2 dated Apr. 17, 2020 issued in AU 2015305237.
European Office Action dated Jul. 30, 2020 issued in EP 15834593.4.
Japanese Office Action dated Jul. 13, 2020 issued in JP 2018-501208.
European Extended Search Report dated Sep. 7, 2020 issued in EP 18744685.1.
PCT International Search Report and Written Opinion dated Nov. 14, 2019 issued in PCT/US2019/047777.
PCT International Search Report and Written Opinion dated Nov. 21, 2019 issued in PCT/US2019/047551.
Drummond, et al. (1996) "Thoracic impedance used for measuring chest wall movement in postoperative patients," *British Journal of Anaesthesia,* 77: 327-332.
Hovey, et al. (2006) "The Guide to Magnetic Stimulation," *The Magstim Company Ltd,* 45 pages.
Kondo, et al. (1997) "Laser monitoring of chest wall displacement," *Eur Respir J.,* 10: 1865-1869.
Niu et al., (2018) "A Proof-of-Concept Study of Transcutaneous Magnetic Spinal Cord Stimulation for Neurogenic Bladder," *Scientific Reports,* 8: 12549 (12 pages).
Szava et al., (Jan. 2011) "Transcutaneous electrical spinal cord stimulation: Biophysics of a new rehabilitation method after spinal cord injury", ISBN: 978-3-639-34154-6.
U.S. Office Action dated Nov. 24, 2020 issued in U.S. Appl. No. 16/200,467.
U.S. Office Action dated Feb. 10, 2021 issued in U.S. Appl. No. 15/975,678.
U.S. Office Action dated Nov. 13, 2020 issued in U.S. Appl. No. 15/753,963.
Australian Examination report No. 1 dated Dec. 21, 2020 issued in AU 2020200152.
Canadian Office Action dated Nov. 27, 2020 issued in CA 2,925,754.
Chinese First Office Action dated Jan. 6, 2021 issued in CN 201680058067.8.
PCT International Search Report and Written Opinion dated Oct. 14, 2020 issued in PCT/US2020/033830.
U.S. Notice of Allowance dated May 19, 2021 issued in U.S. Appl. No. 16/200,467.
U.S. Final Office Action dated Jul. 20, 2021 issued in U.S. Appl. No. 15/975,678.
U.S. Office Action dated Aug. 6, 2021 issued in U.S. Appl. No. 15/750,499.
U.S. Notice of Allowance dated Apr. 27, 2021 issued in U.S. Appl. No. 15/344,381.
U.S. Final Office Action dated Jul. 16, 2021 issued in U.S. Appl. No. 15/753,963.
U.S. Office Action dated May 12, 2021 issued in U.S. Appl. No. 16/615,765.
European Extended Search Report dated Jan. 22, 2021 issued in EP 20175385.2.
Canadian 2nd Office Action dated Apr. 9, 2021 issued in CA 2,906,779.
European Extended Search Report dated Aug. 17, 2021 issued in EP 21166801.7.
Japanese 2nd Office Action dated Mar. 22, 2021 issued in JP 2018-501208.
PCT International Preliminary Report on Patentability and Written Opinion dated Feb. 23, 2021 issued in PCT/US2019/047777.
PCT International Preliminary Report on Patentability and Written Opinion dated Feb. 23, 2021 issued in PCT/US2019/047551.
CA Office Action dated Oct. 21, 2021 in CA Application No. CA2958924.
CA Office Action dated Sep. 28, 2021, in application No. CA2925754.
Dimitrijevic et al. (1998) "Evidence for a spinal central pattern generator in humans." Ann N Y Acad Sci. 860:360-76.
European Office Action [Decision to Refuse] dated Oct. 28, 2021 issued in EP 15834593.4.
European Search Report dated Apr. 19, 2022, in Application No. EP20190851613.
European Search Report dated Apr. 19, 2022, in Application No. EP20190852797.
Gerasimenko et al. (2015) "Initiation and modulation of locomotor circuitry output with multisite transcutaneous electrical stimulation of the spinal cord in noninjured humans." J Neurophysiol. 113:834-42.
Gerasimenko et al. (2015) "Transcutaneous electrical spinal-cord stimulation in humans." Ann Phys Rehabil Med. 58(4):225-231. doi:10.1016/j.rehab.2015.05.003.
JP Office Action dated Nov. 29, 2021, in Application No. JP2019-539960 with English translation.
Krenn et al. (2013) "Selectivity of transcutaneous stimulation of lumbar posterior roots at different spinal levels in humans." Biomed Tech (Berl) 58 (Suppl. 1) DOI 10.1515/bmt-2013-4010, 2 pages.
Ladenbauer et al. (2010) "Stimulation of the human lumbar spinal cord with implanted and surface electrodes: a computer simulation study." IEEE Trans Neural Syst Rehabil Eng. 18:637-45.
PCT International Preliminary Report on Patentability and Written Opinion dated Dec. 2, 2021 issued in PCT/US2020/033830.
Roy et al. (2012) "Effect of percutaneous stimulation at different spinal levels on the activation of sensory and motor roots." Exp Brain Res. 223:281-9.
Sayenko et al. (2014) "Neuromodulation of evoked muscle potentials induced by epidural spinal-cord stimulation in paralyzed individuals." J Neurophysiol. 111:1088-99.
Sayenko et al. (2015) "Spinal segment-specific transcutaneous stimulation differentially shapes activation pattern among motor pools in humans." J Appl Physiol. 118:1364-74.
Shafik, A (1996) "Extrapelvic cavernous nerve stimulation in erectile dysfunction. Human study" Andrologia 28(3):151-6. doi: 10.1111/j.1439-0272.1996.tb02774.x [Abstract—2 pages].
Shafik, et al. (2000) "Magnetic stimulation of the cavernous nerve for the treatment of erectile dysfunction in humans" International Journal of Impotence Research 12: 137-141.
Temel, et al. (2004) "Deep brain stimulation of the thalamus can influence penile erection" International Journal of Impotence Research 16: 91-94.
Troni et al. (2011) "A methodological reappraisal of non invasive high voltage electrical stimulation of lumbosacral nerve roots." Clin Neurophysiol. 122:2071-80.
U.S. Final Office Action dated Dec. 6, 2021 issued in U.S. Appl. No. 16/615,765.
U.S. Notice of Allowance dated Dec. 13, 2021 issued in U.S. Appl. No. 15/753,963.
U.S. Notice of Allowance dated Mar. 4, 2022 issued in U.S. Appl. No. 15/975,678.
U.S. Office Action dated Jan. 5, 2022 issued in U.S. Appl. No. 17/269,970.
U.S. Restriction Requirement dated Apr. 19, 2022 in U.S. Appl. No. 16/479,201.
Augustine GJ, Purves D, Fitzpatrick D, eds., "Autonomic Regulation of the Bladder." Neuroscience, 2nd edition, Sunderland (MA): Sinauer Associates; 2001, Available from: https://www.ncbi.nlm.nih.gov/books/NBK10886/; downloaded Dec. 4, 2022, 2 pp.
CA Office Action dated Jul. 14, 2022 in Application No. CA2958924.
CA Office Action dated Sep. 6, 2022, in Application No. CA3030615.
Giuliano, F. et al., "Neural control of erection", Physiology & Behavior, vol. 83, No. 2, Nov. 15, 2004, pp. 189-201.
JP Office Action dated Nov. 21, 2022, in Application No. 2021-188658 with English translation.
JP Office Action dated Sep. 26, 2022, in Application No. JP2019-539960 with English translation.

(56) References Cited

OTHER PUBLICATIONS

U.S. Final Office Action dated Oct. 13, 2022, in U.S. Appl. No. 17/269,970.
U.S. Non Final Office Action dated Aug. 25, 2022 in U.S. Appl. No. 16/479,201.
U.S. Non-Final office Action dated Jun. 20, 2022 in U.S. Appl. No. 16/615,765.
U.S. Restriction Requirement dated Dec. 1, 2022 in U.S. Appl. No. 17/270,402.
Abernethy, J. et al., "Competing in the Dark: An Efficient Algorithm for Bandit Linear Optimization", Conference on Learning Theory, (2008), 13 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, (Sep. 2010), 9 pages.
Alto, L. et al., "Chemotropic Guidance Facilitates Axonal Regeneration and Synapse Formation after Spinal Cord Injury," Nature Neuroscience, vol. 12, No. 9, Published Online Aug. 2, 2009, (Sep. 2009), 21 pages.
Anderson, K., "Targeting Recovery: Priorities of the Spinal Cord-Injured Population," Journal of Neurotrauma, vol. 11, No. 10, Oct. 2004, 13 pages.
Auer, P. et al., "Finite-time Analysis of the Multiarmed Bandit Problem", Machine Learning, vol. 47, No. 2, (2002), pp. 235-256.
Auer, P. "Using Confidence Bounds for Exploitation-Exploration Trade-offs", Journal of Machine Learning Research, vol. 3, (2002), pp. 397-422.
Azimi, J. et al., "Batch Active Learning via Coordinated Matching", In Proceedings of the 29th International Conference on Machine Learning, (2012), 8 pages.
Azimi, J. et al., "Batch Bayesian Optimization via Simulation Matching", In Advances in Neural Information Processing Systems (NIPS), (2010), 9 pages.
Azimi, J. et al., "Hybrid Batch Bayesian Optimization", In Proceedings of the 29th International Conference on Machine Learning, (2012), 12 pages.
Barbeau, H. et al., "Recovery of locomotion after chronic spinalization in the adult cat", Brain Research, vol. 412, No. 1, (May 26, 1987), 12 pages.
Bareyre, F. et al., "The injured spinal cord spontaneously forms a new intraspinal circuit in adult rats," Nature Neuroscience, vol. 7, No. 3, Published Online Feb. 15, 2004, (Mar. 2004), 9 pages.
Basso, D. et al., "MASCIS Evaluation of Open Field Locomotor Scores: Effects of Experience and Teamwork on Reliability," Journal of Neurotrauma, vol. 13, No. 7, (Jul. 1996), 17 pages.
Brochu, et al., "A Tutorial on Bayesian Optimization of Expensive Cost Functions, with Application to Active User Modeling and Hierarchical Reinforcement Learning", In TR-2009-23, UBC, (2009), 49 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, (Sep. 22, 1997), 11 pages.
Bubeck, S. et al., "Online Optimization in X-Armed Bandits", Advances in Neural Information Processing Systems (NIPS), (2008), 8 pages.
Bubeck, S. et al., "Pure Exploration in Finitely-Armed and Continuous-Armed Bandits problems" In ALT, (2009), 35 pages.
Burke, R., "Group la Synaptic Input to Fast and Slow Twitch Motor Units of Cat Triceps Surae", The Journal of Physiology, vol. 196, vol. 3, (Jun. 1, 1968), 26 pages.
CA Office Action dated Jun. 19, 2023, in Application No. CA3030615.
Cai, L. et al., "Implications of Assist-As-Needed Robotic Step Training after a Complete Spinal Cord Injury on Intrinsic Strategies of Motor Learning", The Journal of Neuroscience, vol. 26, No. 41, (Oct. 11, 2006), 5 pages.
Capogrosso, M., et al., "A Computational Model for Epidural Electrical Stimulation of Spinal Sensorimotor Circuits", Journal of Neuroscience, Dec. 4, 2013, vol. 33, No. 49, pp. 19326-19340.
Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, (Mar. 15, 2004), 11 pages.
Colgate, E. et al., "An Analysis of Contact Instability in Terms of Passive Physical Equivalents," Proceedings of the 1989 IEEE International Conference on Robotics and Automation, Scottsdale, Arizona, (May 14, 1989), 6 pages.
Courtine, G. et al., "Can experiments in nonhuman primates expedite the translation of treatments for spinal cord injury in humans?", Nature Medicine, vol. 13, No. 5, (May 2007), 13 pages.
Courtine, G. et al., "Recovery of supraspinal control of stepping via indirect propriospinal relay connections after spinal cord injury," Nature Medicine, vol. 14, No. 1, (Jan. 6, 2008), 6 pages.
Cowley, K. et al., "Propriospinal neurons are sufficient for bulbospinal transmission of the locomotor command signal in the neonatal rat spinal cord," The Journal of Physiology, vol. 586, No. 6, Published Online Jan. 31, 2008, (Mar. 15, 2008), 13 pages.
Danner, S. et al., "Human spinal locomotor control is based on flexibly organized burst generators," Brain, vol. 138, No. 3, Available Online Jan. 12, 2015, Mar. 2015, 12 pages.
Danner, S. M. et al., "Body Position Influences Which neural structures are recruited by lumbar transcutaneous spinal cord stimulation", Plos One, vol. 11, No. 1, (2016), 13 pages.
Dimitrijevic, M. M. et al., "Clinical Elements for the Neuromuscular Stimulation and Functional Electrical Stimulation protocols in the Practice of Neurorehabilitation", Artificial Organs, vol. 26, No. 3, (2002), pp. 256-259.
Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004), 1 Page.
Drew, T. et al., "Cortical mechanisms involved in visuomotor coordination during precision walking," Brain Research Reviews, vol. 57, No. 1, Published Online Aug. 22, 2007, (Jan. 2007), 13 pages.
Duschau-Wicke, A. et al., "Patient-cooperative control increases active participation of individuals with SCI during robot-aided gait training," Journal of NeuroEngineering and Rehabilitation, vol. 7, No. 43, (Sep. 10, 2010), 13 pages.
Edgerton, V. et al., "Robotic Training and Spinal Cord Plasticity," Brain Research Bulletin, vol. 78, No. 1, Published Online Nov. 14, 2008, (Jan. 15, 2009), 19 pages.
Edgerton, V. et al., "Training Locomotor Networks," Brain Research Reviews, vol. 57, Published Online Sep. 16, 2007, (Jan. 2008), 25 pages.
European Office Action dated Jun. 9, 2022 in Application No. EP16825005.8.
Fleshman, J. et al., "Electronic Architecture of Type-Identified a-Motoneurons in the Cat Spinal Cord," Journal of Neurophysiology, vol. 60, No. 1, (Jul. 1, 1988), 26 pages.
Frey, M. et al., "A Novel Mechatronic Body Weight Support System," IEEE Transactions on Neural Systems and Rehabilitation Engineering, vol. 14, No. 3, (Sep. 18, 2006), 11 pages.
Fuentes, R. et al., "Spinal Cord Stimulation Restores Locomotion in Animal Models of Parkinson's Disease," Science, vol. 323, No. 5921, (Mar. 20, 2009), 14 pages.
Gerasimenko, Yu. P. et al., "Control of Locomotor Activity in Humans and Animals in the Absence of Supraspinal Influences", Neuroscience and Behavioral Physiology, vol. 32, No. 4, (2002), pp. 417-423.
Gerasimenko, Yu. P. et al., "Noninvasive Reactivation of Motor Descending Control after Paralysis", Journal of Neurotrauma, vol. 32, (2015), 13 pages.
Gilja, V. et al., "A high-performance neural prosthesis enabled by control algorithm design," Nature Neuroscience, vol. 15, No. 12, Published Online Nov. 18, 2012, (Dec. 2012), 56 pages.
Gittins, J. C., "Bandit Processes and Dynamic Allocation Indices", Journal of the Royal Statistical Society B, vol. 41, No. 2, (1979), pp. 148-164.

(56) References Cited

OTHER PUBLICATIONS

Guyatt, G. H. et al., "The 6-minute walk: a new measure of exercise capacity in patients with chronic heart failure," Canadian Medical Association Journal, vol. 132, No. 8, (Apr. 15, 1985), 5 pages.
Hagglund, M. et al., "Activation of groups of excitatory neurons in the mammalian spinal cord or hindbrain evokes locomotion," Nature Neuroscience, vol. 13, No. 2, Published Online Jan. 17, 2010, (Feb. 2010), 8 pages.
Harkema, S. et al., "Human Lumbosacral Spinal Cord Interprets Loading During Stepping," Journal of Neurophysiology, vol. 77, No. 2, (Feb. 1, 1997), 15 pages.
Harrison, P. et al., "Individual Excitatory Post-Synaptic Potentials Due to Muscle Spindle la Afferents in Cat Triceps Surae Motoneurones," The Journal of Physiology, vol. 312, No. 1, (Mar. 1981), pp. 455-470.
Hashtrudi-Zaad, K. et al., "On the Use of Local Force Feedback for Transparent Teleoperation," Proceedings of the 1999 IEEE International Conference on Robotics and Automation, (May 10, 1999), 7 pages.
Hennig, P. et al., "Entropy search for information-efficient global optimization" Journal of Machine Learning Research (JMLR), vol. 13, (Jun. 2012), pp. 1809-1837.
Hidler, J. et al., "ZeroG: Overground gait and balance training system," Journal of Rehabilitation Research & Development, vol. 48, No. 4, Available as Early as Jan. 1, 2011, (2011), 12 pages.
Hines, M. L. et al., "The Neuron Simulation Environment," Neural Computation, vol. 9, No. 6, (Aug. 15, 1997), 26 pages.
Hofstoetter, U. S. et al., "Effects of transcutaneous spinal cord stimulation on voluntary locomotor activity in an incomplete spinal cord injured individual", Biomed Tech, vol. 58 (Suppl. 1), (2013), 3 pages.
Hofstoetter, U. S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), 149 pages.
Hofstoetter, U. S. et al., "Modification of spasticity by transcutaneous spinal cord stimulation in individuals with incomplete spinal cord injury", The Journal of Spinal Cord Medicine, vol. 37, No. 2, (2014), pp. 202-211.
International Preliminary Report on Patentability dated Oct. 26, 2023, in Application No. PCT/US2022/024673.
International Search Report and Written Opinion dated Jun. 28, 2022, in PCT Application No. PCT/US2022/024673.
Ivanenko, Y. P. et al., "Temporal Components of the Motor Patterns Expressed by the Human Spinal Cord Reflect Foot Kinematics," Journal of Neurophysiology, vol. 90, No. 5, Nov. 2003, Published Online Jul. 9, 2003, (2003), 11 pages.
Jarosiewicz, B. et al., "Supplementary Materials for Virtual typing by people with tetraplegia using a self-calibrating intracortical brain-computer interface," Science Translational Medicine, vol. 7, No. 313, (Nov. 11, 2015), 26 pages.
Jarosiewicz, B. et al., "Virtual typing by people with tetraplegia using a self-calibrating intracortical brain-computer interface," Science Translational Medicine, vol. 7, No. 313, (Nov. 11, 2015), 11 pages.
Jilge, B. et al., "Initiating extension of the lower limbs in subjects with complete spinal cord injury by epidural lumbar cord stimulation", Exp Brain Res., vol. 154, (2004), pp. 308-326.
Johnson, W. L. et al., "Application of a Rat Hindlimb Model: A Prediction of Force Spaces Reachable Through Stimulation of Nerve Fascicles," IEEE Transactions on Bio-Medical Engineering, vol. 58, No. 12, Available Online Jan. 17, 2011, (Dec. 2011), 11 pages.
Jones, D. R. et al., "Efficient Global Optimization of Expensive Black-Box Functions", Journal of Global Optimization, vol. 13, (1998), pp. 455-492.
Jones, K. E. et al., "Computer Simulation of the Responses of Human Motoneurons to Composite 1A Epsps: Effects of Background Firing Rate," The Journal of Physiology, vol. 77, No. 1, (1997), 16 pages.
JP Office Action dated Aug. 21, 2023 in Application No. JP2021-510130 with English Translation.
JP Office Action dated Dec. 11, 2023 in JP Application No. 2019-539960 with English Translation.
JP Office Action dated Dec. 11, 2023, in JP Application No. 2023-10295 with English translation.
JP Office Action dated Feb. 17, 2023 in Application No. JP2019-539960 with English translation.
JP Office Action dated Jul. 18, 2023 in Application No. JP2021-509772 with English translation.
JP Office Action dated Sep. 4, 2023, in Application No. JP2021-188658 with English translation.
Kakulas, B., "A Review of the Neuropathology of Human Spinal Cord Injury with Emphasis on Special Features," Proceedings of the Donald Munro Memorial Lecture at the American Paraplegia Society 44th Annual Conference, Las Vegas, Nevada, (Sep. 9, 1998), 6 pages.
Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Published Online Jul. 17, 2000, (Aug. 1, 2000), 2 pages.
Kleinberg, R. et al., "Multi-armed bandits in metric spaces", In STOC, Computer and Automation Research Institute of the Hungarian Academy of Sciences, Budapest, Hungary, (2008), pp. 681-690.
Kocsis, L. et al. "Bandit Based Monte-Carlo Planning", European Conference on Machine Learning, Springer, Berlin, Heidelberg, (Sep. 2006), pp. 282-293.
Krassioukov, A. et al., "A Systematic Review of the Management of Autonomic Dysreflexia Following Spinal Cord Injury," Archives of Physical Medicine and Rehabilitation, vol. 90, No. 4, Apr. 2009, 27 pages.
Krassioukov, A. et al., "A Systematic Review of the Management of Orthostatic Hypotension Following Spinal Cord Injury," Archives of Physical Medicine and Rehabilitation, vol. 90, No. 5, May 2009, 22 pages.
Krause, A. et al. "Contextual Gaussian Process Bandit Optimization", In Advances in Neural Information Processing Systems (NIPS), (2011), 9 pages.
Krause, A. et al., "Near-optimal Nonmyopic Value of Information in Graphical Models", In UAI, (2005), 8 pages.
Krause, A. et al. "Near-Optimal Sensor Placements in Gaussian Processes: Theory, Efficient Algorithms and Empirical Studies", Journal of Machine Learning Research (JMLR), vol. 9, (Feb. 2008), pp. 235-284.
Kwakkel, G. et al., "Effects of Robot-assisted therapy on upper limb recovery after stroke: A Systematic Review," Neurorehabilitation and Neural Repair, vol. 22, No. 2, Published Online Sep. 17, 2007, (Mar. 2008), 11 pages.
Lavrov, I. et al., "Epidural Stimulation Induced Modulation of Spinal Locomotor Networks in Adult Spinal Rats," Journal of Neuroscience, vol. 28, No. 23, (Jun. 4, 2008), 8 pages.
Liu, J. et al., "Stimulation of the Parapyramidal Region of the Neonatal Rat Brain Stem Produces Locomotor-Like Activity Involving Spinal 5-HT7 and 5-HT2A Receptors", Journal of Neurophysiology, vol. 94, No. 2, Published Online May 4, 2005, (Aug. 1, 2005), 13 pages.
Lizotte, D. et al., "Automatic gait optimization with Gaussian process regression", In IJCAI, (2007), pp. 944-949.
Lovely, R. et al., "Effects of Training on the Recovery of Full-Weight-Bearing Stepping in the Adult Spinal Cat," Experimental Neurology, vol. 92, No. 2, (May 1986), 15 pages.
Lozano, A. et al., "Probing and Regulating Dysfunctional Circuits Using Deep Brain Stimulation," Neuron, vol. 77, No. 3, (Feb. 6, 2013), 19 pages.
McIntyre, C. C. et al., "Modeling the Excitability of Mammalian Nerve Fibers: Influence of Afterpotentials on the Recovery Cycle," Journal of Neurophysiology, vol. 87, No. 2, (Feb. 2002), 12 pages.

(56) References Cited

OTHER PUBLICATIONS

Minassian et al., "Mechanisms of rhythm generation of the human lumbar spinal cord in repose to tonic stimulation without and with step-related sensory feedback", Biomed Tech, vol. 58, (Suppl. 1), (2013), 3 pages.
Minassian, K. et al., "Human lumbar cord circuitries can be activated by extrinsic tonic input to generate locomotor-like activity", Human Movement Science, vol. 26, No. 2, (2007), pp. 275-295.
Minassian, K. et al., "Neuromodulation of lower limb motor control in restorative neurology", Clinical Neurology and Neurosurgery, vol. 114, (2012), pp. 489-497.
Minassian, K. et al., "Peripheral and Central Afferent Input to the Lumbar Cord", Biocybernetics and Biomedical Engineering, vol. 25, No. 3, (2005), pp. 11-29.
Minassian, K. et al., "Stepping-like movements in humans with complete spinal cord injury induced by epidural stimulation of the lumbar cord: electromyographic study of compound muscle action potentials", Spinal Cord, vol. 42, (2004), pp. 401-416.
Minev, I. R. et al., "Electronic dura mater for long-term multimodal neural interfaces," Science Magazine, vol. 347, No. 6218, (Jan. 9, 2015), 64 pages.
Minoux, M., Accelerated greedy algorithms for maximizing submodular set functions. Optimization Techniques, LNCS, (1978), pp. 234-243.
Moraud, E. et al., "Mechanisms Underlying the Neuromodulation of Spinal Circuits for Correcting Gait and Balance Deficits after Spinal Cord Injury," Neuron, vol. 89, No. 4, Feb. 17, 2016, Published Online Feb. 4, 2016, 15 pages.
Murg, M. et al., "Epidural electric stimulation of posterior structures of the human lumbar spinal cord: 1. Muscle twitches—a functional method to define the site of stimulation", Spinal Cord, vol. 38, (2000), pp. 394-402.
Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Published Online Jul. 24, 2009, (Nov. 2009), 5 pages.
Musienko, P. et al., "Controlling specific locomotor behaviors through multidimensional monoaminergic modulation of spinal circuitries," The Journal of Neuroscience, vol. 31, No. 25, (Jun. 22, 2011), 15 pages.
Musienko, P. et al. "Multi-system neurorehabilitative strategies to restore motor functions following severe spinal cord injury," Experimental Neurology, vol. 235, No. 1, Published Online Sep. 7, 2011, (May 2012), 10 pages.
Musselman, K. et al., "Spinal Cord Injury Functional Ambulation Profile: A New Measure of Walking Ability," Neurorehabilitation and Neural Repair, vol. 25, No. 3, Published Online Feb. 25, 2011, (Mar. 2011), 9 pages.
Nandra, M. S. et al., "A wireless microelectrode implant for spinal cord stimulation and recording in rats", Presentation Abstract, 2013, 104 Pages.
National Health Service., "Lumbar Decompression Surgery: When it's used", NHS, Apr. 28, 2022, https://www.nhs.uk/conditions/lumbar-decompression-surgery/why-its-done/#:- :text=Cauda%20equina%20syndrome%20is%20a,is%20severe%20or%20getting%20worse.
Nessler, J. et al., "A Robotic Device for Studying Rodent Locomotion After Spinal Cord Injury," IEEE Transactions on Neural Systems and Rehabilitation Engineering, vol. 13, No. 4, (Dec. 12, 2005), 10 pages.
Pearson, K. G., "Generating the walking gait: role of sensory feedback," Progress in Brain Research, vol. 143, Chapter 12, Published Online Nov. 28, 2003, (2004), 7 pages.
Phillips, A. et al., "Contemporary Cardiovascular Concerns after Spinal Cord Injury: Mechanisms, Maladaptations, and Management," Journal of Neurotrama, vol. 32, No. 24, Dec. 15, 2015, 17 pages.
Phillips, A. et al., "Perturbed and spontaneous regional cerebral blood flow responses to changes in blood pressure after high-level spinal cord injury: the effect of midodrine," Journal of Applied Physiology, vol. 116, No. 6, Mar. 15, 2014, Available Online Jan. 16, 2014, 9 pages.
Phillips, A. et al., "Regional neurovascular coupling and cognitive performance in those with low blood pressure secondary to high-level spinal cord injury: improved by alpha-1 agonist midodrine hydrochloride," Journal of Cerebral Blood Flow & Metabolism, vol. 34, No. 5, May 2014, 8 pages.
Pratt, G. et al., "Stiffness Isn't Everything," Proceedings of the Fourth International Symposium on Experimental Robotics, (Jun. 30, 1995), 6 pages.
Pratt, J. et al., "Series elastic actuators for high fidelity force control," Industrial Robot: An International Journal, vol. 29, No. 3, Available as Early as Jan. 1, 2002, 13 pages.
Prochazka, A. et al., "Ensemble firing of muscle afferents recorded during normal locomotion in cats," The Journal of Physiology, vol. 507, No. 1, (Feb. 15, 1998), 12 pages.
Prochazka, A. et al., "Models of ensemble filing of muscle spindle afferents recorded during normal locomotion in cats," The Journal of Physiology, vol. 507, No. 1, (Feb. 15, 1998), 15 pages.
Pudo, D. et al., "Estimating Intensity Fluctuations in High Repetition Rate Pulse Trains Generated Using the Temporal Talbot Effect", IEEE Photonics Technology Letters, vol. 18, No. 5, (Mar. 1, 2006), 3 pages.
Rasmussen, C. E. et al., "Gaussian Processes for Machine Learning (GPML) Toolbox", The Journal of Machine Learning Research, vol. 11, (2010), pp. 3011-3015.
Rasmussen, C. E. et al., "Gaussian Processes for Machine Learning", The MIT Press, Cambridge, Massachusetts, (2006), 266 pages.
Rasmussen, C. E. "Gaussian Processes in Machine Learning", L.N.A.I., vol. 3176, (2003) pp. 63-71.
Ratnovsky A. et al., "Mechanics of Respiratory Muscles," Respiratory Physiology & Neurobiology, 2008, vol. 163, pp. 82-89.
Rattay, F. et al., "Epidural electrical stimulation of posterior structures of the human lumbosacral cord: 2. Quantitative analysis by computer modeling", Spinal Cord, vol. 38, (2000), pp. 473-489.
Reinkensmeyer, D. et al., "Tools for understanding and optimizing robotic gait training," Journal of Rehabilitation Research & Development, vol. 43, No. 5, (Aug. 2006), 14 pages.
Rejc, E. et al., "Effects of Lumbosacral Spinal Cord Epidural Stimulation for Standing after Chronic Complete Paralysis in Humans," PLoS One, vol. 10, No. 7, (Jul. 24, 2015), 20 pages.
Robbins, H., "Some Aspects of the Sequential Design of Experiments", Bull. Amer. Math. Soc., vol. 58, (1952), pp. 527-535.
Rosenzweig, E. et al., "Extensive Spontaneous Plasticity of Corticospinal Projections After Primate Spinal Cord Injury", Nature Neuroscience, vol. 13, No. 12, Published Online Nov. 14, 2010, (Dec. 2010), 19 pages.
Ryzhov, I. O. et al., "The knowledge gradient algorithm for a general class of online learning problems", Operations Research, vol. 60, No. 1, (2012), pp. 180-195.
Sayenko, D. et al., "Neuromodulation of evoked muscle potentials induced by epidural spinal-cord stimulation in paralyzed individuals," Journal of Neurophysiology, vol. 111, No. 5, Published Online Dec. 11, 2013, (2014), 12 pages.
Shamir, R. R. et al., "Machine Learning Approach to Optimizing Combined Stimulation and Medication Therapies for Parkinson's Disease," Brain Stimulation, vol. 8, No. 6, Published Online Jun. 15, 2015, (Nov. 2015), 22 pages.
Srinivas, N. et al., "Gaussian process optimization in the bandit setting: No. regret and experimental design", In Proceedings of the 27th International Conference on Machine Learning, (2010), 17 pages.
Steward, O. et al., "False Resurrections: Distinguishing Regenerated from Spared Axons in the Injured Central Nervous System", The Journal of Comparative Neurology, vol. 459, No. 1, (Apr. 21, 2003), 8 pages.
Stienen, A. H. A. et al., "Analysis of reflex modulation with a biologically realistic neural network," Journal of Computer Neuroscience, vol. 23, No. 3, Available Online May 15, 2007, (Dec. 2007), 16 pages.

(56) References Cited

OTHER PUBLICATIONS

Sun, F. et al., "Sustained axon regeneration induced by co-deletion of PTEN and SOCS3", Nature, vol. 480, No. 7377, Published Online Nov. 6, 2011, (Dec. 15, 2011), 12 pages.
Takeoka, A. et al., "Muscle Spindle Feedback Directs Locomotor Recovery and Circuit Reorganization after Spinal Cord Injury", Cell, vol. 159, No. 7, (Dec. 18, 2014), 27 pages.
Tenne, Y. et al., "Computational Intelligence in Expensive Optimization Problems", vol. 2 of Adaptation, Learning, and Optimization, Springer, Berlin Heidelberg, (2010), pp. 131-162.
Timozyk, W. et al., "Hindlimb loading determines stepping quantity and quality following spinal cord transection," Brain Research, vol. 1050, No. 1-2, Published Online Jun. 24, 2005, (Jul. 19, 2005), 10 pages.
U.S. Final Office Action dated Apr. 6, 2023 in U.S. Appl. No. 16/615,765.
U.S. Final Office Action dated Jun. 1, 2023 in U.S. Appl. No. 16/479,201.
U.S. Final Office Action dated Nov. 28, 2023 in U.S. Appl. No. 17/270,402.
U.S. Non-Final Office Action dated Apr. 28, 2023, in U.S. Appl. No. 17/270,402.
U.S. Non-Final Office Action dated Aug. 16, 2023, in U.S. Appl. No. 17/269,970.
U.S. Non-Final Office Action dated Sep. 13, 2023, in U.S. Appl. No. 17/407,043.
Vallery, H. et al., "Compliant Actuation of Rehabilitation Robots," IEEE Robotics & Automation Magazine, vol. 15, No. 3, (Sep. 12, 2008), 10 pages.
Van Den Brand, R. et al., "Restoring Voluntary Control of Locomotion after Paralyzing Spinal Cord Injury," Science Magazine, vol. 336, No. 6085, (Jun. 1, 2012), 5 pages.
Wan, D. et al., "Life-threatening outcomes associated with autonomic dysreflexia: A clinical review," Journal of Spinal Cord Medicine, vol. 37, No. 1, (Jan. 2014), 9 pages.
Wenger, N. et al. "Closed-loop neuromodulation of spinal sensorimotor circuits controls refined locomotion after complete spinal cord injury" Sci Transl Med. Sep. 2, 20144, vol. 6, Issue 255, (10 pages).
Wenger, N. et al., "Spatiotemporal neuromodulation therapies engaging muscle synergies improve motor control after spinal cord injury," Natural Medicine, vol. 22, No. 2, Available Online Jan. 18, 2016, (Feb. 2016), 33 pages.
Wenger, N. et al., "Supplementary Materials for Closed-loop neuromodulation of spinal sensorimotor circuits controls refined locomotion after complete spinal cord injury," Science Translational Medicine, vol. 6, No. 255, Sep. 24, 2014, 14 pages.
Wernig, A. et al., "Laufband locomotion with body weight support improved walking in persons with severe spinal cord injuries", Paraplegia, vol. 30, No. 4, (Apr. 1992), 10 pages.
Wernig, A., "Ineffectiveness of Automated Locomotor Training," Archives of Physical Medicine and Rehabilitation, vol. 86, No. 12, (Dec. 2005), 2 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, (Jun. 2010), 7 pages.
Widmer, C. et al., Inferring latent task structure for multitask learning by multiple kernel learning, BMC Bioinformatics, vol. 11, (Suppl 8:S5), (2010), 8 pages.
Winter, D. A. et al., "An integrated EMG/biomechanical model of upper body balance and posture during human gait," Progress in Brain Research, vol. 97, Ch. 32, Available as Early as Jan. 1, 1993, (1993), 9 pages.
Wirz, M. et al., "Effectiveness of automated locomotor training in patients with acute incomplete spinal cord injury: A randomized controlled multicenter trial," BMC Neurology, vol. 11, No. 60, (May 27, 2011), 9 pages.
Yakovenko, S. et al., "Spatiotemporal Activation of Lumbosacral Motoneurons in the Locomotor Step Cycle," Journal of Neurophysiology, vol. 87, No. 3, (Mar. 2002), 12 pages.
Zhang, T. C. et al., "Mechanisms and models of spinal cord stimulation for the treatment of neuropathic pain," Brain Research, vol. 1569, Published Online May 4, 2014, (Jun. 20, 2014), 13 pages.
Zorner, B. et al., "Profiling locomotor recovery: comprehensive quantification of impairments after CNS damage in rodents," Nature Methods, vol. 7, No. 9, Published Online Aug. 15, 2010, (Sep. 2010), 11 pages.
Office Action in Canadian Application No. 3,030,615; received on Feb. 18, 2026.
Extended European Search Report in European Application No. 25221547.0; received on Feb. 20, 2026.

* cited by examiner

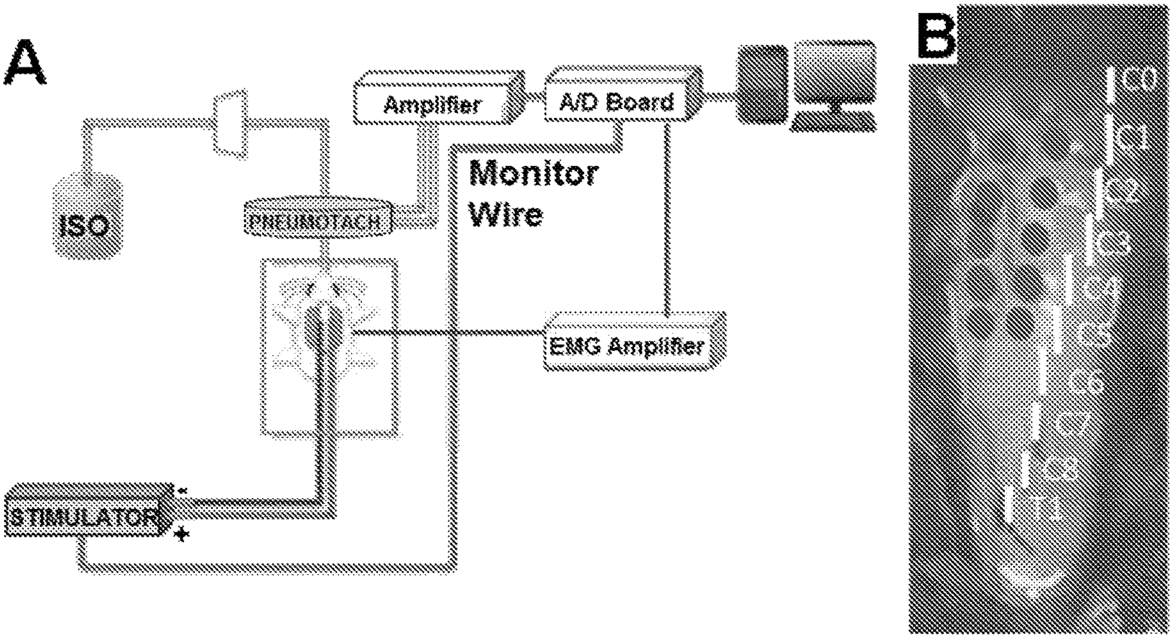
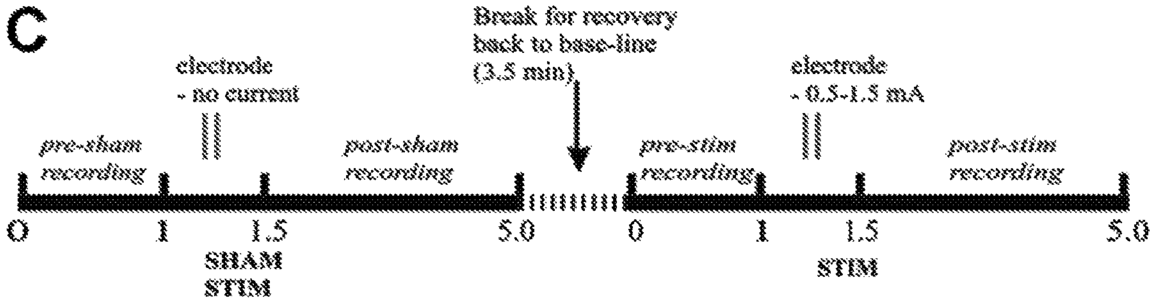
*Fig. 5*

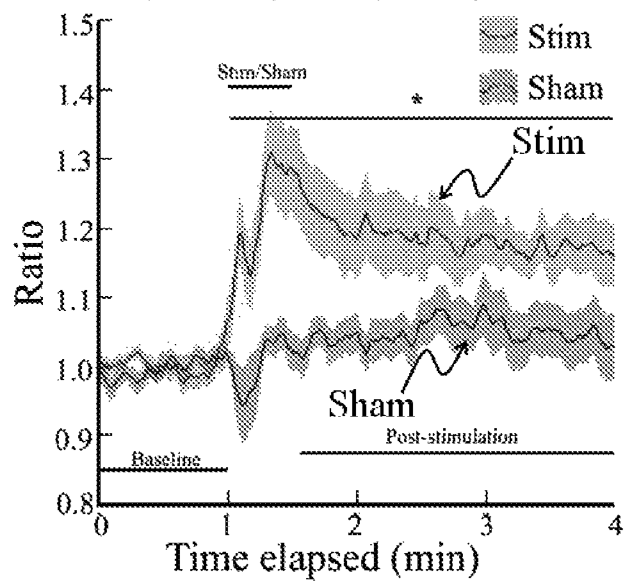
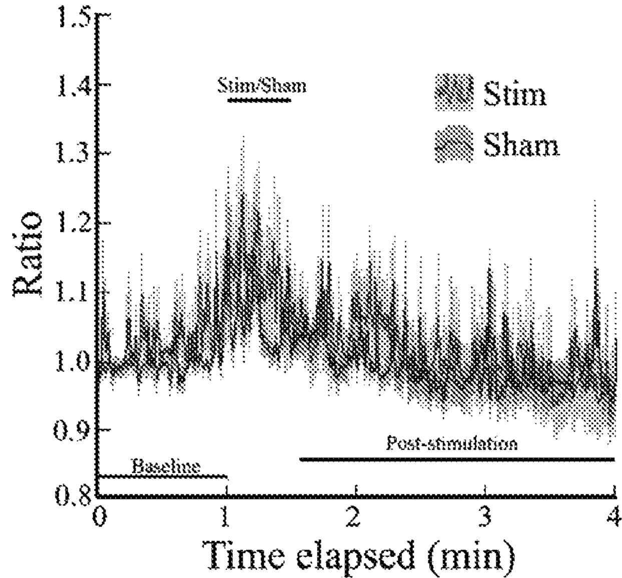
*Fig. 7*

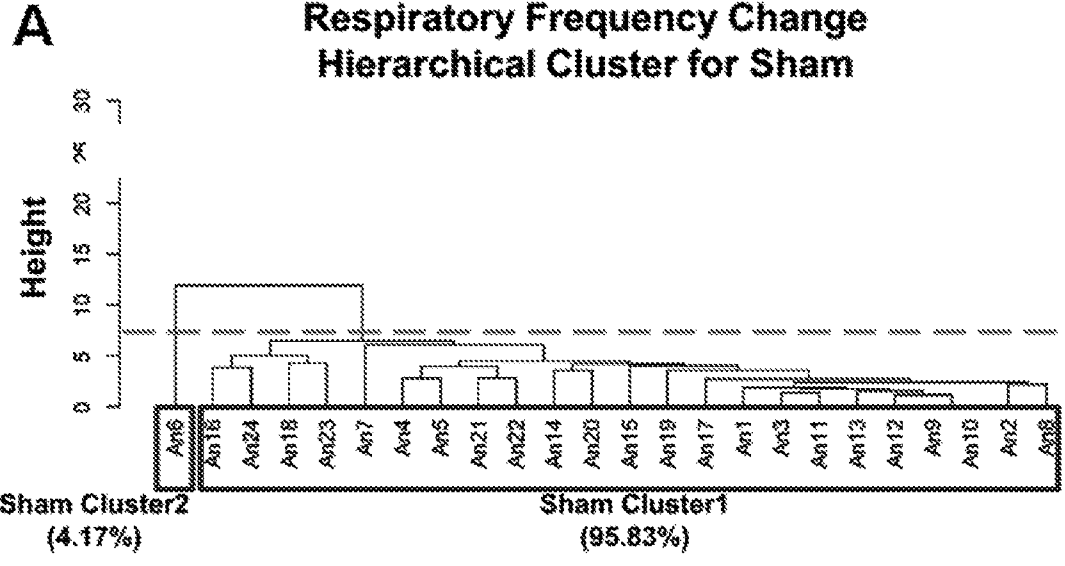
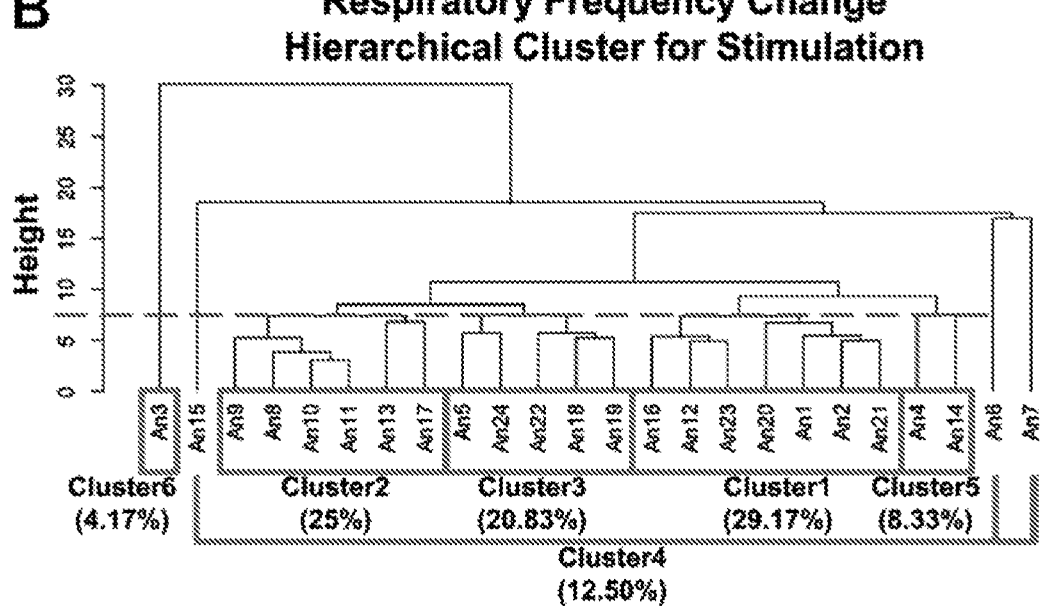
*Fig. 8*

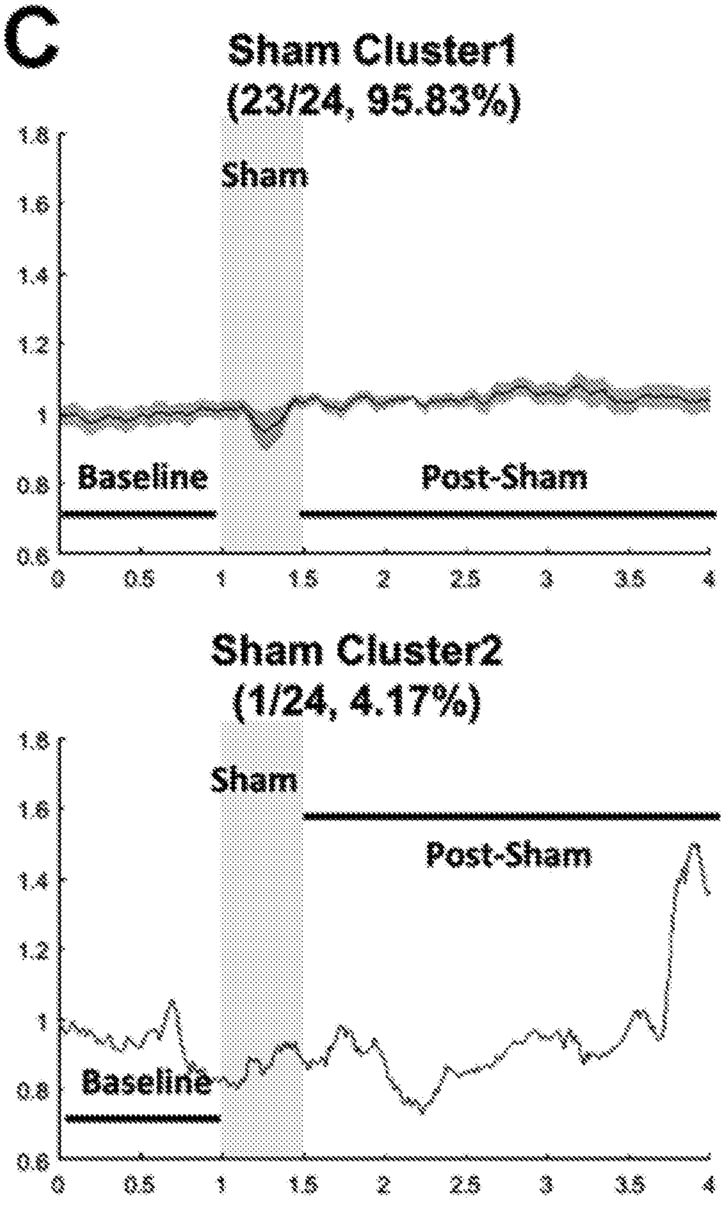
*Fig. 8, cont'd.*

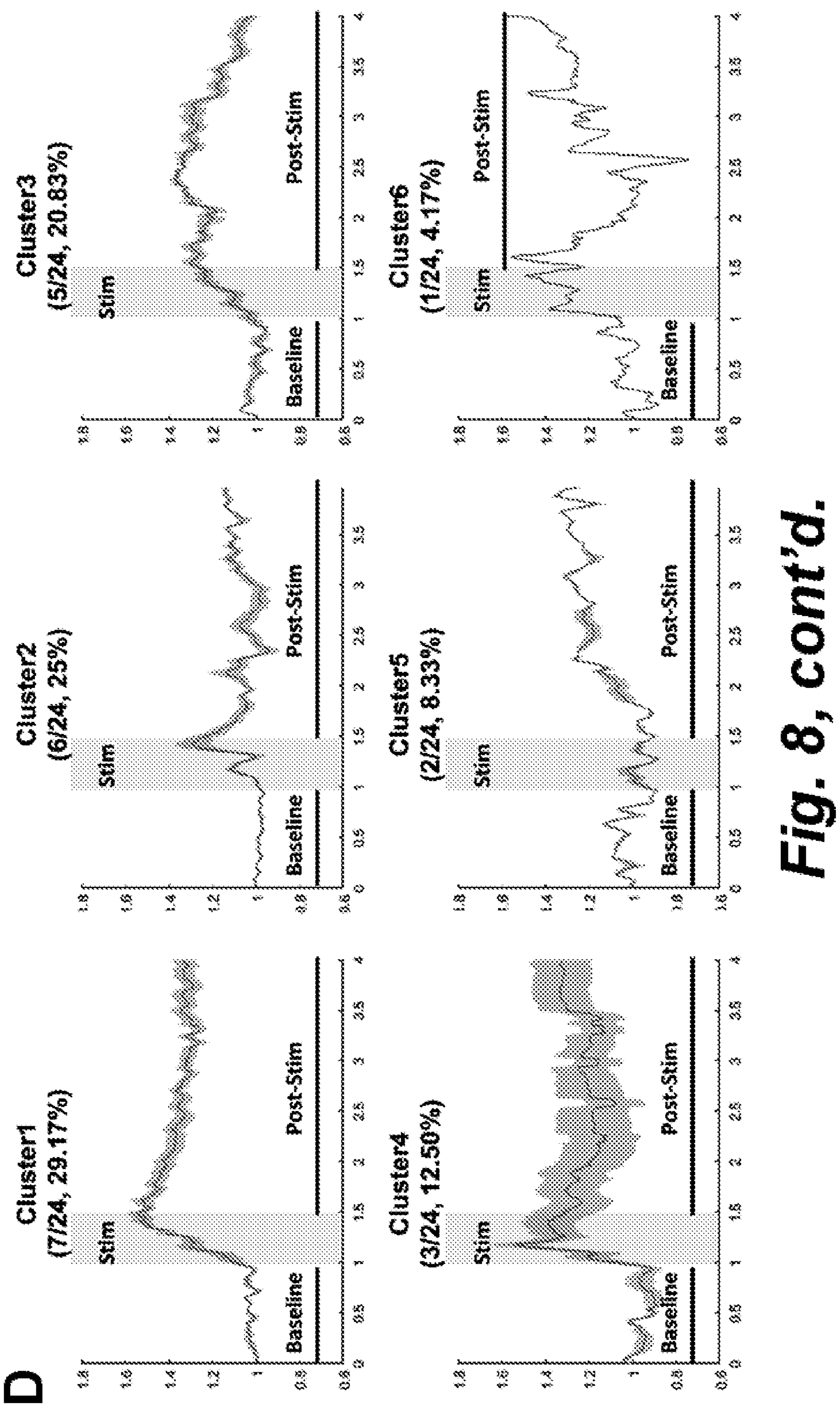
*Fig. 8, cont'd.*

*Fig. 9, cont'd.*

| Sigh Pattern | Eupnea Pattern |
| --- | --- |
| Stim \| Post-stim<br>No Change \| No Change<br>#1, #2, #9, #13, #14, #21 | Stim \| Post-stim<br>No Change \| No Change |
| Stim \| Post-stim<br>No Change \| Increase<br>#4, #6, #7, #22, #23, #24 | Stim \| Post-stim<br>No Change \| Increase<br>#3, #4, #5, #14, #18, #19, #22, #24 |
| Stim \| Post-stim<br>Increase \| No Change<br>#5, #10, #11, #12 | Stim \| Post-stim<br>Increase \| No Change<br>#8, #9, #10, #11, #13, #17 |
| Stim \| Post-stim<br>Increase \| Increase<br>#3, #8, #15, #16, #17, #18, #19, #20 | Stim \| Post-stim<br>Increase \| Increase<br>#1, #2, #6, #7, #12, #15, #16, #20, #21, #23 |

*Fig. 10*

ACCESSING SPINAL NETWORK TO ENABLE RESPIRATORY FUNCTION

CROSS-REFERENCE TO RELATED APPLICATIONS

This application is a U.S. 371 National Phase of PCT/US2016/041802, filed Jul. 11, 2016, which claims benefit of and priority to U.S. Ser. No. 62/191,892, filed on Jul. 13, 2015, both of which are incorporated herein by reference in their entirety for all purposes.

STATEMENT OF GOVERNMENTAL SUPPORT

[Not Applicable]

BACKGROUND

Trauma, disease, infection, drugs, and other factors can diminish the human body's ability to breathe and in such instances, it is difficult to mechanically mimic the human body's method of respiration.

Respiration or breathing involves a complex network of circuits that is involved in central pattern generation (CPG) that spans the brainstem and cervical spinal cord to generate a respiratory rhythm. Sensory input from central and peripheral chemoreceptors (e.g., $CO_2$ receptors), lung stretch receptors naturally influence the firing pattern of the CPG. In the disease or injury state to the brainstem or spinal cord, the respiratory rhythm is compromised, likely due to the depressed state of the CPG. Current technology in addressing the depressed respiratory state is to stimulate the diaphragm muscle which actively participates in inspiration by phrenic nerve stimulators. The issue with this approach is that the muscle will not react to changes in the activity state of the patient and only activates the diaphragm which participates in the inspiratory phase of respiration.

Definitions

As used herein "electrical stimulation" or "stimulation" means application of an electrical signal that may be either excitatory or inhibitory to a muscle or neuron and/or to groups of neurons and/or interneurons. It will be understood that an electrical signal may be applied to one or more electrodes with one or more return electrodes.

As used herein "magnetic stimulation" or means use of a varying magnetic field to induce an electrical signal, e.g., in a neuron, that may be either excitatory or inhibitory to a muscle or neuron and/or to groups of neurons and/or interneurons. It will be understood that an electrical signal may be applied to one or more electrodes with one or more return electrodes.

As used herein "epidural" means situated upon the dura or in very close proximity to the dura. The term "epidural stimulation" refers to electrical epidural stimulation.

The term "transcutaneous stimulation" or "transcutaneous electrical stimulation" or "cutaneous electrical stimulation" refers to electrical stimulation applied to the skin, and, as typically used herein refers to electrical stimulation applied to the skin in order to effect stimulation of the spinal cord or a region thereof. The term "transcutaneous electrical spinal cord stimulation" may also be referred to as "tSCS". The term "pcEmc" refers to painless cutaneous electrical stimulation.

The term "motor complete" when used with respect to a spinal cord injury indicates that there is no motor function below the lesion, (e.g., no movement can be voluntarily induced in muscles innervated by spinal segments below the spinal lesion.

The term "monopolar stimulation" refers to stimulation between a local electrode and a common distant return electrode.

The term "co-administering", "concurrent administration", "administering in conjunction with" or "administering in combination" when used, for example with respect to transcutaneous electrical stimulation, epidural electrical stimulation, and pharmaceutical administration, refers to administration of the transcutaneous electrical stimulation and/or epidural electrical stimulation and/or pharmaceutical such that various modalities can simultaneously achieve a physiological effect on the subject. The administered modalities need not be administered together, either temporally or at the same site. In some embodiments, the various "treatment" modalities are administered at different times. In some embodiments, administration of one can precede administration of the other (e.g., drug before electrical and/or magnetic stimulation or vice versa). Simultaneous physiological effect need not necessarily require presence of drug and the electrical and/or magnetic stimulation at the same time or the presence of both stimulation modalities at the same time. In some embodiments, all the modalities are administered essentially simultaneously.

The phrase "spinal cord stimulation" as used herein includes stimulation of any spinal nervous tissue, including spinal neurons, accessory neuronal cells, nerves, nerve roots, nerve fibers, or tissues, that are associated with the spinal cord. It is contemplated that spinal cord stimulation may comprise stimulation of one or more areas associated with a cervical vertebral segment.

As used herein, "spinal nervous tissue" refers to nerves, neurons, neuroglial cells, glial cells, neuronal accessory cells, nerve roots, nerve fibers, nerve rootlets, parts of nerves, nerve bundles, mixed nerves, sensory fibers, motor fibers, dorsal root, ventral root, dorsal root ganglion, spinal ganglion, ventral motor root, general somatic afferent fibers, general visceral afferent fibers, general somatic efferent fibers, general visceral efferent fibers, grey matter, white matter, the dorsal column, the lateral column, and/or the ventral column associated with the spinal cord. Spinal nervous tissue includes "spinal nerve roots," that comprise any one or more of the 31 pairs of nerves that emerge from the spinal cord. Spinal nerve roots may be cervical nerve roots, thoracic nerve roots, and lumbar nerve roots.

SUMMARY

In various embodiments, methods are provided for applying spinal cord stimulation with and without selective pharmaceuticals to enable respiratory function in subjects whose ability to breath has been compromised. The spinal cord stimulation can be transcutaneous and/or epidural electrical stimulation and/or magnetic stimulation. In various embodiments the electrical stimulation alone or in combination with pharmaceuticals can be applied to facilitate restoration of normal breathing patterns.

Various embodiments contemplated herein may include, but need not be limited to, one or more of the following:

Embodiment 1

A method of improving, and/or regulating, and/or restoring respiration in a subject with a respiratory deficiency, said method comprising: neuromodulating the cervical spinal cord of said subject by administering transcutaneous stimulation to the cervical spinal cord or a region thereof at a frequency and intensity sufficient to regulate and/or to restore respiration; and/or neuromodulating the cervical spinal cord of said subject by administering epidural stimulation to the cervical spinal cord or a region thereof at a frequency and intensity sufficient to regulate and/or to restore respiration; and/or neuromodulating the cervical spinal cord of said subject with a magnetic stimulator at a frequency and intensity sufficient to regulate and/or to restore respiration.

Embodiment 2

The method of embodiment 1, wherein said method comprises administering transcutaneous stimulation to the cervical spinal cord or a region thereof.

Embodiment 3

The method of embodiment 2, wherein said transcutaneous stimulation is at a frequency of at least about 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz, or at least about 1 kHz, or at least about 1.5 kHz, or at least about 2 kHz, or at least about 2.5 kHz, or at least about 5 kHz, or at least about 10 kHz, or up to about 25 kHz, or up to about 50 kHz, or up to about 100 kHz.

Embodiment 4

The method of embodiment 2, wherein said transcutaneous stimulation is at a frequency ranging from about 1 Hz, or from about 2 Hz, or from about 3 Hz, or from about 4 Hz, or from about 5 Hz, or from about 10 Hz, or from about 10 Hz, or from about 10 Hz, up to about 500 Hz, or up to about 400 Hz, or up to about 300 Hz, or up to about 200 Hz up to about 100 Hz, or up to about 90 Hz, or up to about 80 Hz, or up to about 60 Hz, or up to about 40 Hz, or from about 3 Hz or from about 5 Hz up to about 80 Hz, or from about 5 Hz to about 60 Hz, or up to about 30 Hz.

Embodiment 5

The method of embodiment 2, wherein said transcutaneous stimulation is at a frequency ranging from about 20 Hz or about 30 Hz to about 90 Hz or to about 100 Hz, to initiate respiration when no respiration pattern is present.

Embodiment 6

The method of embodiment 2, wherein said transcutaneous stimulation is at a frequency ranging from about 5 Hz or about 10 Hz up to about 90 Hz or about 100 Hz, when a respiration pattern is present.

Embodiment 7

The method according to any one of embodiments 2-4, wherein said transcutaneous stimulation is at an intensity ranging from about 5 mA or about 10 mA up to about 500 mA, or from about 5 mA or about 10 mA up to about 400 mA, or from about 5 mA or about 10 mA up to about 300 mA, or from about 5 mA or about 10 mA up to about 200 mA, or from about 5 mA or about 10 mA to up about 150 mA, or from about 5 mA or about 10 mA up to about 50 mA, or from about 5 mA or about 10 mA up to about 100 mA, or from about 5 mA or about 10 mA up to about 80 mA, or from about 5 mA or about 10 mA up to about 60 mA, or from about 5 mA or about 10 mA up to about 50 mA.

Embodiment 8

The method according to any one of embodiments 2-7, wherein transcutaneous stimulation comprises administering pulses having a width that ranges from about 100 μs up to about 1 ms or up to about 800 μs, or up to about 600 μs, or up to about 500 μs, or up to about 400 μs, or up to about 300 μs, or up to about 200 μs, or up to about 100 μs, or from about 150 μs up to about 600 μs, or from about 200 μs up to about 500 μs, or from about 200 μs up to about 400 μs.

Embodiment 9

The method according to any one of embodiments 2-8, wherein said transcutaneous stimulation is at a frequency, pulse width, and amplitude sufficient to restore a resting respiration rate and at least 60%, or at least 70%, or at least 80%, or at least 90% of the subjects normal tidal volume.

Embodiment 10

The method according to any one of embodiments 2-9, wherein said transcutaneous stimulation is superimposed on a high frequency carrier signal.

Embodiment 11

The method of embodiment 10, wherein said high frequency carrier signal ranges from about 3 kHz, or about 5 kHz, or about 8 kHz up to about 30 kHz, or up to about 20 kHz, or up to about 15 kHz.

Embodiment 12

The method of embodiment 10, wherein said high frequency carrier signal is about 10 kHz.

Embodiment 13

The method according to any one of embodiments 10-12, wherein said carrier frequency amplitude ranges from about 30 mA, or about 40 mA, or about 50 mA, or about 60 mA, or about 70 mA, or about 80 mA up to about 300 mA, or up to about 200 mA, or up to about 150 mA.

Embodiment 14

The method of embodiment 1, wherein said method comprises administering epidural stimulation to the cervical spinal cord or a region thereof.

Embodiment 15

The method of embodiment 14, wherein said epidural stimulation is at a frequency of at least about 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz, or at least about 1 kHz, or at least about 1.5 kHz, or at least about 2 kHz, or at least about 2.5 kHz, or at least about 5 kHz, or at least about 10 kHz, or up to about 25 kHz, or up to about 50 kHz, or up to about 100 kHz.

Embodiment 16

The method of embodiment 14, wherein said epidural stimulation is at a frequency ranging from about 1 Hz, or from about 2 Hz, or from about 3 Hz, or from about 4 Hz, or from about 5 Hz, or from about 10 Hz, or from about 15 Hz, or from about 30 Hz, up to about 500 Hz, or up to about 400 Hz, or up to about 300 Hz, or up to about 200 Hz up to about 100 Hz, or up to about 90 Hz, or up to about 80 Hz, or up to about 60 Hz, or up to about 40 Hz, or up to about 35 Hz, or up to about 30 Hz, or from about 3 Hz or from about 5 Hz up to about 80 Hz, or from about 5 Hz to about 60 Hz, or up to about 30 Hz.

Embodiment 17

The method of embodiment 14, wherein said epidural stimulation is at a frequency ranging from about 20 Hz or about 30 Hz to about 90 Hz or to about 100 Hz, to initiate respiration when no respiration pattern is present.

Embodiment 18

The method of embodiment 14, wherein said epidural stimulation is at a frequency ranging from about 5 Hz or about 10 Hz up to about 90 Hz or about 100 Hz, when a respiration pattern is present.

Embodiment 19

The method according to any one of embodiments 14-18, wherein said epidural stimulation is at an amplitude ranging from 0.5 mA, or from about 1 mA, or from about 2 mA, or from about 3 mA, or from about 4 mA, or from about 5 mA up to about 50 mA, or up to about 30 mA, or up to about 20 mA, or up to about 15 mA, or from about 5 mA to about 20 mA, or from about 5 mA up to about 15 mA.

Embodiment 20

The method according to any one of embodiments 14-19, wherein stimulation comprises pulsing having a pulse width that ranges from about 100 μs up to about 1 ms or up to about 800 μs, or up to about 600 μs, or up to about 500 μs, or up to about 400 μs, or up to about 300 μs, or up to about 200 μs, or up to about 100 μs, or from about 150 μs up to about 600 μs, or from about 200 μs up to about 500 μs, or from about 200 μs up to about 400 μs.

Embodiment 21

The method according to any one of embodiments 14-20, wherein said epidermal stimulation is at a frequency, pulse width, and amplitude sufficient to restore a resting respiration rate and at least 60%, or at least 70%, or at least 80%, or at least 90% of the subjects normal tidal volume.

Embodiment 22

The method according to any one of embodiments 14-21, wherein said epidural stimulation is applied paraspinally over one or more cervical vertebrae.

Embodiment 23

The method according to any one of embodiments 14-21, wherein said epidural stimulation is applied at a region comprising C2-C3 or a region therein.

Embodiment 24

The method of embodiment 23, wherein said stimulation is applied at C3.

Embodiment 25

The method according to any one of embodiments 23-24, wherein said epidural stimulation is applied to the dorsal (posterior) column.

Embodiment 26

The method of embodiment 25, wherein said epidural stimulation is applied to the lateral portion of said dorsal (posterior) column.

Embodiment 27

The method according to any one of embodiments 23-26, wherein epidural stimulation is applied to a dorsal root.

Embodiment 28

The method of embodiment 27, wherein epidural stimulation is applied to a dorsal root at the point of entry.

Embodiment 29

The method according to any one of embodiments 23-28, wherein epidural stimulation is applied to a ventral (anterior) column.

Embodiment 30

The method of embodiment 29, wherein said epidural stimulation is applied to a lateral portion of said column.

Embodiment 31

The method according to any one of embodiments 23-30, wherein epidural stimulation is applied to a ventral root.

Embodiment 32

The method of embodiment 31, wherein said epidural stimulation is applied to a ventral root at the point of entry.

Embodiment 33

The method according to any one of embodiments 29-32, wherein said epidural stimulation to a ventral column and/or a ventral root speeds up respiration in a subject that is already breathing.

Embodiment 34

The method according to any one of embodiments 14-33, wherein said epidural stimulation is not applied to a medial portion of a dorsal column.

Embodiment 35

The method according to any one of embodiments 14-34, wherein said epidural stimulation is applied via a permanently implanted electrode array.

Embodiment 36

The method of embodiment 35, wherein said electrode array comprises a plurality of electrodes disposed on a flexible backing.

Embodiment 37

The method of embodiment 36, wherein said electrode array provides at least 2 channels, or at least 4 channels, or at least 8 channels, or at least 12 channels, or at least 16 channels, or at least 20 channels, or at least 24 channels, or at least 28 channels, or at least 32 channels, or at least 36 channels, or at least 40 channels, or at least 40 channels, or at least 48 channels, or at least 52 channels, or at least 56 channels, or at least 60 channels, or at least or 64 channels.

Embodiment 38

The method according to any one of embodiments 36-37, wherein said electrode array comprises a plurality of electrodes disposed on a backing comprising parylene or silicon.

Embodiment 39

The method according to any one of embodiments 36-37, wherein said electrode array is a parylene based microelectrode implant.

Embodiment 40

The method according to any one of embodiments 35-39, wherein said electrode array has a configuration that is a 32 channel dorsal respiration electrode type A.

Embodiment 41

The method according to any one of embodiments 35-39, wherein said electrode array has a configuration that is a 48 channel dorsal respiration electrode type B.

Embodiment 42

The method according to any one of embodiments 35-39, wherein said electrode array has a configuration that is an 8 channel ventral respiration dual electrode type C having an inferolateral exiting electrode tail.

Embodiment 43

The method of embodiment 1, wherein said method comprises administering magnetic neural stimulation to the cervical spinal cord or a region thereof.

Embodiment 44

The method of embodiment 43, wherein said stimulation is monophasic.

Embodiment 45

The method of embodiment 43, wherein said stimulation is biphasic.

Embodiment 46

The method of embodiment 43, wherein said stimulation is polyphasic.

Embodiment 47

The method according to any one of embodiments 43-46, wherein said magnetic stimulation produces a magnetic field of at least 1 tesla, or at least 2 tesla, or at least 3 tesla, or at least 4 tesla.

Embodiment 48

The method according to any one of embodiments 43-47, wherein said magnetic stimulation is at a frequency of at least about 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz.

Embodiment 49

The method according to any one of embodiments 43-47, wherein said magnetic stimulation is at a frequency ranging from about 1 Hz, or from about 2 Hz, or from about 3 Hz, or from about 4 Hz, or from about 5 Hz, or from about 10 Hz, or from about 10 Hz, or from about 10 Hz, up to about 500 Hz, or up to about 400 Hz, or up to about 300 Hz, or up to about 200 Hz up to about 100 Hz, or up to about 90 Hz, or up to about 80 Hz, or up to about 60 Hz, or up to about 40 Hz, or from about 3 Hz or from about 5 Hz up to about 80 Hz, or from about 5 Hz to about 60 Hz, or up to about 30 Hz.

Embodiment 50

The method according to any one of embodiments 43-47, wherein said magnetic stimulation is at a frequency ranging from about 20 Hz or about 30 Hz to about 90 Hz or to about 100 Hz, to initiate respiration when no respiration pattern is present.

Embodiment 51

The method according to any one of embodiments 43-47, wherein said magnetic stimulation is at a frequency ranging from about 5 Hz or about 10 Hz up to about 90 Hz or about 100 Hz, when a respiration pattern is present.

Embodiment 52

The method according to any one of embodiments 43-48, wherein said magnetic stimulation is applied using a single coil stimulator.

Embodiment 53

The method according to any one of embodiments 43-48, wherein said magnetic stimulation is applied using a double coil stimulator.

Embodiment 54

The method according to any one of embodiments 43-53, wherein said magnetic stimulation is at a frequency, amplitude, and orientation sufficient to restore a resting respiration rate and at least 60%, or at least 70%, or at least 80%, or at least 90% of the subjects normal tidal volume.

Embodiment 55

The method according to any one of embodiments 1-54, wherein said stimulation is applied to a region spanning no more than five cervical vertebrae, or over a region spanning no more than four cervical vertebrae, or over a region spanning no more than three cervical vertebrae, or over a region spanning no more than two cervical vertebrae, or over a region spanning no more than one cervical vertebrae.

Embodiment 56

The method according to any one of embodiments 1-55, wherein said stimulation is applied to a region ranging from C0 (suboccipital) to C8, or to a region ranging from about C0 to C7, or to a region ranging from about C0 to C6, or to a region ranging from about C1 to C6, or to a region ranging from about C2 to C5, or to a region ranging from about C3 to C4.

Embodiment 57

The method according to any one of embodiments 1-56, wherein said stimulation is applied via an implantable stimulator.

Embodiment 58

The method according to any one of embodiments 1-56, wherein said stimulation is applied via an external stimulator.

Embodiment 59

The method according to any one of embodiments 57-58, wherein said stimulator is configured to alter a stimulation pattern in response to respiration rate and/or tidal volume.

Embodiment 60

The method according to any one of embodiments 57-59, wherein said stimulator is configured to alter a stimulation pattern in response to heart rate.

Embodiment 61

The method according to any one of embodiments 1-60, wherein said subject is a human.

Embodiment 62

The method according to any one of embodiments 1-60, wherein said subject is a non-human mammal.

Embodiment 63

The method according to any one of embodiments 1-62, wherein respiratory deficiency is due to a spinal cord injury.

Embodiment 64

The method of embodiment 63, wherein said spinal cord injury is clinically classified as motor complete.

Embodiment 65

The method of embodiment 63, wherein said spinal cord injury is clinically classified as motor incomplete.

Embodiment 66

The method according to any one of embodiments 1-62, wherein said respiratory deficiency is due to an ischemic brain injury.

Embodiment 67

The method of embodiment 66, wherein said ischemic brain injury is brain injury from stroke or acute trauma.

Embodiment 68

The method according to any one of embodiments 1-62, wherein said respiratory deficiency is due to a neurodegenerative disorder.

Embodiment 69

The method of embodiment 68, wherein said neurodegenerative disorder is associated with a condition selected from the group consisting of Parkinson's disease, Huntington's disease, Alzheimer's disease, amyotrophic lateral sclerosis (ALS), primary lateral sclerosis (PLS), dystonia, and cerebral palsy.

Embodiment 70

The method according to any one of embodiments 1-62, wherein said subject is at risk for sudden infant death syndrome (SIDS).

Embodiment 71

The method according to any one of embodiments 1-62, wherein said subject is in intensive care unit patient with decreased respiratory drive.

Embodiment 72

The method according to any one of embodiments 1-62, wherein said respiratory deficiency is acute respiratory distress syndrome (ARDS), or acute respiratory failure.

Embodiment 73

The method according to any one of embodiments 1-62, wherein said respiratory deficiency is due to alcohol intoxication and/or a drug overdose.

Embodiment 74

The method of embodiment 73, wherein said respiratory deficiency is due to a drug overdose.

Embodiment 75

The method according to any one of embodiments 1-69, and 71-74, wherein the stimulation is under control of the subject.

Embodiment 76

The method according to any one of embodiments 1-74, wherein the stimulation is under control medical care personnel.

Embodiment 77

The method according to any one of embodiments 1-76, wherein said method further comprises administering at least one monoaminergic agonist to said subject.

Embodiment 78

The method of embodiment 77, wherein said at least one monoaminergic agonist comprises an agent selected from the group consisting of a serotonergic drug, a dopaminergic drug, a noradrenergic drug, a GABAergic drug, and a glycinergic drug.

Embodiment 79

The method of embodiment 78, wherein said agent is selected from the group consisting of 8-hydroxy-2-(di-n-propylamino)tetralin (8-OH-DPAT), 4-(benzodioxan-5-yl)1-(indan-2-yl)piperazine (S15535), N-{2-[4-(2-methoxyphenyl)-1-piperazinyl]ethyl}-N-(2-pyridinyl)cyclohexanecarboxamide (WAY 100.635), Quipazine, Ketanserin, 4-amino-(6-chloro-2-pyridyl)-1 piperidine hydrochloride (SR 57227A), Ondanesetron, Buspirone, Methoxamine, Prazosin, Clonidine, Yohimbine, 6-chloro-1-phenyl-2,3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), Quinpirole, and Eticlopride.

Embodiment 80

The method of embodiment 78, wherein said monoaminergic agonist is buspirone.

Embodiment 81

A stimulator configured to induce epidural and/or transcutaneous electrical stimulation and/or magnetic stimulation in the cervical region of a subject according to any one of embodiments 1-75.

Embodiment 82

A stimulator configured to induce epidural and/or transcutaneous electrical stimulation and/or magnetic stimulation in the cervical region of a subject in combination with a monoaminergic for use in improving, and/or regulating, and/or restoring respiration in a subject with a respiratory deficiency.

Embodiment 83

The stimulator of embodiment 82, wherein said at least one monoaminergic agonist comprises an agent selected from the group consisting of a serotonergic drug, a dopaminergic drug, a noradrenergic drug, a GABAergic drug, and a glycinergic drug.

Embodiment 84

The method of embodiment 83, wherein said agent is selected from the group consisting of 8-hydroxy-2-(di-n-propylamino)tetralin (8-OH-DPAT), 4-(benzodioxan-5-yl)1-(indan-2-yl)piperazine (S15535), N-{2-[4-(2-methoxyphenyl)-1-piperazinyl]ethyl}-N-(2-pyridinyl)cyclohexanecarboxamide (WAY 100.635), Quipazine, Ketanserin, 4-amino-(6-chloro-2-pyridyl)-1 piperidine hydrochloride (SR 57227A), Ondanesetron, Buspirone, Methoxamine, Prazosin, Clonidine, Yohimbine, 6-chloro-1-phenyl-2,3,4,5-tetrahydro-1H-3-benzazepine-7,8-diol (SKF-81297), 7-chloro-3-methyl-1-phenyl-1,2,4,5-tetrahydro-3-benzazepin-8-ol (SCH-23390), Quinpirole, and Eticlopride.

Embodiment 85

The method of embodiment 83, wherein said monoaminergic agonist is buspirone.

Embodiment 86

A system comprising: a stimulator configured to induce epidural and/or transcutaneous electrical stimulation and/or magnetic stimulation in the cervical region of a subject at a frequency and amplitude that improves, and/or regulates, and/or restores respiration in a subject with a respiratory deficiency; and one or more sensor selected from the group consisting of a sensor that detects chest wall movement and/or expansion, a sensor that detects blood $O_2$ saturation, and a sensor that determines end tidal $CO_2$; where the output of said sensor is coupled to said stimulator and said stimulator adjust the stimulation pattern in response to the sensor output to provide a desired tidal volume and/or $O_2$ saturation and/or end tidal $CO_2$.

Embodiment 87

The system of embodiment 86, wherein said stimulator is configured to induce epidural stimulation of the cervical spinal cord.

Embodiment 88

The system of embodiment 86, wherein said stimulator is configured to induce epidural stimulation in a method according to any one of embodiments 14-42.

Embodiment 89

The system of embodiment 86, wherein said stimulator is configured to induce transcutaneous stimulation of the cervical spinal cord.

Embodiment 90

The system of embodiment 86, wherein said stimulator is configured to induce transcutaneous stimulation in a method according to any one of embodiments 2-13.

Embodiment 91

The system of embodiment 86, wherein said stimulator is configured to induce magnetic stimulation of the cervical spinal cord.

Embodiment 92

The system of embodiment 86, wherein said stimulator is configured to induce magnetic stimulation in a method according to any one of embodiments 43-54.

Embodiment 93

The system of embodiment 86, wherein said stimulator is stimulator configured to perform a method according to any one of embodiments 1-80.

Embodiment 94

The system according to any one of embodiments 86-93, wherein said system comprises a sensor that detects blood $O_2$ saturation.

Embodiment 95

The system of embodiment 94, wherein said sensor is an external pulse oximeter.

Embodiment 96

The system of embodiment 95, wherein said sensor is a transmissive pulse oximeter.

Embodiment 97

The system of embodiment 95, wherein said sensor is a reflectance pulse oximeter.

Embodiment 98

The system according to any one of embodiments 95-97, wherein said sensor is configured for attachment to a fingertip, earlobe, foot, forehead, or chest.

Embodiment 99

The system of embodiment 94, wherein said sensor is an implantable oxygen sensor.

Embodiment 100

The system according to any one of embodiments 86-99, wherein said system comprises a sensor that determines end tidal $CO_2$.

Embodiment 101

The system of embodiment 100, wherein said sensor comprises a transcutaneous $CO_2$ sensor.

Embodiment 102

The system of embodiment 100, wherein said sensor comprises an implantable $CO_2$ sensor.

Embodiment 103

The system of embodiment 100, wherein said sensor is an external capnograph.

Embodiment 104

The system according to any one of embodiments 86-103, wherein said system comprises a sensor that detects chest wall movement and/or expansion.

Embodiment 105

The system of embodiment 104, wherein said sensor comprises a device that measures thoracic impedance.

Embodiment 106

The system of embodiment 104, wherein said sensor comprises a device that measures rib cage movement.

Embodiment 107

The system of embodiment 106, wherein said sensor comprises an inductance band.

Embodiment 108

The system of embodiment 106, wherein said sensor comprises a laser monitor.

Embodiment 109

The system of embodiment 106, wherein said sensor comprises an accelerometer.

Embodiment 110

The system of embodiment 109, wherein said accelerometer is attached to the chest surface.

Embodiment 111

The system of embodiment 109, wherein said accelerometer is implanted.

Embodiment 112

The system according to any one of embodiments 86-93, wherein said system comprises an implanted (e.g., surgically implanted), closed loop epidural stimulation device for spinal cord injured, stroke subjects, ALS patients with respiratory issues, and the like.

Embodiment 113

The system according to any one of embodiments 86-93, wherein said system comprises a temporary implanted device by percutaneous insertion of leads for ICU/acute care patients with acute respiratory failure to restore respiratory function or facilitate vent weaning.

Embodiment 114

The system of embodiment 113, wherein said system provides feedback to the controller/stimulator/from sensors assessing chest wall movement, and/or $O_2$ saturation, and/or end tidal $CO_2$ and uses this information to adjust stimulation parameters.

Embodiment 115

The system according to any one of embodiments 86-114, wherein said system is configured to use with a subject who is intubated.

Embodiment 116

The system according to any one of embodiments 86-115, wherein said system is configured for home use.

Embodiment 117

The system according to any one of embodiments 86-115, wherein said system is configured for use in an acute care facility.

Embodiment 118

The system according to any one of embodiments 86-117, wherein said system is configured for use with a subject who has a drug addiction, and/or configured for a subject at risk for sudden infant death syndrome (SIDS).

Embodiment 119

The system according to any one of embodiments 86-93, wherein said system comprises a magnetic or transcutaneous electrical stimulation device for SIDS or ICU patients with decreased respiratory drive.

Embodiment 120

The system of embodiment 119, wherein said system provides feedback to the controller/stimulator/from sensors assessing chest wall movement, and/or $O_2$ saturation, and/or end tidal $CO_2$ and uses this information to adjust stimulation parameters.

Embodiment 121

A method of removing a subject from a respirator, said method comprising: inducing or maintaining respiration is a subject using a method according to any one of embodiments 1-80, and/or a system according to any one of embodiments 86-120 while said subject is removed from the respirator (ventilator) and/or after said subject is removed from said respirator.

Embodiment 122

The method of embodiment 121, wherein said subject is a human incapable of breathing at all without assistance.

Embodiment 123

The method of embodiment 121, wherein said subject is a human requiring assistance to facilitate breathing.

In various embodiments any of the foregoing methods do not involve stimulation of the phrenic nerve and any of the foregoing devices and systems are not configured for stimulation of the phrenic nerve.

BRIEF DESCRIPTION OF THE DRAWINGS

FIG. 4A: Dorsal respiration electrode type A (32 channel). FIG. 4B: Dorsal respiration electrode type B (48 channel). FIG. 4C: Ventral respiration dual electrode type C (8 channel).

FIG. 5, panels A-C illustrates the experimental set-up. Panel A: The experimental set-up used in this study is shown. Panel B: The epidural stimulation sites on dorsal lateral spinal cord. Panel C: The recording time line for each cervical level, with sham experiment recorded first followed by stimulation.

Figure 1:
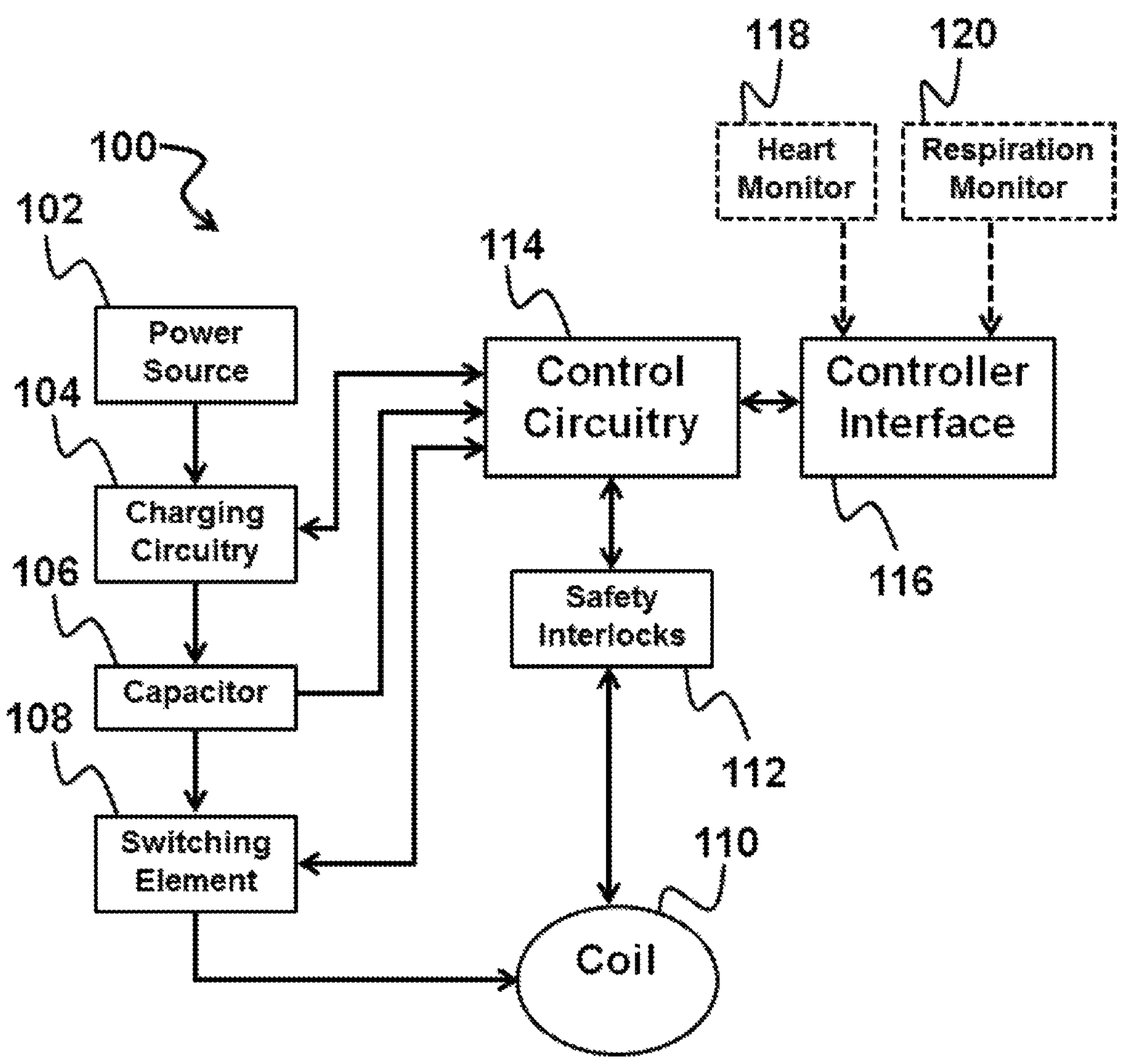
FIG. 1 shows a schematic illustration of one illustrative embodiment of a magnetic nerve stimulator.

*Inferolateral exiting electrode tail allows for insertion of electrode through posterior laminotomy approach. While illustrative dimensions are shown, it will be recognized that the dimensions can be adjusted and personalized to the patient based on anatomical dimensions based on MRI.

FIG. 7, panels A-B, shows that Respiratory frequency increased when C3 was stimulated (20 Hz, 1.5 mA). Panel A shows the respiratory frequency change when C3 was electrically stimulated or a sham stimulation was carried out. Panel B shows the respiratory peak-to-peak amplitude ratio change when C3 was electrically stimulated or a sham stimulation was carried out. The ratio was calculated using each recorded data point compared to the calculated baseline median. (n=24). The respiratory frequency was significantly increased during epidural stimulation compared to sham stimulation ($p<0.05$). However, there was no change in respiratory peak to peak amplitude during epidural stimulation compared to the sham stimulation.

FIG. 8, panels A-D, illustrates a hierarchical cluster showing different respiratory frequency change pattern due to epidural stimulation at C3 with 1.5 mA. The hierarchical cluster dendograms of the sham group (Panel A) and the epidural stimulation group (panel B) are shown above. Individual recordings were placed in separate clusters if the distance between each tracing was greater than 7.5 hierarchical units (An=animal). Panel C: Tracings of the average clusters for the sham group: (i) sham cluster 1, which consisted of data from 23 of 24 animals, and (ii) sham cluster 2 which contained data from only 1 animal. Panel D: Tracings of the average clusters for the epidural stimulation group: (i) cluster 1 contained 7 of 24 animals, (ii) cluster 2 contained 6 of 24 animals, (iii) cluster 3 contained 5 of 24 animals, (iv) cluster 4 contained 3 of 24 animals, (v) cluster 5 contained 2 of 24 animals and (vi) cluster 6 contained only 1 animal.

Figure 9:
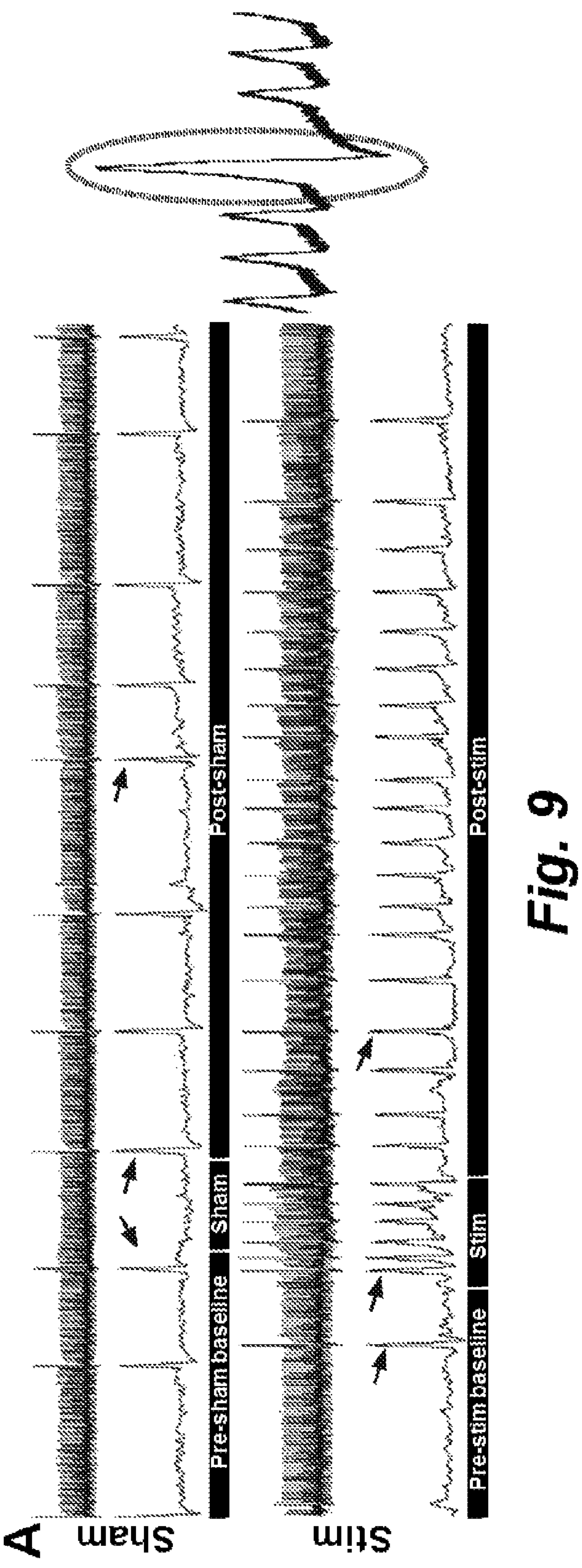

FIG. 9, panel A, is a representative trace showing the recorded tidal volume (red trace) and smoothed tidal volume (black trace) of respiration pre-stimulation, during sham or during epidural stimulation and after sham or epidural stimulation. The peaks (see blue arrows) indicate sighs, and a representative sigh is shown in detail (black dash circle on the right). FIG. 9, panel B, shows a representation of the frequency of sighs per second depending on whether sham stimulation or epidural stimulation was used. FIG. 9, panel C, shows the number of sighs for every 30 seconds in all the mice tested (n=19) either pre-stimulation, during sham or during epidural stimulation and after sham or epidural stimulation. The number of sighs was greater during epidural stimulation compared to the pre-stimulation, baseline period ($p=0.002$); significantly greater during epidural stimulation was delivered compared to the same period during sham stimulation ($p=0.0011$, see asterisk); and sigh frequency remained significantly elevated for up to 3 min after epidural stimulation stopped compared to sham ($p<0.001$, see asterisk).

Figure 10:
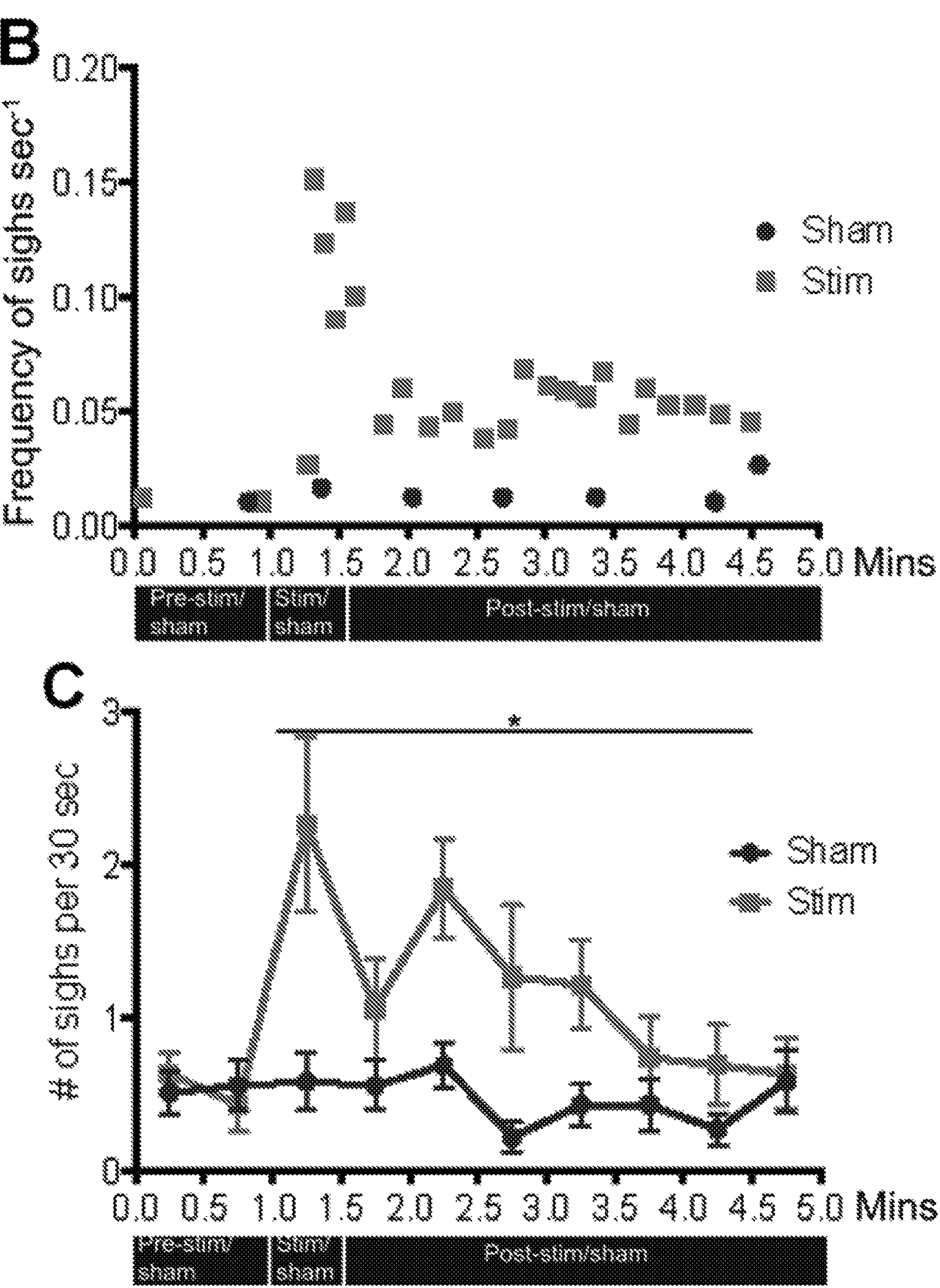

FIG. 10 shows that sigh and eupnea response after stimulation is not correlated. The left side of the chart shows the pattern of sigh clustering based on the response to stimulation compared to pre-stimulation sigh baseline. The right side of the chart shows eupnea frequency clustering based on the response to epidural stimulation compared to the pre-stimulation eupnea baseline. Each animal appears on each side of the figure according to the pattern of sighing and eupneic responses, and those animals in which the pattern of changes in sigh and eupnea were similar during and after epidural stimulation are printed in bold, red text. The effects of epidural stimulation on the frequency of eupnea and sighs seemed to be uncorrelated in individual animals in that 16 of 24 animals had different sigh and eupneic responses patterns to epidural stimulation.

Figure 11:
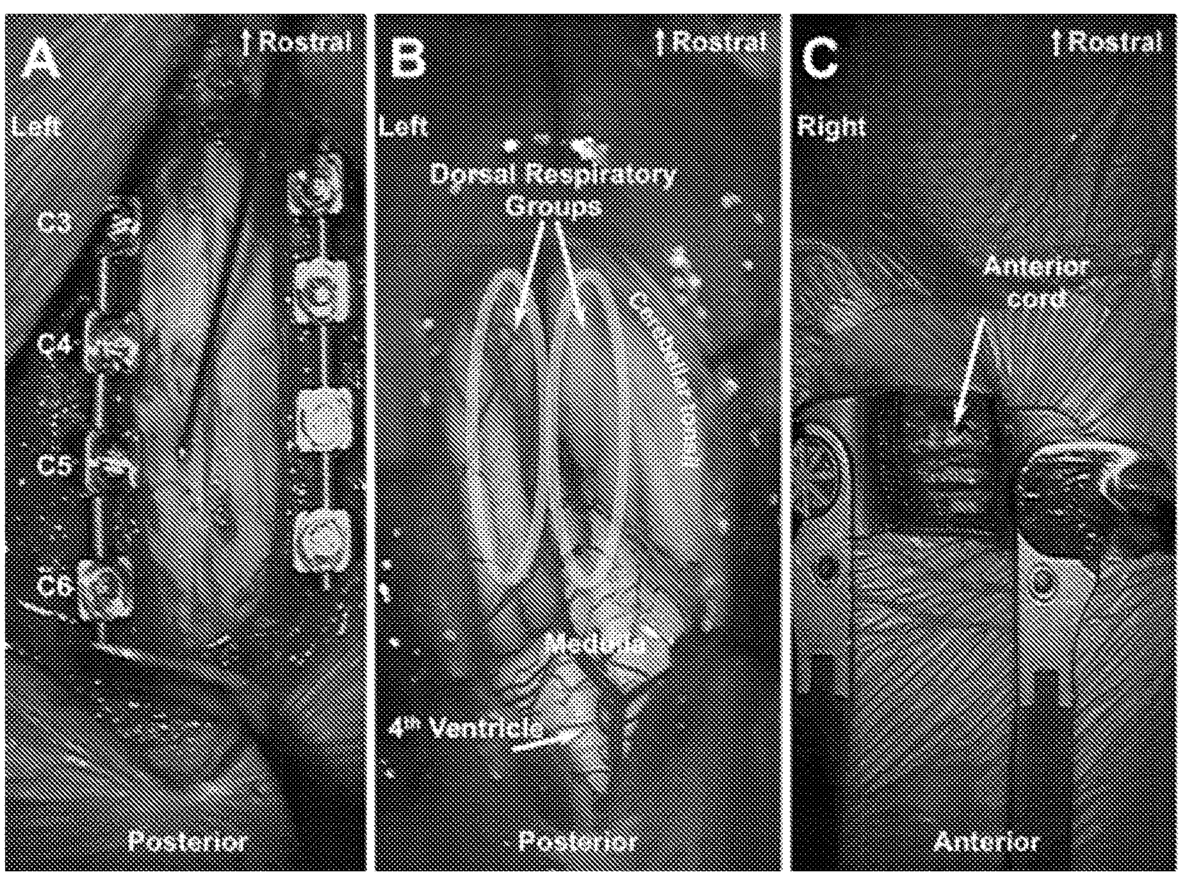

FIG. 11, panels A-C, illustrates intraoperative human stimulation. Panel A shows the dorsal cervical cord from C3 to C6 with probe placed against dura of the cord for stimulation; here just left of the midline. Panel B shows a view of the dorsal/posterior medulla at the level of the cerebellar tonsils. The plane of the medullary surface can be probed to access the floor of the $4^{th}$ ventricle, the hypoglossal triangle, and the dorsal respiratory groups. Panel C shows that anterior cervical disc surgery can provide access to the ventral cord.

Figure 12:
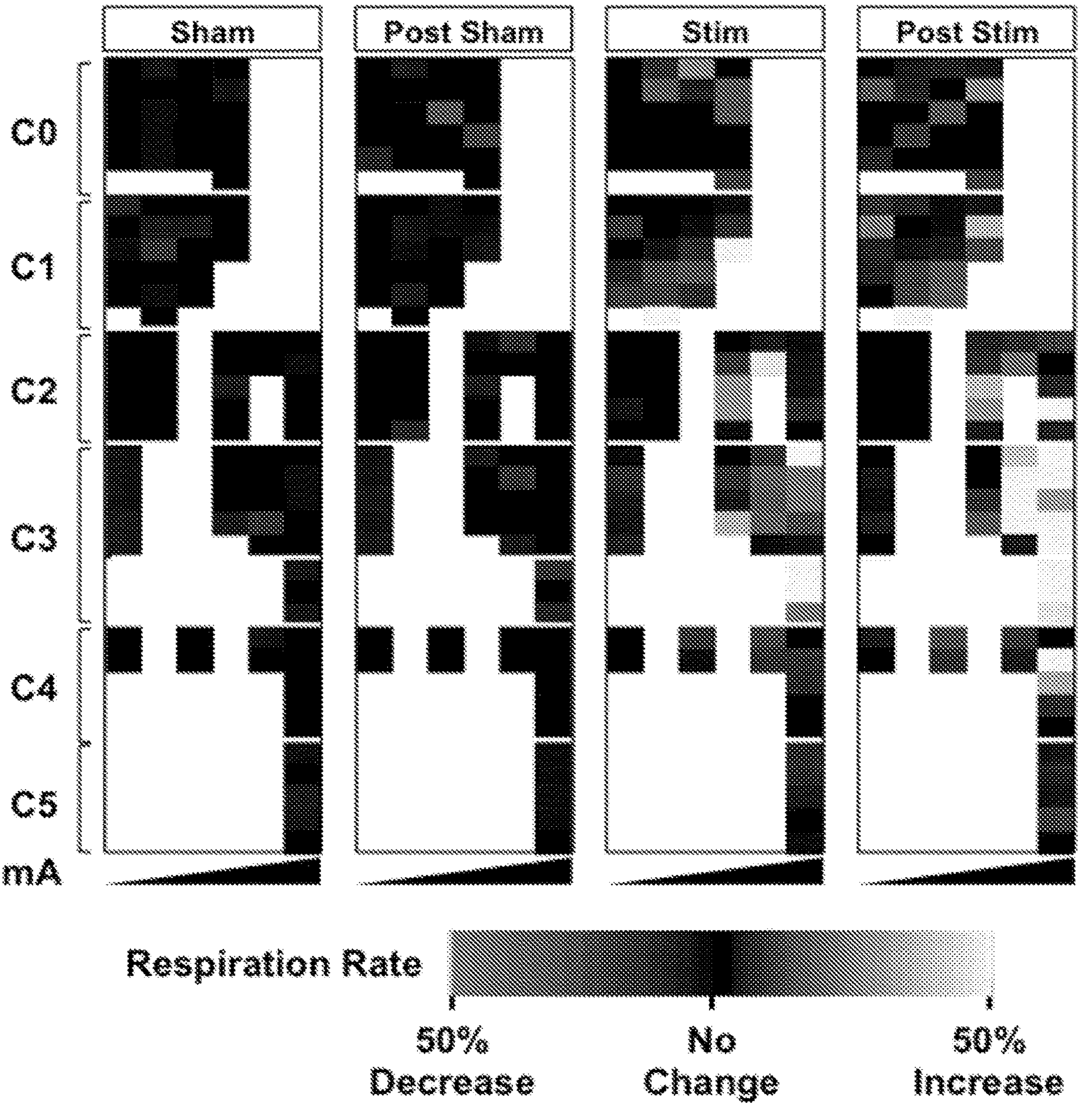

FIG. 12 shows an overview of spinal respiratory stimulation. Anesthetized mice are monitored by pneumotach and EMG to monitor the respiratory rate. Heat map color code reflects an increase (yellow) or decrease (blue) in respiratory rate.

Figure 13:
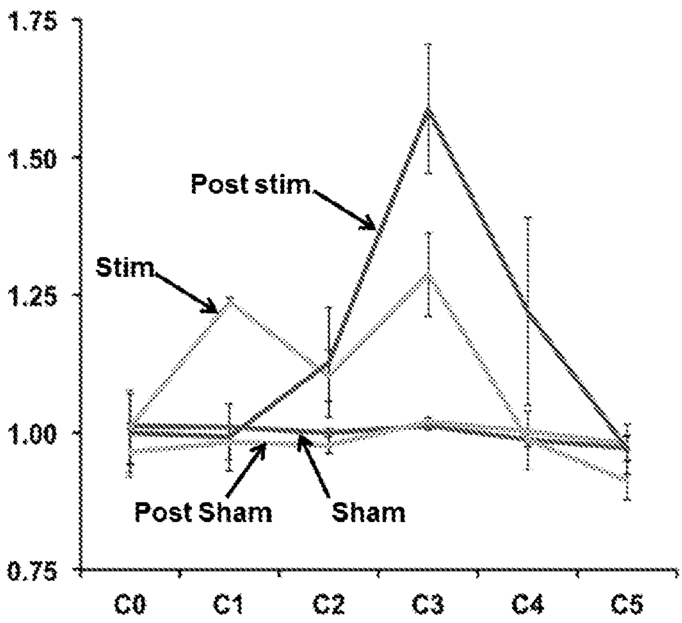

FIG. 13 shows a summary of cervical respiratory stimulation in mouse to 30 Hz stimulation.

Figure 14:
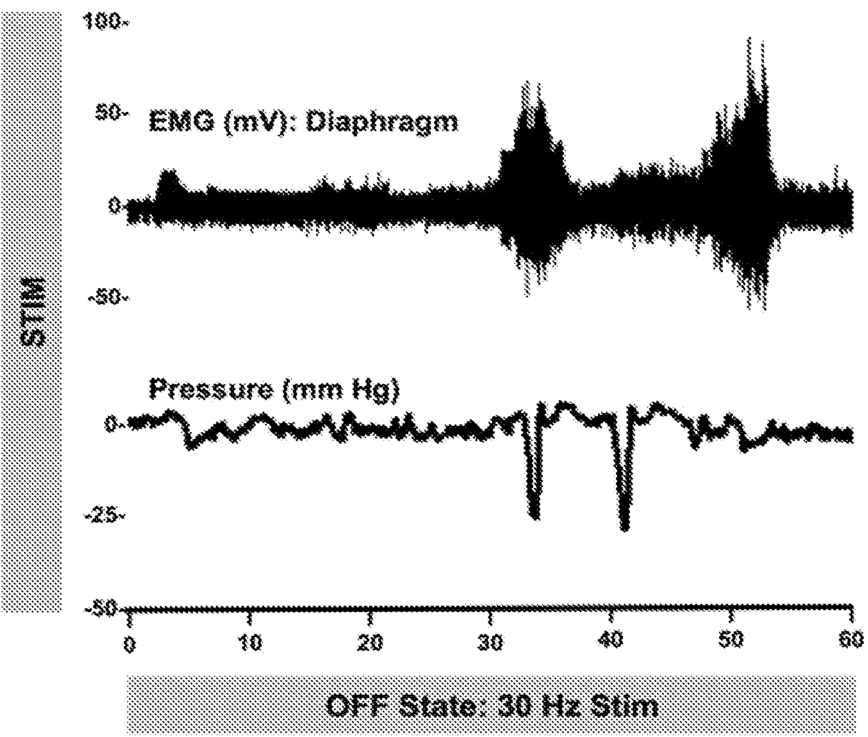

FIG. 14 shows that a 30 Hz stimulation at C3/4 can induce respiration during deep anesthesia in humans.

Figure 15:
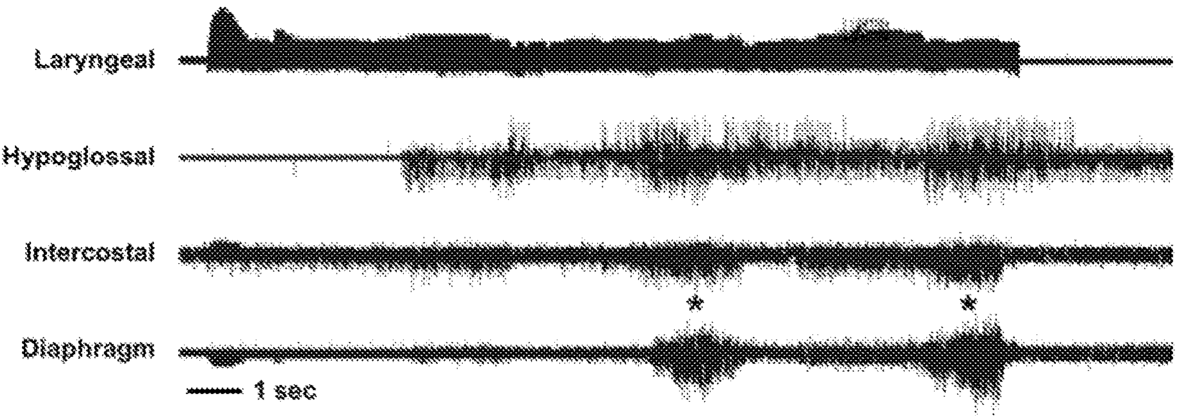

FIG. 15 shows that a 30 Hz stimulation at C3/4 can induce coordinated respiration during off-state in humans.

Figure 16:
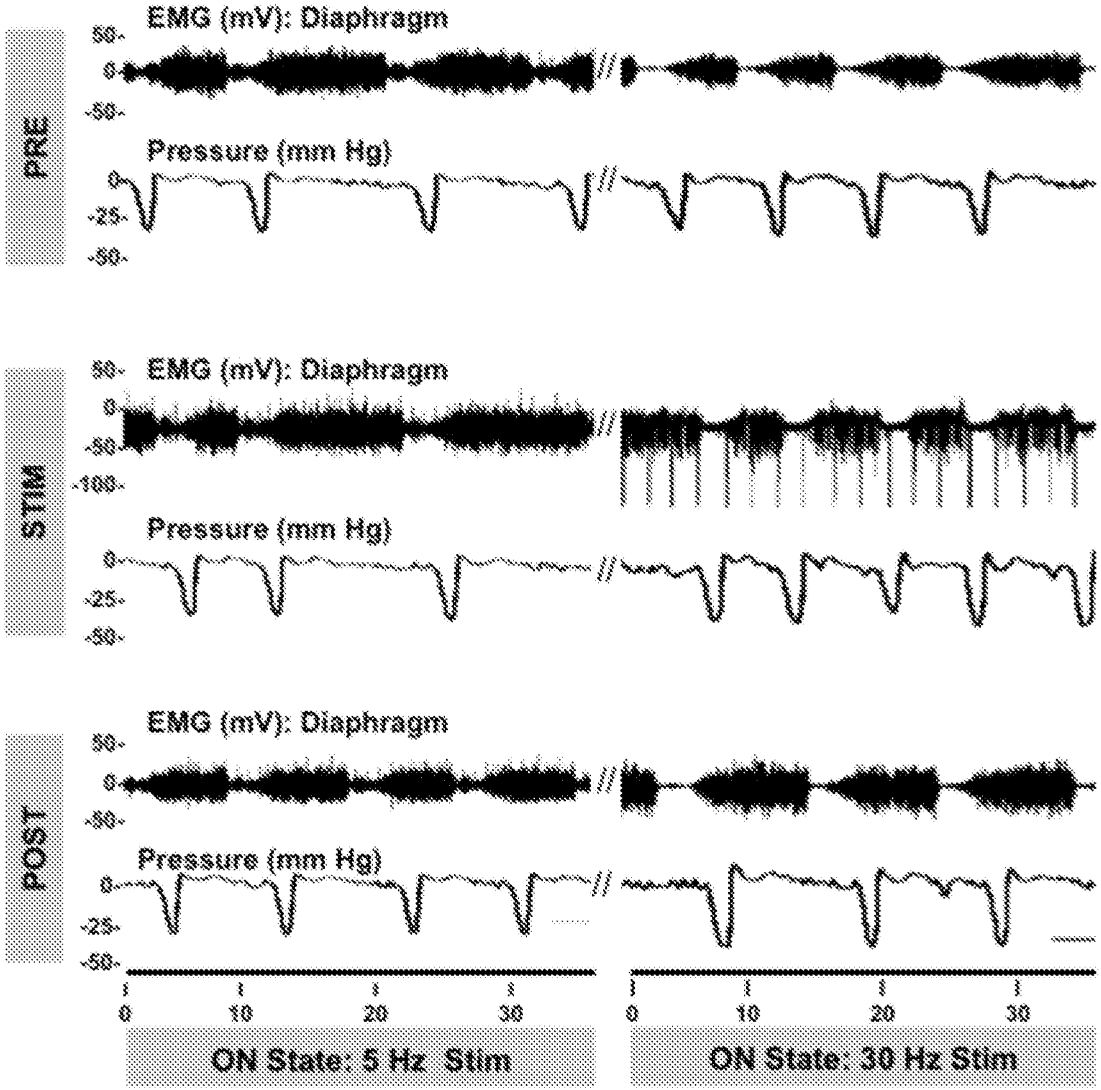

FIG. 16 shows a representative respiratory response to 30 Hz at C3/4 in humans.

Figure 17:
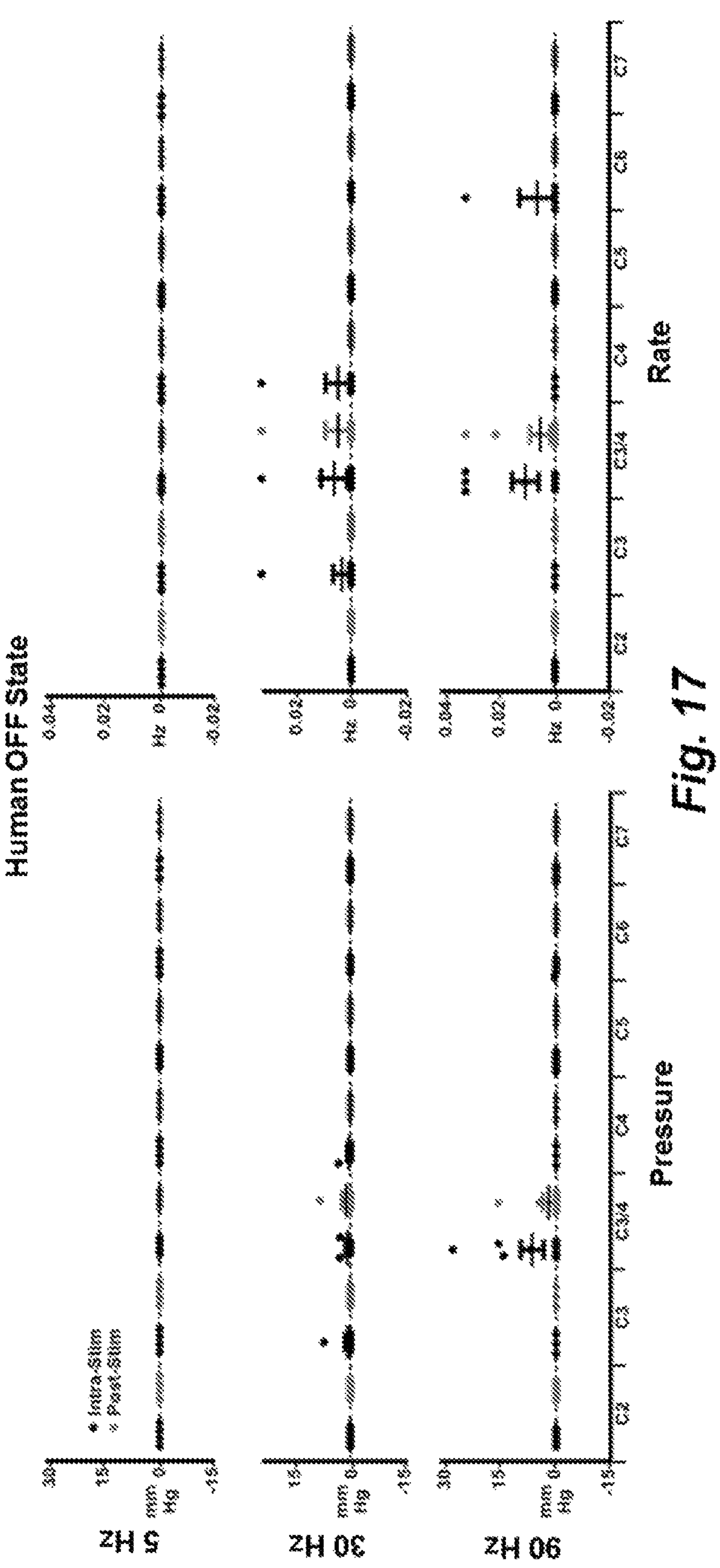

FIG. 17 shows responses to spinal stimulation during deep anesthesia in humans.

Figure 18:
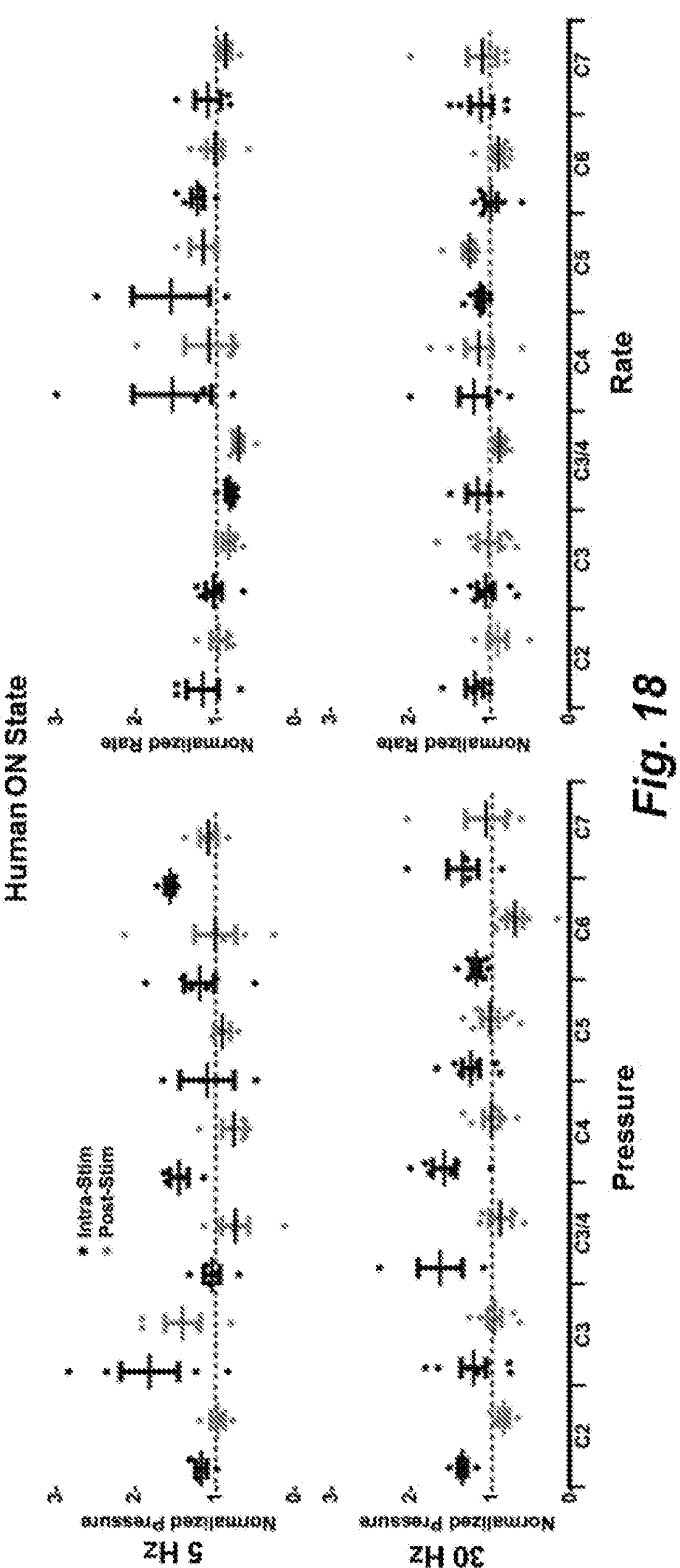

FIG. 18 shows responses to spinal stimulation during light anesthesia in humans.

DETAILED DESCRIPTION

Respiration or breathing involves a complex network of circuits that is involved in central pattern generation (CPG) that spans the brainstem and cervical spinal cord to generate a respiratory rhythm. Sensory input from central and peripheral chemoreceptors ($CO_2$), lung stretch receptors naturally influence the firing pattern of the CPG. In the disease or injury state to the brainstem or spinal cord, the respiratory rhythm is compromised, likely due to the depressed state of the CPG.

Current technology in addressing the depressed respiratory state is to stimulate the diaphragm muscle which actively participates in inspiration by phrenic nerve stimulators. The issue with this approach is that the muscle will not react to changes in the activity state of the patient and only activates the diaphragm which participates in the inspiratory phase of respiration. To fully recapitulate normal breathing in the diseased states, the source of the problem within the central pattern generator(s) needs to be addressed.

In surgery, we have discovered the following which can be leveraged to restore normal breathing in traumatic or disease setting:

1. Stimulation with electrical current (optimal of frequency of 30-60 Hz) of the cervical spinal cord can modulate breathing (rate, rhythm, tidal volume);
2. Stimulation with electrical current (particularly at frequency of 5 Hz) of cervical nerve roots can modulate breathing (rate, rhythm, tidal volume);
3. Stimulation with electrical current can restore respiratory rhythm in a depressed respiratory state (e.g., opiate induced);
4. Combination of stimulation above can strongly influence and restore respiration in depressed respiratory state; and
5. Serotonin agonist medication such as buspirone can be used as tool to further activate the CPG associated with breathing.

Stimulation of the above parameters of the various structures can be induced by epidural stimulation electrodes, non-invasive transcutaneous electrical stimulation, or magnetic stimulation.

Accordingly, in various embodiments, methods of improving, and/or regulation, and/or restoring respiration in a subject with a respiratory deficiency are provided. The methods typically involve neuromodulating the cervical spinal cord of the subject by administering transcutaneous stimulation to the cervical spinal cord or a region thereof at a frequency and intensity sufficient to restore respiration; and/or neuromodulating the cervical spinal cord of the subject by administering epidural stimulation to the cervical spinal cord or a region thereof at a frequency and intensity sufficient to restore respiration; and/or neuromodulating the cervical spinal cord of said subject with a magnetic stimulator at a frequency and intensity sufficient to restore respiration.

Unlike phrenic stimulation which directly stimulates the diaphragm muscle and does not recapitulate the afferent sensory feedback associated with respiration (e.g., $CO_2$, tidal volume, rate, etc.), the methods described herein that involve stimulation of nerve root and/or spinal cord, activate a respiratory drive that is responsive to normal feedback. It is believed more fully recapitulate normal breathing patterns.

It is believed there are no previous methods of activating the respiratory network to induce respiration in settings of decreased respiratory drive such as brain injury (stroke, traumatic brain injury, spinal cord injury), medication overdose, neurodegenerative disorders (ALS, Alzheimer's, Parkinson's, multiple sclerosis), among others. The methods described herein can be used to activate the respiratory network to wean patients from ventilators, or as respiratory "pacemakers" to maintain respiratory drive, therefore replacing ventilators. In the traumatic setting, this strategy can be used as a "respiratory defibrillator" (similar to a cardiac defibrillator) equivalent for respiration. The spinal cord can be thus be stimulated to activate the respiratory drive in a number of contexts where a subject has a respiratory deficiency (e.g., reduced respiratory drive).

In certain embodiments, the respiratory defibrillator can be integrated into an automatic external defibrillator (AED) An automated external defibrillator (AED) is a portable device that can check the heart rhythm and can send an electric shock to the heart to try to restore a normal rhythm. Where the respiratory defibrillator is integrated into an AED, the same device can be used to stimulate a heart rhythm and/or to stimulate or maintain respiration as necessary.

The methods described herein are typically for use with a mammal (e.g., a human, a mammal (e.g., a non-human primate, equine, feline, canus, etc.) with a respiratory deficiency. Such respiratory deficiencies can arise in a number of contexts. For example, they can arise where a subject has a brain injury and/or a spinal cord injury. In the latter context, it is believed the methods described herein will be effective where the spinal cord injury is clinically classified as motor complete or motor incomplete. The methods also find use in cases of ischemic brain injury (e.g., due to stroke, drowning or other oxygen deficiency, or acute trauma). It is also believed the methods will also find use there the respiratory deficiency is due to a neurodegenerative disorder (e.g., Parkinson's disease, Huntington's disease, Alzheimer's disease, amyotrophic lateral sclerosis (ALS), primary lateral sclerosis (PLS), dystonia, cerebral palsy, and the like). The methods also find use in cases of depressed respiration due to drug overdose.

It is also noted that in certain embodiments, the methods described herein can be used in conjunction with conventional respirators, e.g., to provide improved respiratory action or the methods can be used to substitute for or to wean a subject off of a traditional respirator.

In certain embodiments, the methods described herein can also be used in combination with the administration of one or more neuromodulatory drugs (e.g., a monoaminergic agonist as described herein).

In certain embodiments the methods, and apparatus (e.g. systems) described herein can be used to wean a subject from a ventilator. By way of illustration, transcutaneous, epidural, and/or magnetic stimulation of respiration as described herein can be used to maintain respiration in a subject as they are removed from a respirator (ventilator) and/or after they have been removed from a ventilator, e.g., to facilitate respiration where there is an endogenous respiratory pattern, or to induce respiration where absent respirator or stimulation respiration would cease.

Transcutaneous Stimulation of a Region of the Cervical Spine.

The location of the electrode(s) and their stimulation parameters can be important in modulating the subject's respiration rate. Use of surface electrode(s), as described herein, facilitates selection or alteration of particular stimulation sites as well as the application of a wide variety of stimulation parameters. Additionally, surface stimulation can be used to optimize location for an implantable electrode or electrode array for epidural stimulation.

In various embodiments, the methods described herein involve transcutaneous electrical stimulation of the cervical spine or a region of the cervical spine of the subject to restore or regulate respiration. Illustrative regions include, but are not limited to one or more regions straddling or spanning a region selected from the group consisting of C1-C1, C1-C2, C1-C3, C1-C4, C1-C7, C1-C6, C1-C7, C1-T1, C2-C2, C2-C3, C2-C4, C2-05, C2-C6, C2-C7, C2-T1, C3-C3, C3-C4, C3-05, C3-C6, C3-C7, C3-T1, C4-C4, C4-05, C4-C6, C4-C7, C4-T1, C5-05, C5-C6, C5-C7, C5-T1, C6-C6, C6-C7, C6-T1, C7-C7, and C7-T1.

In certain embodiments the transcutaneous stimulation is applied at a region comprising C2-C4 or a region therein. In certain embodiments the stimulation is applied at C3.

In certain embodiments the transcutaneous stimulation is at a frequency of at least about 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz, or at least about 1 kHz, or at least about 1.5 kHz, or at least about 2 kHz, or at least about 2.5 kHz, or at least about 5 kHz, or at least about 10 kHz, or up to about 25 kHz, or up to about 50 kHz, or up to about 100 kHz.

In certain embodiments the transcutaneous stimulation is at a frequency ranging from about 1 Hz, or from about 2 Hz, or from about 3 Hz, or from about 4 Hz, or from about 5 Hz, or from about 10 Hz, or from about 10 Hz, or from about 10 Hz, up to about 500 Hz, or up to about 400 Hz, or up to about 300 Hz, or up to about 200 Hz up to about 100 Hz, or up to about 90 Hz, or up to about 80 Hz, or up to about 60 Hz, or up to about 40 Hz, or from about 3 Hz or from about 5 Hz up to about 80 Hz, or from about 5 Hz to about 60 Hz, or up to about 30 Hz. In certain embodiments the transcutaneous stimulation is at a frequency ranging from about 20 Hz or about 30 Hz to about 90 Hz or to about 100 Hz, to initiate respiration when no respiration pattern is present. In certain embodiments the transcutaneous stimulation is at a frequency ranging from about 5 Hz or about 10 Hz up to about 90 Hz or about 100 Hz, when a respiration pattern is present.

In certain embodiments the transcutaneous stimulation is applied at an intensity ranging from about 5 mA or about 10 mA up to about 500 mA, or from about 5 mA or about 10 mA up to about 400 mA, or from about 5 mA or about 10 mA up to about 300 mA, or from about 5 mA or about 10 mA up to about 200 mA, or from about 5 mA or about 10 mA to up about 150 mA, or from about 5 mA or about 10 mA up to about 50 mA, or from about 5 mA or about 10 mA up to about 100 mA, or from about 5 mA or about 10 mA up to about 80 mA, or from about 5 mA or about 10 mA up to about 60 mA, or from about 5 mA or about 10 mA up to about 50 mA.

In certain embodiments the transcutaneous stimulation is applied stimulation comprises pulses having a width that ranges from about 100 μs up to about 1 ms or up to about 800 μs, or up to about 600 μs, or up to about 500 μs, or up to about 400 μs, or up to about 300 μs, or up to about 200 μs, or up to about 100 μs, or from about 150 μs up to about 600 μs, or from about 200 μs up to about 500 μs, or from about 200 μs up to about 400 μs.

In certain embodiments the transcutaneous stimulation is at a frequency, pulse width, and amplitude sufficient to restore a resting respiration rate and at least 60%, or at least 70%, or at least 80%, or at least 90% of the subjects normal tidal volume.

In certain embodiments the transcutaneous stimulation is superimposed on a high frequency carrier signal. In certain embodiments the high frequency carrier signal ranges from about 3 kHz, or about 5 kHz, or about 8 kHz up to about 30 kHz, or up to about 20 kHz, or up to about 15 kHz. In certain embodiments the carrier signal is about 10 kHz. In certain embodiments the carrier frequency amplitude ranges from about 30 mA, or about 40 mA, or about 50 mA, or about 60 mA, or about 70 mA, or about 80 mA up to about 300 mA, or up to about 200 mA, or up to about 150 mA.

Epidural Stimulation of a Region of the Cervical Spine

In various embodiments, the methods described herein involve epidural electrical stimulation of the cervical spine or a region of the cervical spine of the subject to modulate and/or induce respiration. Illustrative regions include, but are not limited to, one or more regions straddling or spanning a region selected from the group consisting of C1-C1, C1-C2, C1-C3, C1-C4, C1-C7, C1-C6, C1-C7, C1-T1, C2-C2, C2-C3, C2-C4, C2-05, C2-C6, C2-C7, C2-T1, C3-C3, C3-C4, C3-05, C3-C6, C3-C7, C3-T1, C4-C4, C4-05, C4-C6, C4-C7, C4-T1, C5-05, C5-C6, C5-C7, C5-T1, C6-C6, C6-C7, C6-T1, C7-C7, and C7-T1.

In certain embodiments the epidural stimulation is applied paraspinally over a cervical region identified above (e.g., over vertebrae spanning C0 to C8 or a region thereof, e.g., over a region spanning C2 to C4).

In certain embodiments the epidural stimulation is applied at a region comprising C2-C4 or a region therein. In certain embodiments the stimulation is applied at C3.

Figure 3:
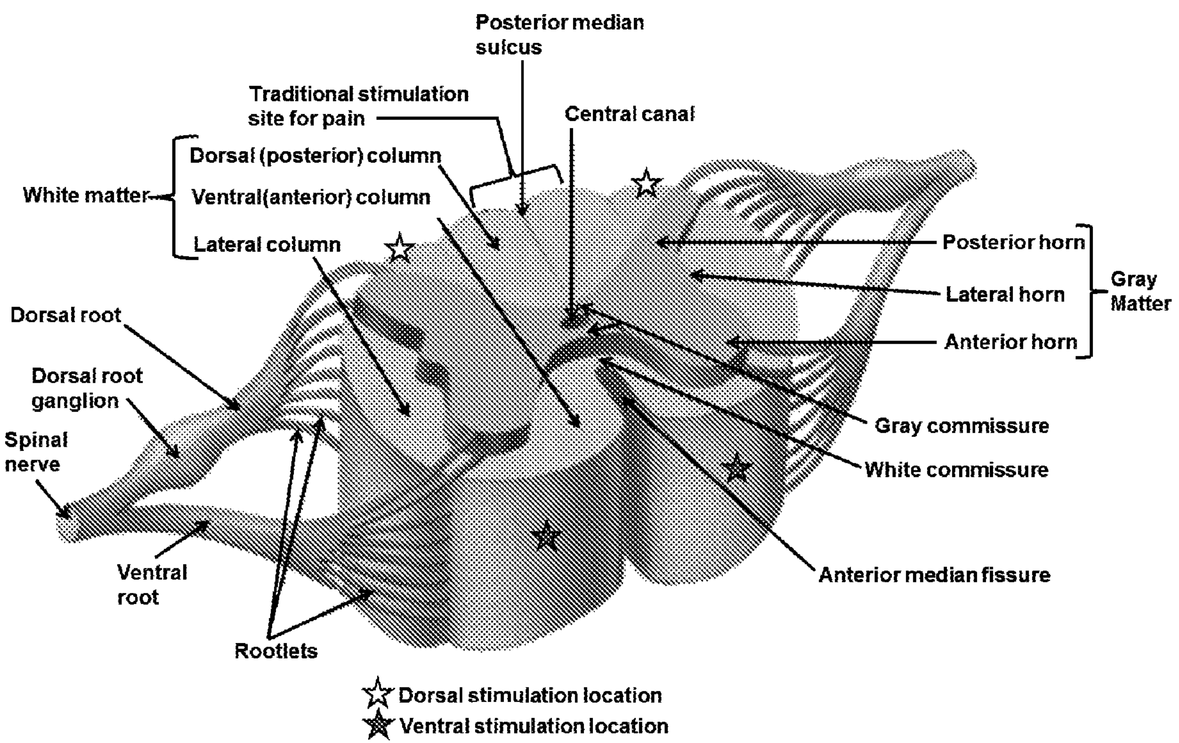
FIG. 3 shows an anterolateral view of the spinal cord illustrating sites of epidural stimulation.

In certain embodiments the epidural stimulation is applied to the dorsal (posterior) column (see, e.g., FIG. 3) and in certain embodiments to the lateral portion of the dorsal (posterior) column as shown in FIG. 3.

In certain embodiments the epidural stimulation is alternatively or additionally applied to a dorsal root, and in certain embodiments to a dorsal root at the point of entry (see, e.g., FIG. 3).

In certain embodiments the epidural stimulation is alternatively or additionally applied to a ventral (anterior) column and in certain embodiments to a lateral portion of the ventral column (see, e.g., FIG. 3).

In certain embodiments the epidural stimulation is alternatively or additionally applied to a ventral root and in certain embodiments to a ventral root at the point of entry.

In certain embodiments the epidural stimulation to a ventral column and/or a ventral root speeds up respiration in a subject that is already breathing.

In certain embodiments, the epidural stimulation is at a frequency of at least about 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz, or at least about 1 kHz, or at least about 1.5 kHz, or at least about 2 kHz, or at least about 2.5 kHz, or at least about 5 kHz, or at least about 10 kHz, or up to about 25 kHz, or up to about 50 kHz, or up to about 100 kHz.

In certain embodiments, the epidural stimulation is at a frequency ranging from about 1 Hz, or from about 2 Hz, or from about 3 Hz, or from about 4 Hz, or from about 5 Hz, or from about 10 Hz, or from about 10 Hz, or from about 10 Hz, up to about 500 Hz, or up to about 400 Hz, or up to about 300 Hz, or up to about 200 Hz up to about 100 Hz, or up to about 90 Hz, or up to about 80 Hz, or up to about 60 Hz, or up to about 40 Hz, or from about 3 Hz or from about 5 Hz up to about 80 Hz, or from about 5 Hz to about 60 Hz, or up to about 30 Hz.

In certain embodiments, the epidural stimulation is at a frequency ranging from about 20 Hz or about 30 Hz to about 90 Hz or to about 100 Hz, to initiate respiration when no respiration pattern is present.

In certain embodiments, the epidural stimulation is at a frequency ranging ranging from about 5 Hz or about 10 Hz up to about 90 Hz or about 100 Hz, when a respiration pattern is present.

In certain embodiments, the epidural stimulation is at an amplitude ranging from 0.5 mA, or from about 1 mA, or from about 2 mA, or from about 3 mA, or from about 4 mA, or from about 5 mA up to about 50 mA, or up to about 30 mA, or up to about 20 mA, or up to about 15 mA, or from about 5 mA to about 20 mA, or from about 5 mA up to about 15 mA.

In certain embodiments, the epidural stimulation is with pulses having a pulse width ranging from about 100 μs up to about 1 ms or up to about 800 μs, or up to about 600 μs, or up to about 500 μs, or up to about 400 μs, or up to about 300 μs, or up to about 200 μs, or up to about 100 μs, or from about 150 μs up to about 600 μs, or from about 200 μs up to about 500 μs, or from about 200 μs up to about 400 μs.

In certain embodiments, the epidural stimulation is at a frequency and amplitude sufficient to modulate and/or restore a resting (or active depending on context) respiration rate and at least 60%, or at least 70%, or at least 80%, or at least 90%, or at least 95%, or at least 98% of the subjects normal tidal volume.

In certain embodiments, the epidural stimulation is applied via a permanently implanted electrode array (e.g., a typical density electrode array, a high density electrode array, etc.).

In certain embodiments, the epidural electrical stimulation is administered via a high density epidural stimulating array (e.g., as described in PCT Publication No: WO/2012/094346 (PCT/US2012/020112). In certain embodiments, the high density electrode arrays are prepared using microfabrication technology to place numerous electrodes in an array configuration on a flexible substrate. In some embodiments, epidural array fabrication methods for retinal stimulating arrays can be used in the methods described herein (see, e.g., Maynard (2001) *Annu. Rev. Biomed. Eng.,* 3: 145-168; Weiland and Humayun (2005) *IEEE Eng. Med. Biol. Mag.,* 24(5): 14-21, and U.S. Patent Publications 2006/0003090 and 2007/0142878). In various embodiments, the stimulating arrays comprise one or more biocompatible metals (e.g., gold, platinum, chromium, titanium, iridium, tungsten, and/or oxides and/or alloys thereof) disposed on a flexible material. Flexible materials can be selected from parylene A, parylene C, parylene AM, parylene F, parylene N, parylene D, silicon, other flexible substrate materials, or combinations thereof. Parylene has the lowest water permeability of available microfabrication polymers, is deposited in a uniquely conformal and uniform manner, has previously been classified by the FDA as a United States Pharmacopeia (USP) Class VI biocompatible material (enabling its use in chronic implants) (Wolgemuth, Medical Device and Diagnostic Industry, 22(8): 42-49 (2000)), and has flexibility characteristics (Young's modulus ~4 GPa (Rodger and Tai (2005) *IEEE Eng. Med. Biology,* 24(5): 52-57)), lying in between those of PDMS (often considered too flexible) and most polyimides (often considered too stiff). Finally, the tear resistance and elongation at break of parylene are both large, minimizing damage to electrode arrays under surgical manipulation. The preparation and parylene microelectrode arrays suitable for use in the epidural stimulation methods described herein is described in PCT Publication No:

WO/2012/100260 (PCT/US2012/022257). Another suitable microelectrode array is the NEUROPORT® microelectrode array (Cyberkinetics Neurotechnology Systems Inc., Boston, MA) which consists of 96 platinum microelectrodes, arranged in a 10×10 array without electrodes at the corners, affixed to a 4 $mm^2$ silicon base.

Figure 4A:
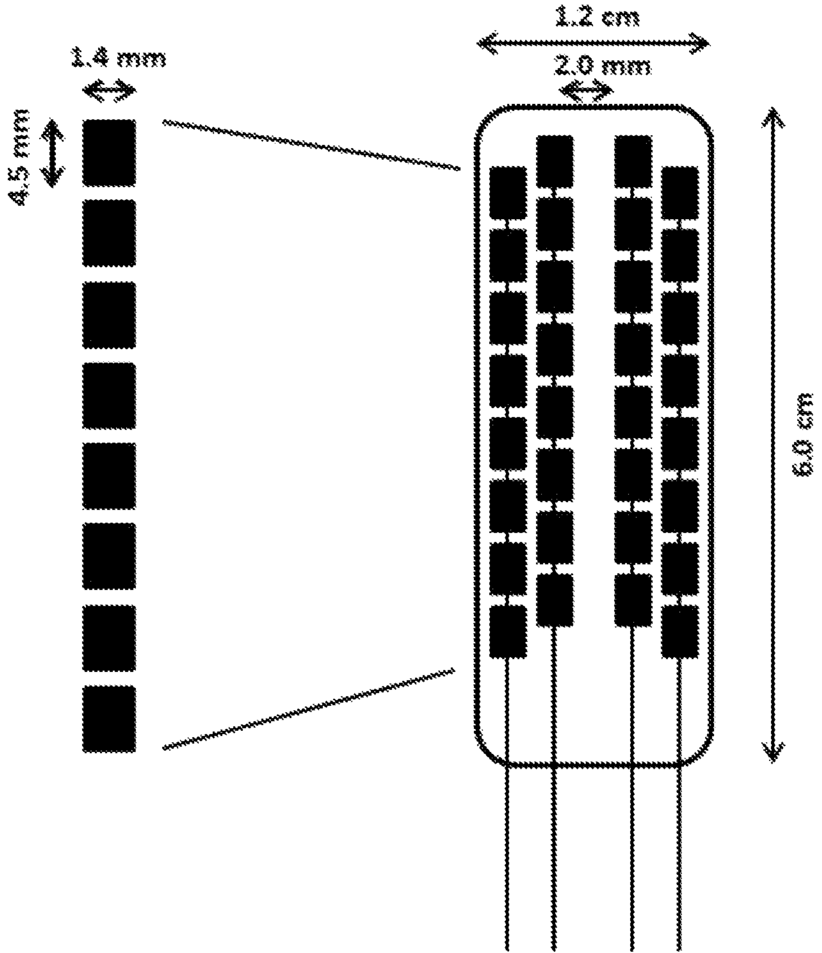
FIGS. 4A-4C illustrate epidural electrodes for stimulating respiration.
Figure 4B:
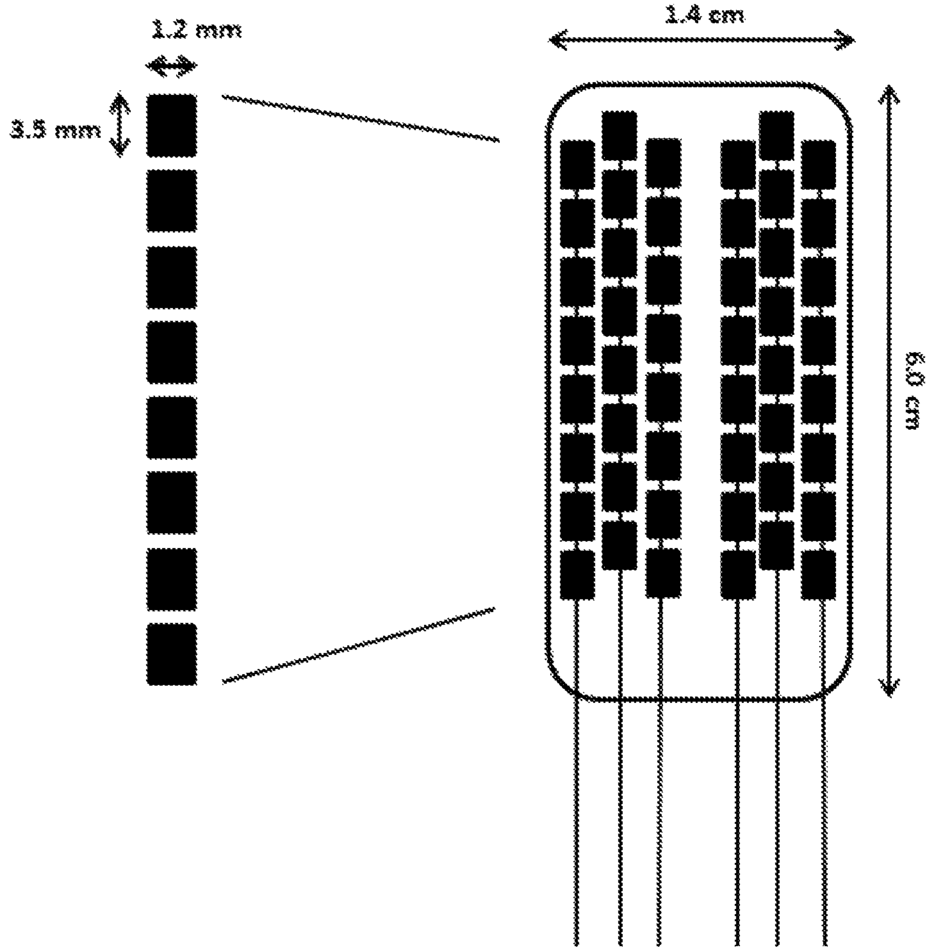
Figure 4C:
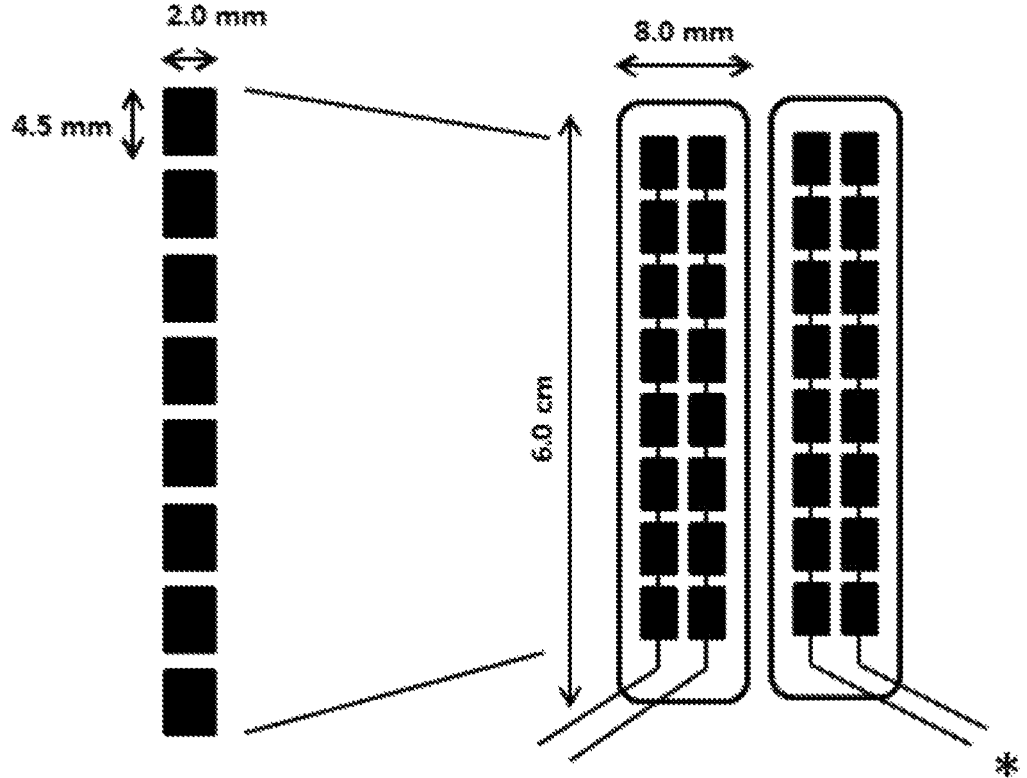

In certain illustrative, but non-limiting, embodiments an electrode array is utilized that has a configuration that provides a 32 channel dorsal respiration electrode type A, e.g., substantially as illustrated in FIG. 4A. In certain illustrative, but non-limiting, embodiments an electrode array is utilized that has a configuration that provides a configuration that is a 48 channel dorsal respiration electrode type B, e.g., substantially as illustrated in FIG. 4B. In certain illustrative, but non-limiting, embodiments an electrode array is utilized that has a configuration that provides an 8 channel ventral respiration dual electrode type C, e.g., substantially as illustrated in FIG. 4C. In certain embodiments the electrode array has an inferolateral exiting electrode tail).

The electrode array may be implanted using any of a number of methods (e.g., a laminectomy procedure) well known to those of skill in the art. For example, in some embodiments, electrical energy is delivered through electrodes positioned external to the dura layer surrounding the spinal cord. Stimulation on the surface of the cord (subdurally) is also contemplated, for example, stimulation may be applied to the dorsal columns as well as to the dorsal root entry zone. In certain embodiments the electrodes are carried by two primary vehicles: a percutaneous lead and a laminotomy lead. Percutaneous leads can typically comprise two or more, spaced electrodes (e.g., equally spaced electrodes), that are placed above the dura layer, e.g., through the use of a Touhy-like needle. For insertion, the Touhy-like needle can be passed through the skin, between desired vertebrae, to open above the dura layer. An example of an eight-electrode percutaneous lead is an OCTRODE® lead manufactured by Advanced Neuromodulation Systems, Inc.

Laminotomy leads typically have a paddle configuration and typically possess a plurality of electrodes (for example, two, four, eight, sixteen. 24, or 32) arranged in one or more columns. An example of an eight-electrode, two column laminotomy lead is a LAMITRODE® 44 lead manufactured by Advanced Neuromodulation Systems, Inc. In certain embodiments the implanted laminotomy leads are transversely centered over the physiological midline of a subject. In such position, multiple columns of electrodes are well suited to administer electrical energy on either side of the midline to create an electric field that traverses the midline. A multi-column laminotomy lead enables reliable positioning of a plurality of electrodes, and in particular, a plurality of electrode rows that do not readily deviate from an initial implantation position.

Laminotomy leads are typically implanted in a surgical procedure. The surgical procedure, or partial laminectomy, typically involves the resection and removal of certain vertebral tissue to allow both access to the dura and proper positioning of a laminotomy lead. The laminotomy lead offers a stable platform that is further capable of being sutured in place.

In the context of conventional spinal cord stimulation, the surgical procedure, or partial laminectomy, can involve the resection and removal of certain vertebral tissue to allow both access to the dura and proper positioning of a laminotomy lead. Depending on the position of insertion, however, access to the dura may only require a partial removal of the ligamentum flavum at the insertion site. In certain embodiments, two or more laminotomy leads are positioned within the epidural space of C1-C7 as identified above. The leads may assume any relative position to one another.

In certain embodiments the electrode array is disposed on the nerve roots and/or the ventral surface. Electrode arrays can be inserted into the ventral and/or nerve root area via a laminotomy procedure.

In various embodiments, the arrays are operably linked to control circuitry that permits selection of electrode(s) to activate/stimulate and/or that controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using constant current or constant voltage delivery of the stimulation. In certain embodiments time-varying current and/or time-varying voltage may be utilized.

In certain embodiments, the electrodes can also be provided with implantable control circuitry and/or an implantable power source. In various embodiments, the implantable control circuitry can be programmed/reprogrammed by use of an external device (e.g., using a handheld device that communicates with the control circuitry through the skin). The programming can be repeated as often as necessary.

The epidural electrode stimulation systems described herein are intended to be illustrative and non-limiting. Using the teachings provided herein, alternative epidural stimulation systems and methods will be available to one of skill in the art.

Magnetic Stimulation.

Magnetic stimulators can be also be used for stimulation of nerves in the cervical spinal cord to modulate/induce, and/or restore respiration. Magnetic nerve stimulation is achieved by generating a rapidly changing magnetic field to induce a current at the nerve(s) of interest. Effective nerve stimulation typically utilizes current transient of about $10^8$ A/s or greater discharged through a stimulating coil. The discharge current flowing through the stimulating coil generates magnetic lines of force. As the lines of force cut through tissue, a current is generated in that tissue, whether skin, bone, muscle or neural; if the induced current is of sufficient amplitude and duration such that the cell membrane is depolarized, neuromuscular tissue will be stimulated in the same manner as conventional electrical stimulation.

Thus, it will be recognized that a magnetic field is simply the means by which an electrical current is generated within the tissue, and that it is the electrical current, and not the magnetic field, that causes the depolarization of the cell membrane and thus the stimulation of the target muscle/nerve.

Since the magnetic field strength falls off with the square of the distance from the stimulating coil, the stimulus strength is at its highest close to the coil surface. The stimulation characteristics of the magnetic pulse, such as depth of penetration, strength and accuracy, depend on the rise time, peak electrical energy transferred to the coil and the spatial distribution of the field. The rise time and peak coil energy are governed by the electrical characteristics of the magnetic stimulator and stimulating coil, whereas the spatial distribution of the induced electric field depends on the coil geometry and the anatomy of the region of induced current flow.

In various embodiments the magnetic nerve stimulator will produce a field strength up to about 10 tesla, or up to about 8 tesla, or up to about 6 tesla, or up to about 5 tesla, or up to about 4 tesla, or up to about 3 tesla, or up to about 2 tesla, or up to about 1 tesla. In certain embodiments the nerve stimulator produces pulses with a duration from about 100 μs up to about 10 ms, or from about 100 μs up to about 1 ms.

In certain embodiments the magnetic stimulation is at a frequency of at least about 1 Hz, or at least about 2 Hz, or at least about 3 Hz, or at least about 4 Hz, or at least about 5 Hz, or at least about 10 Hz, or at least about 20 Hz or at least about 30 Hz or at least about 40 Hz or at least about 50 Hz or at least about 60 Hz or at least about 70 Hz or at least about 80 Hz or at least about 90 Hz or at least about 100 Hz, or at least about 200 Hz, or at least about 300 Hz, or at least about 400 Hz, or at least about 500 Hz.

In certain embodiments the magnetic stimulation is at a frequency ranging from about 1 Hz, or from about 2 Hz, or from about 3 Hz, or from about 4 Hz, or from about 5 Hz, or from about 10 Hz, or from about 10 Hz, or from about 10 Hz, up to about 500 Hz, or up to about 400 Hz, or up to about 300 Hz, or up to about 200 Hz up to about 100 Hz, or up to about 90 Hz, or up to about 80 Hz, or up to about 60 Hz, or up to about 40 Hz, or from about 3 Hz or from about 5 Hz up to about 80 Hz, or from about 5 Hz to about 60 Hz, or up to about 30 Hz.

In certain embodiments the magnetic stimulation is at a frequency ranging from about 20 Hz or about 30 Hz to about 90 Hz or to about 100 Hz, to initiate respiration when no respiration pattern is present.

In certain embodiments the magnetic stimulation is at a frequency ranging from about 5 Hz or about 10 Hz up to about 90 Hz or about 100 Hz, when a respiration pattern is present.

In various embodiments, the methods described herein involve magnetic stimulation of the cervical spine or a region of the cervical spine of the subject to modulate and/or induce respiration. Illustrative regions include, but are not limited to, one or more regions straddling or spanning a region selected from the group consisting of C1-C1, C1-C2, C1-C3, C1-C4, C1-C7, C1-C6, C1-C7, C1-T1, C2-C2, C2-C3, C2-C4, C2-05, C2-C6, C2-C7, C2-T1, C3-C3, C3-C4, C3-05, C3-C6, C3-C7, C3-T1, C4-C4, C4-05, C4-C6, C4-C7, C4-T1, C5-05, C5-C6, C5-C7, C5-T1, C6-C6, C6-C7, C6-T1, C7-C7, and C7-T1.

In certain embodiments, the magnetic stimulation is at a frequency and amplitude sufficient to modulate and/or restore a resting (or active depending on context) respiration rate and at least 60%, or at least 70%, or at least 80%, or at least 90%, or at least 95%, or at least 98% of the subjects normal tidal volume.

Stimulators and Stimulation Systems.

Electrical Stimulators.

Any present or future developed stimulation system capable of providing an electrical signal to one or more regions of the cervical spinal cord may be used in accordance with the teachings provided herein. Electrical stimulation systems (e.g., pulse generator(s)) can be used with both transcutaneous stimulation and epidural stimulation.

In various embodiments, the system may comprise an external pulse generator for use with either a transcutaneous stimulation system or an epidural system. In other embodiments the system may comprise an implantable pulse generator to produce a number of stimulation pulses that are sent to a region in proximity to the cervical spinal cord by insulated leads coupled to the spinal cord by one or more electrodes and/or an electrode array to provide epidural stimulation. In certain embodiments the one or more electrodes or one or more electrodes comprising the electrode array may be attached to separate conductors included within a single lead. Any known or future developed lead useful for applying an electrical stimulation signal in proximity to a subject's spinal cord may be used. For example, the leads may be conventional percutaneous leads, such as PISCES® model 3487A sold by Medtronic, Inc. In some embodiments, it may be desirable to employ a paddle-type lead.

Any known or future developed external or implantable pulse generator may be used in accordance with the teachings provided herein. For example, one internal pulse generator may be an ITREL® II or Synergy pulse generator available from Medtronic, Inc, Advanced Neuromodulation Systems, Inc.'s GENESIS™ pulse generator, or Advanced Bionics Corporation's PRECISION™ pulse generator. One of skill in the art will recognize that the above-mentioned pulse generators may be advantageously modified to modulate respiration in accordance with the teachings provided herein.

In certain embodiments systems can employ a programmer coupled via a conductor to a radio frequency antenna. This system permits attending medical personnel to select the various pulse output options after implant using radio frequency communications. While, in certain embodiments, the system employs fully implanted elements, systems employing partially implanted elements may also be used in accordance with the teachings provided herein.

In one illustrative, but non-limiting system, a control module is operably coupled to a signal generation module and instructs the signal generation module regarding the signal to be generated. For example, at any given time or period of time, the control module may instruct the signal generation module to generate an electrical signal having a specified pulse width, frequency, intensity (current or voltage), etc. The control module may be preprogrammed prior to implantation or receive instructions from a programmer (or another source) through any known or future developed mechanism, such as telemetry. The control module may include or be operably coupled to memory to store instructions for controlling the signal generation module and may contain a processor for controlling which instructions to send to signal generation module and the timing of the instructions to be sent to signal generation module.

In certain embodiments, the controller alters and/or modulates respiration adjusting the respiration rate and/or tidal volume in response to the subject's heart rate and/or in response to variations in the measured respiration rate and/or tidal volume.

In various embodiments, leads are operably coupled to signal generation module such that a stimulation pulse generated by signal generation module may be delivered via electrodes.

While in certain embodiments, two leads are utilized, it will be understood that any number of one or more leads may be employed. In addition, it will be understood that any number of one or more electrodes per lead may be employed. Stimulation pulses are applied to electrodes (which typically are cathodes) with respect to a return electrode (which typically is an anode) to induce a desired area of excitation of electrically excitable tissue in a region of the cervical spine. A return electrode such as a ground or other reference electrode can be located on same lead as a stimulation electrode. However, it will be understood that a return electrode may be located at nearly any location, whether in proximity to the stimulation electrode or at a more remote part of the body, such as at a metallic case of a pulse generator. It will be further understood that any number of one or more return electrodes may be employed. For example, there can be a respective return electrode for each cathode such that a distinct cathode/anode pair is formed for each cathode.

In various embodiments, the independent electrodes or electrodes of electrode arrays are operably linked to control circuitry that permits selection of electrode(s) to activate/stimulate and/or controls frequency, and/or pulse width, and/or amplitude of stimulation. In various embodiments, the electrode selection, frequency, amplitude, and pulse width are independently selectable, e.g., at different times, different electrodes can be selected. At any time, different electrodes can provide different stimulation frequencies and/or amplitudes. In various embodiments, different electrodes or all electrodes can be operated in a monopolar mode and/or a bipolar mode, using, e.g., constant current or constant voltage delivery of the stimulation.

In one illustrative but non-limiting system a control module is operably coupled to a signal generation module and instructs the signal generation module regarding the signal to be generated. For example, at any given time or period of time, the control module may instruct the signal generation module to generate an electrical signal having a specified pulse width, frequency, intensity (current or voltage), etc. The control module may be preprogrammed prior to use or receive instructions from a programmer (or another source). Thus, in certain embodiments the pulse generator/controller is configurable by software and the control parameters may be programmed/entered locally, or downloaded as appropriate/necessary from a remote site.

In certain embodiments the pulse generator/controller may include or be operably coupled to memory to store instructions for controlling the stimulation signal(s) and may contain a processor for controlling which instructions to send for signal generation and the timing of the instructions to be sent.

While in certain embodiments, two leads are utilized to provide transcutaneous or epidural stimulation, it will be understood that any number of one or more leads may be employed. In addition, it will be understood that any number of one or more electrodes per lead may be employed. Stimulation pulses are applied to electrodes (which typically are cathodes) with respect to a return electrode (which typically is an anode) to induce a desired area of excitation of electrically excitable tissue in one or more regions of the spine. A return electrode such as a ground or other reference electrode can be located on same lead as a stimulation electrode. However, it will be understood that a return electrode may be located at nearly any location, whether in proximity to the stimulation electrode or at a more remote part of the body, such as at a metallic case of a pulse generator. It will be further understood that any number of one or more return electrodes may be employed. For example, there can be a respective return electrode for each cathode such that a distinct cathode/anode pair is formed for each cathode.

In certain embodiments the controller component of the electrical stimulator is configured to receive signals from a heart rate monitor and/or respiration monitor and to adjust respiration parameters in response to changes in heart rate and/or respiration patterns.

Magnetic Stimulators.

Magnetic nerve stimulators are well known to those of skill in the art. Stimulation is achieved by generating a rapidly changing magnetic field to induce a current at the nerve of interest. Effective nerve stimulation typically requires a current transient of about $10^8$ A/s. In certain embodiments this current is obtained by switching the current through an electronic switching component (e.g., a thyristor or an insulated gate bipolar transistor (IGBT)).

FIG. 1 schematically shows one illustrative, but non-limiting embodiment of a magnetic stimulator. As shown therein, magnetic nerve stimulator 100 comprises two parts: a high current pulse generator producing discharge currents of, e.g., 5,000 amps or more; and a stimulating coil 110 producing magnetic pulses (e.g., with field strengths up to 4, 6, 8, or even 10 tesla) and with a pulse duration typically ranging from about 100 μs to 1 ms or more, depending on the stimulator type. As illustrated in FIG. 1, a voltage (power) source 102 (e.g., a battery) charges a capacitor 106 via charging circuitry 104 under the control of control circuitry 114 (e.g., a microprocessor) that accepts information such as the capacitor voltage, power set by the user, and various safety interlocks 112 within the equipment to ensure proper operation, and the capacitor is then connected to the coil via an electronic switching component 108 when the stimulus is to be applied. The control circuitry is operated via a controller interface 116 that can receive user input and/optionally signals from external monitors such as optional heart rate monitors 118 and/or optional or respiration monitors 120 and adjust stimulus parameters in response to variations/changes in those signals.

When activated, the discharge current flows through the coils inducing a magnetic flux. It is the rate of change of the magnetic field that causes the electrical current within tissue to be generated, and therefore a fast discharge time is important to stimulator efficiency.

As noted earlier the magnetic field is simply the means by which an electrical current is generated within the tissue, and that it is the electrical current, and not the magnetic field, that causes the depolarization of the cell membrane and thus the stimulation of the target nerve.

Since the magnetic field strength falls off with the square of the distance from the stimulating coil, the stimulus strength is at its highest close to the coil surface. The stimulation characteristics of the magnetic pulse, such as depth of penetration, strength and accuracy, depend on the rise time, peak electrical energy transferred to the coil and the spatial distribution of the field. The rise time and peak coil energy are governed by the electrical characteristics of the magnetic stimulator and stimulating coil, whereas the spatial distribution of the induced electric field depends on the coil geometry and the anatomy of the region of induced current flow.

The stimulating coils typically consist of one or more well-insulated copper windings, together with temperature sensors and safety switches.

In certain embodiments the use of single coils is contemplated. Single coils are effective in stimulating the human motor cortex and spinal nerve roots. To date, circular coils with a mean diameter of 80-100 mm have remained the most widely used magnetic stimulation. In the case of circular coils the induced tissue current is near z on the central axis of the coil and increases to a maximum in a ring under the mean diameter of coil.

A notable improvement in coil design has been that of the double coil (also termed butterfly or figure eight coil). Double coils utilize two windings, normally placed side by side. Typically double coils range from very small flat coils to large contoured versions. The main advantage of double coils over circular coils is that the induced tissue current is at its maximum directly under the center where the two windings meet, giving a more accurately defined area of stimulation.

The stimulating pulse may be monophasic, biphasic or polyphasic. Each of these has its own properties and so may be useful in particular circumstances. For neurology, single pulse, monophasic systems are generally employed; for rapid rate stimulators, biphasic systems are used as energy must be recovered from each pulse in order to help fund the next. Polyphasic stimulators are believed to have a role in a number of therapeutic applications.

Descriptions of magnetic nerve stimulators can be found, inter alia, in U.S. patent publications US 2009/0108969 A1, US 2013/0131753 A1, US 2012/0101326 A1, IN U.S. Patent Nos: U.S. Pat. Nos. 8,172,742, 6,086,525, 5,066,272, 6,500, 110, 8,676,324, and the like. Magnetic stimulators are also commercially availed from a number of vendors, e.g., MAGVENTURE®, MAGSTIM®, and the like.

Respiration Stimulation/Maintenance Systems.

Figure 2:
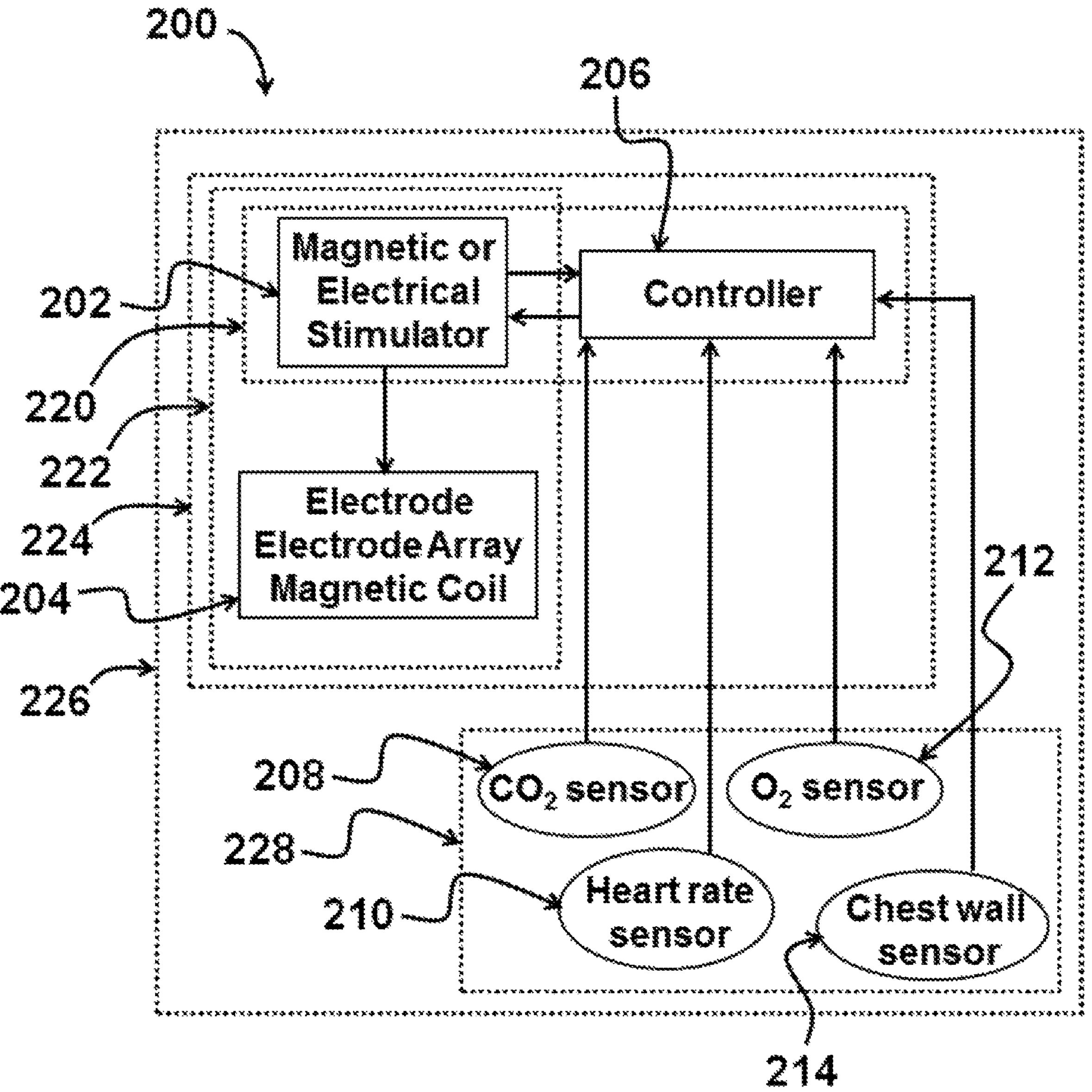
FIG. 2 schematically illustrates one embodiment of a respiratory stimulation/maintenance system as described herein.

In certain embodiments, respiration stimulation/maintenance systems are contemplated. One illustrative, but non-limiting embodiment is shown in FIG. 2. As shown therein the system 200 typically comprises an electrical or magnetic stimulator configured to induce epidural and/or transcutaneous electrical stimulation and/or magnetic stimulation. The electrical stimulation is delivered to a region of the cervical spine (e.g., C0 to C8 or a region therein) via a transcutaneous electrode, an epidural electrode (e.g., an epidural electrode array), or one or more magnetic coils 204. In various embodiments a controller 206 regulates the stimulation parameters produced by the stimulator. In certain embodiments, the controller can be a unit or module that is separate from the stimulator, while in other embodiments in certain embodiments, the controller and stimulator can be integrated (as illustrated by dashed box 220). In various embodiments the system typically also comprises one or more sensors. Illustrative, but non-limiting examples of sensors include an oxygen sensor 212, a $CO_2$ sensor 208, a chest wall expansion/movement sensor 214, a heart rate sensor 210, and the like. Typically, the output of the sensor (s) is coupled to the stimulator/controller so that the controller/stimulator adjust the stimulation pattern in response to the sensor output to provide a desired tidal volume and/or $O_2$ saturation and/or end tidal $CO_2$.

In certain embodiments the sensors are provided as integral components of the system. In other embodiments, the sensors are provided as instrumentation, e.g. in an acute care/intensive care unit, an emergency room, an operating room, etc.

In certain embodiments where a transcutaneous or magnetic stimulation is utilized the stimulator and associate coil/electrode can be external to the subject. Additionally, the other components of the system controller and various sensors can also be external.

In certain embodiments various components of the system are implantable into the subject (e.g., patient). Thus, for example, as indicated by dashed box 228 one or more of the sensors can be implantable sensors. In certain embodiments the electrode or coil 204 can be implanted while the stimulator and/or controller are external to the subject (as indicated by dashed box 222). In certain embodiments the controller 206 and/or the stimulator 202 and the electrode or coil 204 are all implanted into the subject (as indicated by dashed box 224). In certain embodiments the entire system is implanted into the subject (as indicated by dashed box 226).

In certain embodiments the system comprises an implanted (e.g., surgically implanted), closed loop epidural stimulation device for spinal cord injured, stroke subjects, ALS patients with respiratory issues, and the like.

In certain embodiments the system comprises a temporary implanted device by percutaneous insertion of leads for ICU/acute care patients with acute respiratory failure to restore respiratory function or facilitate vent weaning. Such a system can provide a feedback mechanism assessing chest wall movement, $O_2$ saturation, end tidal $CO_2$ (all of which can be implemented in an acute care, e.g., ICU bed setting) which adjusts the stimulation parameters.

In certain embodiments the system comprise a magnetic or transcutaneous electrical stimulation device for SIDS or ICU patients with decreased respiratory drive and can provide a feedback mechanism that monitors chest expansion, and/or $O_2$ saturation, and/or $CO_2$ ($pCO_2$) and uses this information to adjust stimulation parameters.

Sensors for detecting a variety of physiological parameters including, but not limited to $O_2$ saturation, $pCO_2$, chest wall movement, heart rate and the like are well known to those of skill in the art. For example external and implantable oximeters can routinely determine $O_2$ saturation. A typical pulse oximeter utilizes an electronic processor and a pair of small light-emitting diodes facing a photodiode through a translucent part of the subject's body, typically a fingertip or an earlobe. In one illustrative, but non-limiting embodiment, one LED is red, e.g., with a wavelength of about 660 nm, and the other is infrared, e.g., with a wavelength of about 940 nm. Absorption of light at these wavelengths differs significantly between blood loaded with oxygen and blood lacking oxygen. Oxygenated hemoglobin absorbs more infrared light and allows more red light to pass through. Deoxygenated hemoglobin allows more infrared light to pass through and absorbs more red light. The LEDs sequence through their cycle of one on, then the other, then both off, e.g., about thirty times per second which allows the photodiode to respond to the red and infrared light separately and also adjust for the ambient light baseline. The amount of light that is transmitted is measured, and separate normalized signals are produced for each wavelength. These signals fluctuate in time because the amount of arterial blood that is present increases (literally pulses) with each heartbeat. By subtracting the minimum transmitted light from the peak transmitted light in each wavelength, the effects of other tissues are corrected for. The ratio of the red light measurement to the infrared light measurement is then calculated by the processor (which represents the ratio of oxygenated hemoglobin to deoxygenated hemoglobin), and this ratio is then converted to $SpO_2$ e.g., by a processor via a lookup table based on the Beer-Lambert law. External oximeters are commercially available and are routinely available in acute care settings (e.g., emergency room, ICU, operating rooms, etc.).

Implantable oximeters function in a similar manner. The implantable oximeter typically includes a light emitting diode, that transmits light into blood passing the sensor, and a phototransistor that senses the light after it has passed through the blood. Blood SO2 is then derived from a comparison of the intensity and frequency of the emitted light and the received light. Depending upon the implementation, an optical measurement window of the phototransistor of the sensor is either positioned within the blood stream (such as within one of the chambers of the heart) or is positioned near a blood vessel (e.g., subcutaneously).

Implantable oximeters are known to those of skill in the art. See, for example, U.S. Pat. No. 8,099,146 B1 and the references cited therein.

Capnography is the monitoring of the concentration or partial pressure of carbon dioxide ($CO_2$). A capnogram is a direct monitor of the inhaled and exhaled concentration or partial pressure of $CO_2$, and an indirect monitor of the $CO_2$ partial pressure in the arterial blood. Capnographs usually work on the principle that $CO_2$ absorbs infrared radiation. A beam of infrared light is passed across the gas sample to fall on a sensor. The presence of $CO_2$ in the gas leads to a reduction in the amount of light falling on the sensor, which changes the voltage in a circuit. The analysis is rapid and accurate. Capnographs are commercially available and routinely found in acute care settings (e.g., ICU, emergency room, operating rooms, etc.). One illustrative capnograph is the Micro-Capnograph produced by Linton Instrumentation, Inc.

In certain embodiments $pCO_2$ can be Measured using a transcutaneous monitor (e.g., available from Radiometer America, and the like).

PC02 can also be measured using an implantable $CO_2$ sensor (see, e.g, Čajlaković et al. (2012), *Optochemical Sensor Systems for In-Vivo Continuous Monitoring of Blood Gases in Adipose Tissue and in Vital Organs*, pages 63-88 in Chemical Sensors, Wen Wang, ed., InTech.).

Sensors for measuring/monitoring chest wall expansion and/or movement are also well known to those of skill in the art. For example, rib cage movement can be measured with an inductance or strain gage band placed around the rib cage, e.g., immediately below the axillae. In the case of an inductance band, chest expansion can be determined by changes in the inductance of the band induced by stretching of the band (see. e.g., Drummond et al. (1996) *Br. J. Anaesthesia,* 77: 327-332). Similarly in a strain gage band, changes in resistance/conductance of the strain gages produced by band expansion/contraction can readily be measured using methods known to those of skill in the art.

In another illustrative, but non-limiting embodiment, chest wall expansion and/or movement can be monitored by measuring thoracic impedance, e.g., as described by Drummond et al. (1996) *Br. J. Anaesthesia,* 77: 327-332.

In another illustrative, but non-limiting embodiment, chest wall expansion and/or movement can be monitored using a laser, e.g., as described by Kondo et al. (1997) *Eur. Respir. J.* 10: 1865-1869.

In certain embodiments chest wall position/movement can be monitored using an accelerometer. In various embodiments the accelerometer can be attached to the surface of the body, while in other embodiments, the accelerometer can be implanted within the body. Implantable and surface accelerometers configured for the detection of chest wall motion are described, for example, in U.S. Patent Pub. No: 2013/0085404.

It will be noted that these particular systems and sensors are illustrative and non-limiting. Using the teachings provided herein, numerous other systems will be available to one of skill in the art.

Self-Contained Respiratory Regulation Devices.

In certain embodiments self-contained, portable, respiratory regulation devices/systems are contemplated. In various embodiments the systems comprise a stimulator and an electrode for applying an electrical stimulus or a coil for applying a magnetic stimulus. The electrode and/or coil are configured for application of a stimulus to the cervical region of a subject to control and/or to induce respiration.

In one illustrative but non-limiting system a control module is operably coupled to stimulator and instructs the stimulator module regarding the signal to be generated. For example, at any given time or period of time, the control module may instruct the signal generation module to generate an electrical signal having a specified pulse width, frequency, intensity (current or voltage), etc. The control module may be preprogrammed prior to use or receive instructions from a programmer (or another source). Thus, in certain embodiments the pulse generator/controller is configurable by software and the control parameters may be programmed/entered locally, or downloaded as appropriate/necessary from a remote site.

In certain embodiments the pulse generator/controller may include or be operably coupled to memory to store instructions for controlling the stimulation signal(s) and may contain a processor for controlling which instructions to send for signal generation and the timing of the instructions to be sent.

In some embodiments the respiration control devices can be pre-programmed with desired stimulation parameters. In some instances, some or all parameters of the electrode may be controllable by the subject, e.g., without supervision by a physician. In other instances, some or all parameters of the electrode may be automatically controllable by a programmer or controller comprising the device.

Devices for neuromodulation of respiration can have a variety of configurations. In some instances, the device may be configured as a belt or strap having at least one electrode or coil operably attached thereto. Alternatively, the device may be configured as an adhesive patch having at least one electrode or coil operably attached thereto. The power source and/or stimulator can be integrally formed with, connected to the electrode(s) or coil(s). As noted, in certain instances the device can include a controller (as described above) that is configured, for example, to electronically communicate (e.g., wirelessly) with an electronic device (e.g., a PDA, cell phone, tablet, computer, etc.).

The device can be part of an open- or closed-loop system. In an open-loop system, for example, a physician or subject may, at any time, adjust treatment parameters, such as pulse amplitude, pulse-width, pulse frequency, duty cycle, etc. In certain embodiments this open loop can be used in conjunction with ventilator device during weaning off the ventilator. In certain embodiments it can be coupled or built into ventilator control with values from the ventilator (tidal volume, PEEP, frequency) fed back into the stimulation control unit, processed and stimulation algorithm implemented for stimulation.

Alternatively, in a closed-loop system, treatment parameters (e.g., electrical signals) may be automatically adjusted in response to a sensed physiological parameter or a related symptom indicative of the extent of respiration. In a closed-loop feedback system, a sensor that senses a physiological parameter associated with respiration (e.g., that senses heart rate, tidal volume, etc.) can be utilized.

It should be appreciated that incorporating the therapy delivery device as part of a closed-loop system can include placing a therapy delivery device on or within a mammal at a nerve target, sensing a physiological parameter associated with respiratory function, and then activating the delivery device to apply a signal to adjust the respiration parameters in response to the sensor signal.

Use of Neuromodulatory Agents.

In certain embodiments, the transcutaneous and/or epidural and/or magnetic stimulation methods described herein are used in conjunction with various pharmacological agents, particularly pharmacological agents that have neuromodulatory activity (e.g., are monoamergic). In certain embodiments, the use of various serotonergic, and/or dopaminergic, and/or noradrenergic, and/or GABAergic, and/or glycinergic drugs is contemplated. These agents can be used in conjunction with epidural stimulation and/or transcutaneous stimulation and/or magnetic stimulation as described above. This combined approach can help to put the spinal cord (e.g., the cervical spinal cord) in an optimal physiological state for controlling respiration.

In certain embodiments, the drugs are administered systemically, while in other embodiments, the drugs are administered locally, e.g., to particular regions of the spinal cord. Drugs that modulate the excitability of the spinal neuromotor networks include, but are not limited to combinations of noradrenergic, serotonergic, GABAergic, and glycinergic receptor agonists and antagonists.

Dosages of at least one drug or agent can be between about 0.001 mg/kg and about 10 mg/kg, between about 0.01 mg/kg and about 10 mg/kg, between about 0.01 mg/kg and about 1 mg/kg, between about 0.1 mg/kg and about 10 mg/kg, between about 5 mg/kg and about 10 mg/kg, between about 0.01 mg/kg and about 5 mg/kg, between about 0.001 mg/kg and about 5 mg/kg, or between about 0.05 mg/kg and about 10 mg/kg.

Drugs or agents can be delivery by injection (e.g., subcutaneously, intravenously, intramuscularly), orally, rectally, or inhaled.

Illustrative pharmacological agents include, but are not limited to, agonists and antagonists to one or more combinations of serotonergic: 5-HT1A, 5-HT2A, 5-HT3, and 5HT7 receptors; to noradrenergic alpha 1 and 2 receptors; and to dopaminergic D1 and D2 receptors (see, e.g., Table 1).

TABLE 1

Illustrative pharmacological agents.

| Name | Target | Action | Route | Typical Dose (mg/Kg) | Typical Range (mg/kg) |
|---|---|---|---|---|---|
| Serotonergic receptor systems | | | | | |
| 8-OHDPAT | 5-HT1A7 | Agonist | S.C. | 0.05 | 0.045-0.3 |
| Way 100.635 | 5-HT1A | Antagonist | I.P. | 0.5 | 0.4-1.5 |
| Quipazine | 5-HT2A/C | Agonist | I.P. | 0.2 | 0.18-0.6 |
| Ketanserin | 5-HT2A/C | Antagonist | I.P. | 3 | 1.5-6.0 |
| SR 57227A | 5-HT3 | Agonist | I.P. | 1.5 | 1.3-1.7 |
| Ondanesetron | 5-HT3 | Antagonist | I.P. | 3 | 1.4-7.0 |
| SB269970 | 5-HT7 | Antagonist | I.P. | 7 | 2.0-10.0 |
| Noradrenergic receptor systems | | | | | |
| Methoxamine | Alpha1 | Agonist | I.P. | 2.5 | 1.5-4.5 |
| Prazosin | Alpha1 | Antagonist | I.P. | 3 | 1.8-3.0 |
| Clonidine | Alpha2 | Agonist | I.P. | 0.5 | 0.2-1.5 |
| Yohimbine | Alpha2 | Antagonist | I.P. | 0.4 | 0.3-0.6 |
| Dopaminergic receptor systems | | | | | |
| SKF-81297 | D1-like | Agonist | I.P. | 0.2 | 0.15-0.6 |
| SCH-23390 | D1-like | Antagonist | I.P. | 0.15 | 0.1-0.75 |
| Quinipirole | D2-like | Agonist | I.P. | 0.3 | 0.15-0.3 |
| Eticlopride | D2-like | Antagonist | I.P. | 1.8 | 0.9-1.8 |

The foregoing methods are intended to be illustrative and non-limiting. Using the teachings provided herein, other methods involving transcutaneous electrical stimulation and/or epidural electrical stimulation and/or magnetic stimulation and/or the use of neuromodulatory agents to improve, and/or regulating, and/or restore respiration in a subject with a respiratory deficiency will be available to one of skill in the art.

EXAMPLES

The following examples are offered to illustrate, but not to limit the claimed invention.

Example 1

FIGS. 14 and 15 were obtained during a cervical spinal surgery in which the posterior elements (lamina and spinous process) of the spinal column was removed exposing the epidural space demonstrate the proof-of-concept in using epidural electrical stimulation to modulate respiration in humans (see, e.g., FIG. 11).

Monopolar ball-tipped electrodes were placed on top of the epidural space at different cervical locations (see, e.g., FIG. 11, panel C), frequency, and amplitude with pulse width of 450 us. FIG. 14 shows that stimulation at a frequency of 30 Hz at C3/4 can induce respiration during deep anesthesia in humans. Electrical stimulation of the dorsal cord at C3/4 resulted in diaphragm EMG bursts and productive inhalation. This result indicates that the spinal cord stimulation can generate physiological respiratory/lung function.

FIG. 15 shows that stimulation at a frequency of 30 Hz at C3/4 can induce coordinated respiration during off-state in humans. This observation indicates that accessible regions of the spinal cord can allow for coordinated respiratory/lung function following dysfunction or loss of connectivity with brainstem respiratory centers.

Example 2

Modulation of Respiratory Output by Cervical Epidural Stimulation in the Anesthetized Mouse Abstract Respiration is produced and controlled by well-characterized brainstem nuclei, but the contributions of spinal circuits to respiratory control and modulation remain under investigated. Many respiratory studies are conducted in in vitro preparations (e.g., brainstem slice) obtained from neonatal rodents. While informative, these studies do not fully recapitulate the complex afferent and efferent neural circuits that are likely to be involved in eupnea (i.e., quiet breathing). To begin to investigate spinal contributions to respiration, we electrically stimulated the cervical spinal cord during unassisted respiration in anesthetized, intact mice. Specifically, we used epidermal electrical stimulation at 20 Hz and varied current intensity to map changes in respiration. Stimulating at 1.5 mA at cervical level 3 (C3) consistently caused a significant increase in respiratory frequency compared to pre-stimulation baseline and when compared to sham stimulations. The increase in respiratory frequency persisted for several minutes after epidural stimulation ceased. There was no change in tidal volume. Sigh frequency also increased during epidural stimulation at C3. Neither the increase in respiratory frequency nor the increase in sighing was observed at other dorsal cervical levels. Increasing electrical stimulus intensity did not increase respiration frequency or increase the duration of increased respiration frequency, which suggests that the spinal circuits involved in the modulation of eupnea and sighing may be preferentially activated by specific endogenous inputs. These findings also suggest that the cervical spinal cord can play a role in respiratory modulation that affects both eupneic respiration and sigh production in intact, adult mice.

Introduction

The mammalian respiratory system is controlled by a complex network of neurons interconnected among several nuclei located in the brainstem. The origin of the respiratory rhythm has been attributed to the pre-Botzinger Complex (preBotC) located in the ventral medulla (Feldman et al. (1990) *Am. J. Physiol.* 259: R879-886; Onimaru et al. (2009) *Resp. Physiol. Neurobiol.,* 168: 13-18; Smith et al. (1991) *Science* 254: 726-729) and the parafacial respiratory group (pFRG) located in the rostro-ventrolateral medulla (Duffin (2004) *Exp. Physiol.,* 89: 517-529; Onimaru et al. (2006) *J. Neurophysiol.,* 96: 55-61). Pontine nuclei also seem important for generating the eupneic rhythm (Lindsey et al. (2012) *Compr. Physiol.,* 2: 1619-1670; St. John and Paton (2004) *Respir. Physiol. Neurobiol.* 143: 321-332). The rhythm generating elements within the pons and medulla are intimately interconnected and embedded within neuron groups that shape the pattern of the respiratory output. Thus, within this larger respiratory central pattern generator, there are individual rhythm generating elements that come into play in a variety of different circumstances. Among the key structures for respiratory control are the ventral respiratory column (VRC), pontine respiratory group (PRG) and dorsal respiratory group (DRG) (Lindsey et al. (2012) *Compr. Physiol.,* 2: 1619-1670). This network of neurons in turn activates the motor neurons of respiratory muscles in a highly choreographed sequence, which leads to remarkably stable and well-coordinated inspiratory and expiratory flow during activities as diverse as quiet eupnea, speech and vigorous exercise (Bartlett and Leiter J C (2011) *Compr. Physiol.* 2: 1387-1415). The respiratory central pattern generator (CPG) may overlap and coordinate with other CPGs so that the respiratory pattern may be involved in or encompassed within a variety of other activities, such as swallowing, coughing and sighing.

Speculation about the existence of spinal respiratory neurons with rhythmic properties in the spinal cord was raised when inspiratory unit activities were recorded in C1-C2 segments of transected cats (Aoki et al. (1980) *Brain Res.* 202: 51-63), and it believed that there are inspiratory neurons found in the upper cervical cord (Duffin and Hoskin (1987) *Brain Res.* 435: 351-354; Hoskin and Duffin (1987) *Exp. Neurol.,* 95: 126-141; Hoskin and Duffin (1987) *Exp. Neurol.,* 98: 404-417; Lipski and Duffin (1986) *Exp. Brain Res.* 61: 625-637). A study using an in vitro preparation of the neonatal mouse brainstem-spinal cord has shown that spontaneous rhythmic respiratory burst activity can be generated in the cervical ventral roots of C1/C2 and C4 following transection of the spinal cord above C1 (Kobayashi et al. (2010) *J. Physiol. Sci.* 60: 303-307).

To date, studies that have identified cervical spinal cord involvement in respiratory function have used in vitro testing (Aoki et al. (1980) *Brain Res.* 202: 51-63; Dubayle and Viala (1996) *Neuroreport* 7: 1175-1180; Duffin and Hoskin (1987) *Brain Res.* 435: 351-354; Kobayashi et al. (2010) *J. Physiol. Sci.* 60: 303-307). To gain a better understanding of the role of the upper cervical spinal cord in respiration, we examined the effect of electrical stimulation on respiratory activity in intact anesthetized mice. We applied direct, constant current stimulation to the epidural surface of the exposed spinal cord from the most caudal region of the medulla (C0) through C1 to C5 and recorded the respiratory output. The aim of our study was (1) to identify a stimulation intensity required to evoke a respiratory response and (2) to determine if there were an optimal cervical regions to stimulate in order to increase respiratory activity in healthy adult mice. Our results showed that epidural stimulation at the C3 level of the spinal cord with 1.5 mA increased the respiratory rate and the sigh frequency, but did not change the tidal volume in anesthetized mice. Our findings show that respiratory function, possibly involving two respiratory related CPGs—eupnea and sighing, can be altered by stimulation of the cervical spinal cord if the appropriate stimulation intensity and location are used.

Methods

Animals

Mixed gender 5-month-old C57BL/6 mice were used in this study. All mice were kept and tested according to protocols approved by Animal Research Committee (ARC) at University of California, Los Angeles. All procedures were conducted on mice anesthetized by isoflurane. All mice were subjected to sham and monopolar electric epidural stimulations of the spinal cord.

Laminectomy

To perform the laminectomy, the animal was placed under anesthesia and spread prone on a surgical pad. The laminae from the C1 to C6 vertebral levels were gently removed to expose the spinal cord with intact dura matter. Gauze pads soaked in mineral oil were placed on top of the spinal cord to keep it moist, and the dorsal skin on either side of the wound was carefully clipped together with surgical clips to keep the gauze in place. The animal was then positioned for a tracheostomy and intubation.

Tracheostomy and Intubation

Respiratory flows were measured in anesthetized and tracheostomized mice. The tracheostomy and intubation methods were adapted from the protocol described by Moldestad et al. (2009) *J. Neurosci. Meth.* 176: 57-62. Briefly, a 50~60 mm intravenous catheter (Venflon Pro. BD, 18-20 GA, BD, NJ, USA) was inserted gently between two tracheal rings, and its position was secured by super glue. The animal was observed for 5 min to detect any possible respiratory problems before the super glue completely solidified. Finally, the animal was connected to a pneumotachograph and moved into position for epidural stimulation (see FIG. 5, panel A). Epidural electrical stimulation protocol FIG. 5, panel B, shows the dorsal spinal surface after the laminectomy, and FIG. 5, panel C, illustrates the epidural stimulation protocol at each cervical level. This protocol was used in all the studies reported here. Pre-sham-baseline respiratory activity was recorded for 2 min, followed by sham epidural stimulation. To conduct the sham stimulation, the electrodes were gently pressed onto the epidural surface of the spinal cord for 30 s with no current applied. The post-sham-baseline was recorded immediately after for 3 min. The pre-stimulation baseline was then recorded for a further 3 min followed by a 30 s electrical stimulation. Finally, a 5 min post-stimulation baseline was recorded. The same sequence of sham and active epidural stimulation was repeated on the next cervical level in a randomized sequence (C0-C5).

Testing for Electrical Stimulation Intensity and Location in Cervical Spinal Cord to Evoke a Respiratory Response.

We first carried out a study to determine if there were suitable intensities and cervical spinal cord levels to evoke a respiratory response in the anesthetized mouse. In this study, 13 mice were used. We tested the brainstem (C0) and C1 to C5 cervical levels with stimulus strengths of 0.3 mA, 0.9-1.0 mA and 1.5 mA using a constant current stimulator. For this study, all the stimulations were performed along the dorsal medial-lateral surface of the spinal cord, and all spinal cord levels were tested bilaterally in a randomized manner. A constant stimulation frequency of 20 Hz and monophasic electrical stimulation, 1% duty cycle and square wave pulse pattern were used in this study. The ground was placed on the spinal cord 1 mm away from the stimulation electrode for these monopolar stimulations.

Cervical C3 Stimulation to Examine Changes in Respiratory Response

After the optimal stimulation intensity and cervical level were determined (see results section), a separate study was conducted to examine whether stimulation at each cervical level was sufficient to evoke a respiratory response. A total of 24 mice were used in this study. A laminectomy from C1 to C6 was performed as described above, and all animals were tested using the epidural stimulation protocol as described previously.

Physiological Recordings

For all the studies, diaphragmatic electromyographic (EMG) recordings were carried out. A 3-cm incision was made at the base of the rib cage to expose the abdominal surface of the diaphragm. Monopolar electrodes were inserted medially into the diaphragm, and EMG muscle activity was recorded. The EMG recording wires were connected to an amplifier, and the EMG signal was band-pass filtered between 30 and 3,000 Hz and digitized at 10 KHz. An amplifier (3000 AC/DC Differential Amplifier, AM system, Carlsborg, WA), an A/D board (DT1890, Data Translation Inc., Marlboro, MA) and a data analysis software system (DataView, St. Andrew University) were used to record the EMG signals for subsequent analysis.

Data Collection

The respiratory patterns as well as vital physiological variables (heart rate, peripheral oxygen saturation, respiration rate, and body temperature) of tested animals were monitored throughout the whole test using the PhysioSuite™ system (Kent Scientific). The respiratory flow was monitored through a pneumotachograph and pressure transducer (Biopac Systems, Inc., Goleta, CA) and recorded on a computer using DataView (University of St Andrews). The digitization rates of all the channels were 10 KHz.

Data Analysis.

For each round of sham and stimulation recording, the data used for analysis were as follows: 1 min pre-sham, 30 sec sham, 3 min post-sham, 1 min pre-stimulation, 30 sec stimulation and 3 min post-stimulation. The respiratory frequency and peak-to-peak amplitude (tidal volume) were extracted. The extracted data were de-noised with a running average filter (time constants=250 ms), normalized (rectified and smoothed with a Gaussian filter) and visualized through MATLAB (MathWorks, Natick, MA). The analyzed data were presented as a ratio comparing sham to pre-sham, post-sham to pre-sham, stimulation to pre-stimulation, and post-stimulation to pre-stimulation. These data were also used to analyze the occurrence of sighs. Sighs have a characteristic flow morphology and are followed by a brief expiratory pause. Sighs were typically about twice the volume of a normal breath (3). Sigh data were presented as the absolute number of sighs and absolute frequency. Patterns of sigh and eupnea frequency response for each mouse tested were compared to each other to examine if there was a correlation between the sigh response and the eupneic response to epidural stimulation.

The response to epidural stimulation at any spinal level differed among animals. In order to objectively categorize the different patterns of responses, we employed cluster analysis, which can be used to systematically and hierarchically categorize data based on the mathematical similarity of the responses. We performed the hierarchical cluster (Hclust) analysis using R software (www.r-project.org) where each trace of the ratio of respiratory activity during stimulation was compared to baseline respiratory activity over time. Hclust uses a distance matrix based on dissimilarity (calculated as the square root of sum of squares of differences in particular attributes) and estimates the Euclidean distance between different data sets (respiratory frequency responses to epidural stimulation in our case). The greater the distance between two patterns of response, the greater the difference in the shape of each trace of respiratory frequency ratios.

For our analysis, we analyzed each point on the ratio of respiratory frequency at 0.25 secs intervals to estimate the differences among frequency responses among animals. If the calculated distance was smaller than 7.5 hierarchical units, the recording was considered to be in the same cluster. If the distance was larger than 7.5 hierarchical units, the recording was placed in a separate cluster. The distance cut-off of 7.5 was validated post-hoc by checking the standard error of the mean within clusters as well as through checking the correlation within and between the clusters. The Kendall Rank Coefficient test and Kendall's Tau-b were used for correlation validation. Both tests are used to test whether the variables within each cluster are truly different. Different cut-off values (2.5, 5, 7.5, 10 and 12.5) were tested with these two tests, and 7.5 was the minimum distance for the variables to achieve correlation validation.

Statistics.

A one-way, repeated measures ANOVA was used for all data analyses. If the ANOVA indicated that significant differences existed among treatments, pre-planned paired comparisons were made using p-values adjusted by the Bonferroni method. In all cases, $p<0.05$ was considered statistically significant.

Results

Optimization of Current Intensities

Figure 6:
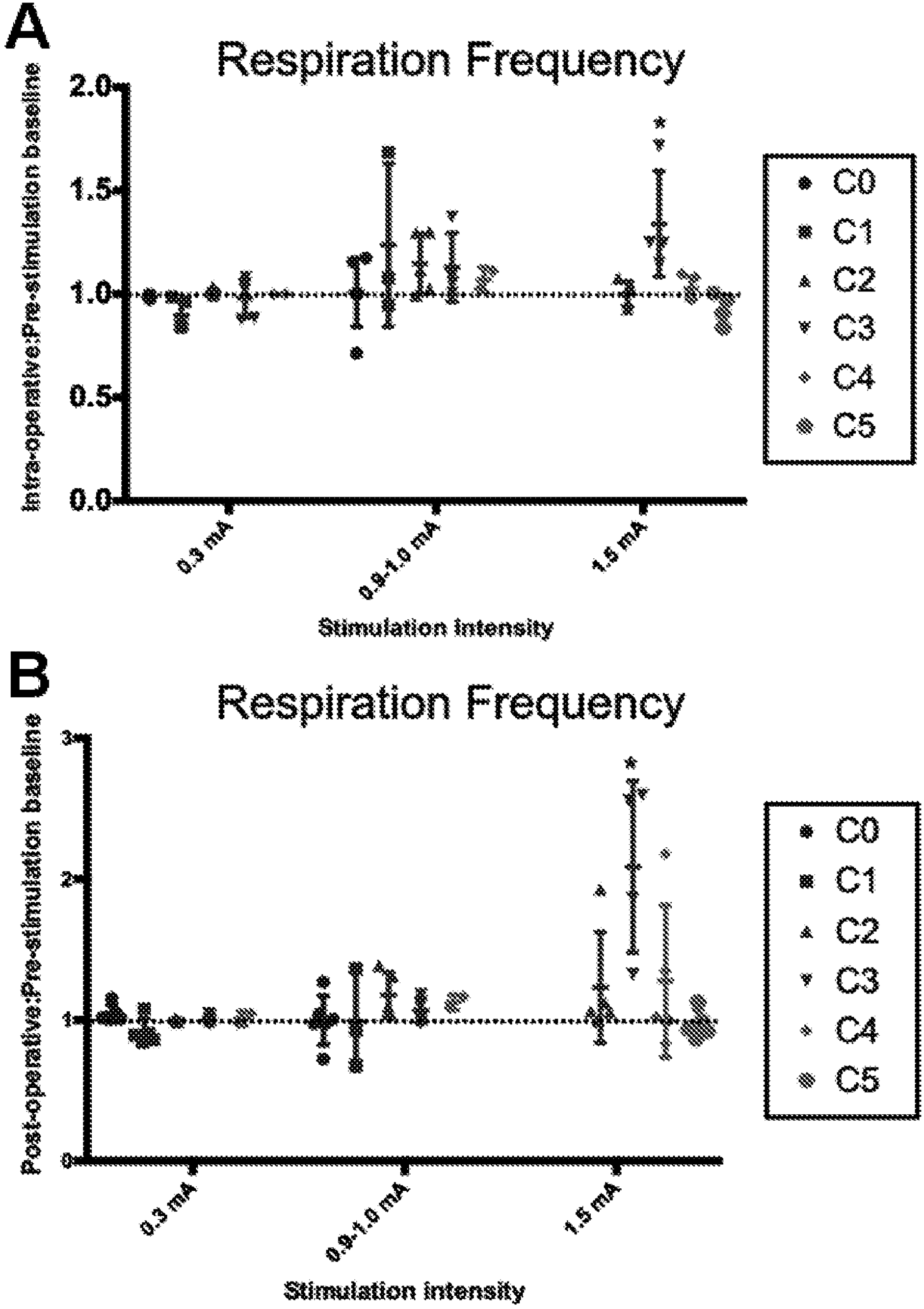
FIG. 6, panels A-B, shows the determination of the current intensity to use for each cervical level tested. The electrical stimulation intensities used were 0.3, 0.9-1.0 or 1.5 mA. Panel A: The respiratory frequency ratio of intra-operative recording compared to the pre-stimulation baseline is shown, and (Panel B) the respiration frequency ratio of post-stimulation recording compared to the pre-stimulation baseline is shown. In both analyses, the stimulation intensity of 1.5 mA at C3 caused the only significant increase in the respiratory ratio (see *). For C0 and C1, the stimulation intensity of 1.5 mA was too strong and induced cardiac arrest. For C5, only 1.5 mA was tested as the location was close to a major blood vessel that impeded the recording.

Systematic stimulation of the brainstem (C0) and C1 to C5 cervical levels using different current intensity was carried out to identify the optimal stimulation intensity and cervical level required to elicit a respiratory response. At C0 and C1, there were no changes in respiratory frequency when 0.3 and 1.0 mA stimulation were used (FIG. 6). Stimulation at 1.5 mA induced cardiac arrest, and therefore, this stimulation intensity was not continued at these cervical levels. Electrical stimulation at C2 and C4 at 0.3, 0.9-1.0 and 1.5 mA did not significantly increase respiration frequency (FIG. 6). At the C3 level, 0.3 and 1.0 mA stimulation did not affect the respiratory frequency. However, 1.5 mA stimulation at C3 significantly increased the respiratory frequency during the period of stimulation ($p=0.0387$). The increase in respiratory frequency also continued during the post-stimulation stages of recording even though stimulation had ceased (FIG. 6, see *; $p=0.0017$). Only 1.5 mA current intensity was tested at C5 as the location was close to a major blood vessel that impeded epidural stimulation. No respiratory change was observed at C5 using the 1.5 mA stimulation strength (FIG. 6).

Stimulation of C3 with 1.5 mA Increases Respiratory Frequency but not the Tidal Volume We determined that 1.5 mA at C3 was the optimal stimulation and location to elicit a change in respiratory frequency. Subsequently, we examined in-depth the frequency response elicited when C3 was stimulated with an electrical current of 1.5 mA. Our results show that there was a significant increase ($p<0.0001$) in the ratio of stimulated respiratory frequency compared to the sham stimulation (FIG. 7, panel A). The increase in respiratory frequency was seen during stimulation (see black arrow) and persisted in the post-stimulation phase (see red arrow). We only recorded for 3 min post-stimulation, and the duration of the facilitation of respiratory frequency may have persisted longer in some mice. We observed no significant change in the tidal volume of respiration when C3 was stimulated compared to the sham stimulation (FIG. 7, panel B). Our results indicate that cervical epidural stimulation can increase the number of breaths taken, but not the depth of each breath.

Hierarchical Cluster Analysis.

Using Hclust analysis we showed that the responses among animals could be grouped into different hierarchical clusters of respiratory responses when sham or epidural stimulation with 1.5 mA at C3 was carried out (FIG. 8, panels A, B). Twenty-three out of 24 of the sham stimulation responses belonged to the same cluster (FIG. 8, panel Ci). Only one of the 24 sham stimulation sequences fell into a different hierarchical cluster (FIG. 8, panel Cii), indicating that during sham stimulation, respiration was unchanging and similar across virtually all sham stimulation sequences in all of the animals. When epidural stimulation was used, six hierarchical clusters were identified (FIG. 8, panels D). The clusters differed in terms of the timing of the increase in respiratory frequency, and the persistence of the increase in respiratory frequency once epidural stimulation ceased. Clusters 1, 3, 4 and 6 contained 16 of the 24 animals studied (FIG. 8, panel D i, iii, iv and v), and these clusters shared two features: the respiratory rate rose during epidural stimulation and the respiratory rate remained elevated at some level above baseline after epidural stimulation had been turned off. These four clusters differed only in the variability or level of the changes in respiratory frequency. Cluster 2 contained 6 of the 24 animals studied (FIG. 4Dii), and in this cluster there was an initial increase in respiratory frequency that was not sustained after stimulation ceased. Cluster 5 contained 2 animals (FIG. 4Dv) in which epidural stimulation did not alter respiratory frequency, but respiratory frequency rose and was sustained after epidural stimulation ceased. The final cluster contained only 1 animal (FIG. 8, panel D vi) in which the respiratory frequency rose during epidural stimulation, and respiratory frequency was quite variable in the period following epidural stimulation. Even in clusters 2 and 5, all of the animals had some increase in respiratory frequency at some point during or immediately after epidural stimulation. In contrast, 23 of the 24 animals in the sham stimulation group had no discernible change in respiratory frequency.

Stimulation with 1.5 mA at C3 Increased the Number of Sighs

The number of sighs also increased significantly when mice received epidural stimulation of 1.5 mA at C3 compared to sham stimulation (FIG. 5; see *, p=0.0011). There was an increase in the number of sighs during stimulation compared to the pre-stimulation baseline (p=0.002), and also during the 3 mins post-stimulation compared to the pre-stimulation baseline (p<0.0001). Therefore, the number of sighs was elevated for up to 3 minutes after stimulation before returning to pre-stim baseline levels, but sighing diminished in many animals within 3 minutes after epidural stimulation stopped. These results differed from the eupneic respiratory frequency response where respiratory frequency was elevated for a more substantial part of the post-stimulation period and showed little evidence of abating in 18 of the 24 animals studied (clusters 1, 2, 4, 5 and 6).

No Correlation Between Patterns of Sigh and Eupnea Frequency when Stimulated with 1.5 mA at C3.

We assessed whether there was any correlation between the pattern of sigh and eupnea frequency responses after stimulation with 1.5 mA at C3. When each animal was stimulated, the pattern of sighing fell into one of four categories (much like the eupneic clusters). We simplified the categories of sigh and eupneic responses such that the categories included (1) no change during stimulation and no change after stimulation (only sighing clusters fulfilled these criteria), (2) no change during stimulation, but increased respiratory frequency post-stimulation (e.g., eupnea cluster, 5) (3) increased during stimulation, but without a sustained post-stimulation increase in respiratory frequency (e.g., cluster 3) and (4) increased during stimulation and sustained for some part of the post-stimulation period (e.g., all the remaining eupnea clusters). We compared the sigh response pattern and the eupnea response patterns of each mouse during and after epidural stimulation and found no correlation between the pattern of frequency change of eupnea and the pattern of change of sigh frequency (FIG. 10). In only 8 of 24 animals were the patterns of sighing and eupneic responses similar.

Discussion

The brainstem has been recognized as the main site for the generation of rhythmic respiratory drive based on a long history of studies in intact, anesthetized and decerebrate animals (Lindsey et al. (2012) *Compr. Physiol.,* 2: 1619-1670; St. John (1990) *J. Appl. Physiol.,* 68: 1305-1315; St. John and Paton (2004) *Respir. Physiol. Neurobiol.* 143: 321-332) and more recently on experiments using neonatal in vitro preparations (Feldman and Del Negro (2006) *Nat. Rev. Neurosci.* 7: 232-242; Onimaru et al. (2006) J. Neurophysiol., 96: 55-61). The respiratory neurons are distributed in a number of different nuclei in the brainstem throughout the dorsal and ventral regions of the medulla and pons, and neurons within each nucleus make a unique and time dependent contribution to the generation of the pattern of respiratory activity. While not yet definitive, the cervical spinal cord may also contribute to respiratory rhythm generation, as spontaneous rhythmic breathing occurs in cervical spinalized dogs (Coglianese et al. (1997) *Respir. Physiol. Neurobiol.* 29: 247-254) and cats (Aoki et al. (1980) *Brain Res.* 202: 51-63). Further, in vitro studies have demonstrated the presence of inspiratory and pre-inspiratory neurons at the level of upper cervical spinal cord (Douse et al. (1992) *Exp. Brain Res.* 90: 153-162; Jones et al. (2012) *Respir. Physiol. Neurobiol.* 180: 305-310; Lipski and Duffin (1986) *Exp. Brain Res.* 61: 625-637; Oku et al. (2008) *Neuroreport,* 19: 1739-547 1743). However, in vitro studies, in artificial and reduced preparations do not fully recapitulate the physiological respiratory circuit for eupnea. The neural circuit generating and shaping eupnea is a large and complex network of interacting neurons that integrate multitude of afferent inputs and endogenously generated neural activity among multiple pontine, medullary and possibly spinal cervical locations. Therefore, we used epidural stimulation of the dorsal surface of the cervical spinal cord to assess the contribution of different cervical segments to respiratory neurogenesis in intact, anesthetized mice.

To our knowledge, this is the first study that examined respiratory function related to the cervical spinal cord in a whole mouse. Previous studies have used in vitro slice preparations or whole spinal cord/brain stem explants (Jones et al. (2012) *Respir. Physiol. Neurobiol.* 180: 305-310; Onimaru et al. (2006) *J. Neurophysiol.,* 96: 55-61). By utilizing epidural stimulation in the cervical spinal cord, we found that 1.5 mA stimulation at C3 evoked a significant respiratory change; 1.5 mA stimulation at C3 increased the respiratory frequency during epidural stimulation, and in many animals, respiratory frequency remained elevated after epidural stimulation ceased. These respiratory frequency responses were only seen when epidural stimulation was delivered at C3 and not at levels C0 through C2 or C4 and C5. In contrast, tidal volume did not change during or after epidural stimulation at C3 or any other cervical level tested. The number of sighs also increased during epidural stimulation at C3, and the increase in sigh frequency also persisted after epidural stimulation stopped, but the facilitation of post-stimulation sighing was less persistent than the post-stimulation facilitation of the eupneic rhythm. Finally, there were differences among the responses of individual animals, and there appeared to be a clustering of respiratory frequency responses that largely reflected the timing and durability of the change in respiratory frequency during and after epidural stimulation.

We discovered that 1.5 mA, 20 Hz epidural stimulation delivered at the level of C3 significantly increased the respiratory frequency, but not the tidal volume. The location of this responsive center at C3 appears to be caudal to the C2 segment that demarcated the caudal border of high cervical respiratory group as defined by optical signals from a brainstem-spinal cord preparation (Oku et al. (2008) *Neuroreport,* 19: 1739-547 1743). This may indicate that there are heretofore unrecognized elements of the respiratory CPG caudal to C2, or there may be unique electrophysiological properties at C3 that allow current administered at C3 to influence more rostral respiratory CPG function without the C3 region possessing CPG activity of its own. If the response to stimulation at C3 were derived from current spread to C2 and more rostral elements, we might have expected direct stimulation of C1 and C2 to have a larger effect on respiratory frequency, and we found no effect of epidural stimulation at these spinal levels at all or the stimulation was fatal to the mouse.

The spinal cord is segmentally organized, and there is a tendency to focus on the repetitive, similarity of each spinal segment. The unique susceptibility of the C3 level to modulation by epidural stimulation suggests that there are specific, non-segmentally repeated elements at C3 that contribute to or are part of the neural systems that generate eupnea and sighing.

One unique feature of the C3 locus is that it is a site of integration of sensory information particularly related to the spinal trigeminal nucleus (STN) (2, 24). At the level of the medulla, STN, hypoglossal nucleus, and pre-Botzinger complex are all reasonably close together and possess well-established reciprocal connections (Feldman and Del Negro (2006) *Nat. Rev. Neurosci.* 7: 232-242). It is possible that stimulation of C3 activates the afferent sensory fibers of STN which then influence the respiratory rhythm. There may be other tracts that are activated by C3 stimulation (e.g., medial longitudinal fasciculus) that integrate and coordinate the activity of brainstem nuclei. Although it is interesting that any rostrally projecting axons of passage might have been affected by epidural stimulation, there was no increase in respiratory activity when the C1 and C2 levels were stimulated, which argues against simple activation of rostrally projecting axons of passage. Thus, elucidating the mechanism(s) of respiratory responses to epidural stimulation at C3 and determining what unique features of C3 generate this response will require further studies.

The mechanism of modulation of the cervical respiratory network is likely through the interneuronal cervical respiratory circuit rather than direct phrenic motor neuron activation as there was no tonic respiratory muscle contraction during eupnea during epidural stimulation, but rather an increase in respiratory frequency. We performed a cluster analysis of the patterns of respiratory sigh activity. The cluster analysis of pre-, intra-, and post-stimulation conditions and sigh data also support the proposed mechanism of accessing the cervical interneuronal network rather than direct phrenic motor neuron activation as the frequency of sighing was also modulated, and sighs were present rather than unaffected or absent. The increase in sigh frequency during C3 stimulation (FIG. 8) along with clustering of respiratory patterns (FIG. 9) support the idea that the C3-brainstem respiratory circuit is connected and integrated with the ponto-medullary respiratory CPG since epidural stimulation affected the frequency of eupnea and the frequency of sighs, both of which have the CPGs within the brainstem. Moreover, the pattern of responses to epidural stimulation of eupnea and sighing were not correlated in individual animals. It seems unlikely that complete and separate CPGs for sighing and eupnea would be represented in the cervical spine, and so the dual effect of epidural stimulation strongly favors the hypothesis that cervical spinal neurons are part of an extended set of respiratory CPGs throughout the brainstem and upper cervical spine that support both sighing and eupnea. That two forms of respiratory activity were modified by epidural stimulation at C3 also makes it unlikely that the respiratory responses arose from a direct effect on motor neurons, which would have been expected to modify the duration or intensity of inspiratory and/or expiratory muscle activity, which we did not see.

Sighing has been associated with the retrotrapezoid nucleus/parafacial respiratory group (RTN/pFRG) and projects to preBotC (Onimaru et al. (2009) *Resp. Physiol. Neurobiol.,* 168: 13-18), while eupnea is related to a complex interaction of brainstem respiratory nuclei (Lindsey et al. (2012) *Compr. Physiol.,* 2: 1619-1670; St. John (1988) *Prog. Neurobiol.* 56: 97-117). Stimulation of a topographically distinct location in the cervical spine with associated alterations in both eupneic and sighing frequency and respiratory pattern suggests a reciprocally connected circuit between the respiratory centers for sighing and eupnea and the spinal cord and brainstem. The data gathered here are consistent with a hierarchical model of independent CPGs related to respiratory function in which the C3 region is a node or nexus of access to the respiratory circuit.

Interestingly, we discovered that there is an impact of stimulation on respiratory frequency that persists after removal of the stimulation. Such an observation supports the theory that spinal cord stimulation activates the cervical spinal motor circuit and lowers the threshold of activation or resting membrane potential for motor tasks with persistent and residual effects (Lu et al. (2016) *Neurorehab. Neural Repair.,* 1545968316644344). One might imagine that the increased respiratory frequency occurs by facilitation or disinhibition or both. In favor of facilitation, it is noteworthy that a sustained increase in respiratory frequency, termed long term facilitation, follows intermittent hypoxia (8), and this long term facilitation seemed to depend on serotonergically induced plasticity. The epidural stimulation is clearly different from intermittent hypoxia, but epidural stimulation seemed to induce a similarly sustained increase in respiratory frequency in many of the animals, and serotonin has been used to enhance respiratory and motor function after spinal cord injury through a mechanism of increased spinal excitability and state permissive for motor activation (Choi et al. 92005) *J. Neurosci.* 25: 4550-4559; Courtine et al. (2009) *Nat. Neurosci.* 12: 1333-1342; Fong et al. (2005) *J. Neurosci.* 25: 11738-11747).

Disinhibition is also a possible mechanism of increasing the frequency of eupnea and gasping, and there are many GABAergic interneurons at each segmental level of the spine, which may have been modulated by epidural stimulation so as to allow a sustained increase in respiratory frequency. Moreover, there are examples of increased respiratory activity following spinal injury that have been attributed to disinhibition of these spinal interneurons (Lane et al. (2009) *Respir. Physiol. Neurobiol.,* 169: 123-132). Defining the roles of facilitation and disinhibition (or both) in the response to epidural stimulation will also require further studies.

Summary.

We found that epidural stimulation of the dorsal spinal cord at the C3 level increased the frequency of eupnea and sighing. Stimulation at no other cervical level from the caudal medulla to C5 had any effect on either eupnea or sighing. For both eupnea and sighing, the increase in frequency persisted after epidural stimulation ceased in many animals. The duration of post-stimulation frequency facilitation was greater for eupnea than sighing. These findings suggest that spinal elements at the C3 level make a unique and heretofore unappreciated contribution to respiratory frequency generation for both eupnea and sighing, probably through an interaction with or participation in the CPGs for eupnea and sighing. The mechanisms of the responses to epidural stimulation merit further study to elucidate the therapeutic potential of cervical epidural stimulation in individuals with spinal cord injuries.

Example 3

Intraoperative Stimulation of Humans

FIG. 12 shows an overview of spinal respiratory stimulation. Anesthetized mice were monitored by pneumotach and EMG to monitor the respiratory rate. The heat map color code shown in FIG. 12 reflects an increase (yellow) or decrease (blue) in respiratory rate. Measures are normalized to a 2-3 minute baseline. The mA scale reflects stimuli of increasing intensity from 0.3 to 1.5 mA. In the sham and post-sham conditions, very little change in respiration was observed. During stimulation, however, we observed substantial increases in respiratory rate when stimulating between 1 and 1.5 mA, notably at cervical levels, C2, C3 and C4. Post-stimulation, we saw continued modulation that persisted for 3 minutes. These results suggest that intermittent stimulation may be beneficial and stimulation duty cycle reduction s may be possible.

FIG. 13 shows a summary of cervical respiratory stimulation in a mouse subjected to 30 Hz stimulation. Here the values for 1, 1.2, and 1.5 mA stimulation experiments are averaged. Prior to stimulation, in the sham and post-sham periods, very little change in respiration rate was seen. Substantial increases in respiratory rate were seen in stim and post-stim conditions, most notable at C3. (n=24).

FIG. 14 shows that stimulation at a frequency of 30 Hz at C3/4 can induce respiration during deep anesthesia in humans. Electrical stimulation of the dorsal cord at C3/4 resulted in diaphragm EMG bursts and productive inhalation. As in FIG. 17 (described below), this result indicates that the spinal cord stimulation can generate physiological respiratory/lung function.

FIG. 15 shows that stimulation at a frequency of 30 Hz at C3/4 can induce coordinated respiration during off-state in humans. This important experiment demonstrates that coordinated respiration can occur when stimulating the spinal cord. Note laryngeal and hypoglossal tone increasing prior to two breaths (*). This observation indicates that accessible regions of the spinal cord can allow for coordinated respiratory/lung function following dysfunction or loss of connectivity with brainstem respiratory centers.

FIG. 16 shows a representative respiratory response to stimulation at a frequency of 30 Hz at C3/4 in humans. Diaphragm EMG and ventilator pressure were monitored under light sedation with spontaneous breathing (ON State). Top PRE condition shows no response at 5 Hz or 30 Hz. During STIM, 5 Hz has no response, while 30 Hz increased the rate. Following stimulation, POST, the rate was unaffected in 5 Hz, but appeared to slow after 30 Hz stimulation.

FIG. 17 shows responses to spinal stimulation during deep anesthesia in humans. Patients were studied while spontaneous respiration was absent. Black dots represent individual experiments during stimulation (Intra-Stim), while the gray dots reflect individual experiments post-stimulation. At 5 Hz stimulation, no change in tidal volume or respiratory rate was observed at levels C2-C7. At 30 Hz stimulation, small changes in tidal volume were observed and more substantial increases in respiratory rate were observed. At 90 Hz, substantial increases in tidal volume were observed at C3/4 and increases in rate were observed at C3/4 and C6.

FIG. 18 shows responses to spinal stimulation during light anesthesia in humans. Patients were studied while spontaneous respiration was present. Black dots represent individual experiments during stimulation (Intra-Stim), while the gray dots reflect individual experiments post-stimulation. At 5 Hz stimulation, varying increases and decreases in tidal volume or respiratory rate were observed, normalized to pre-stimulation baseline. At 30 Hz stimulation, variable changes tidal volume and respiratory rate were observed. These results indicate that the cord may be more responsive to stimulation in the absence of anesthesia. Furthermore, it appears the tidal volume stimulation is short-lived.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of improving, and/or regulating, and/or restoring respiration in a subject with a respiratory deficiency, said method comprising:

administering, via at least one electrode placed on a dorsal spinal cord of the subject, epidural stimulation to the dorsal spinal cord using a stimulation selected to cause neuromodulation of interneurons of the dorsal spinal cord to generate a respiratory rhythm caused by a firing pattern of a respiratory central pattern generation (CPG), wherein the respiratory rhythm is caused by an activated respiratory drive of the subject;

receiving at least one of an $O_2$ saturation, an end tidal $CO_2$, a heart rate, and a tidal volume of the subject using one or more sensors; and adjusting at least one of a pulse amplitude, a pulse-width, a pulse frequency, and a duty cycle of said epidural stimulation based on the at least one of the $O_2$ saturation, the end tidal $CO_2$, the heart rate, and the tidal volume to provide a desired tidal volume, $O_2$ saturation, and end tidal $CO_2$.

2. The method of claim 1, wherein:

a stimulation pattern is altered in response to respiration rate and/or tidal volume; and/or said stimulation pattern is altered in response to heart rate.

3. The method of claim 1, wherein said respiratory deficiency is due to a spinal cord injury.

4. The method of claim 3, wherein said spinal cord injury is clinically classified as motor complete.

5. The method of claim 3, wherein said spinal cord injury is clinically classified as motor incomplete.

6. The method of claim 1, wherein:

said respiratory deficiency is due to a neurodegenerative disorder; or said respiratory deficiency is due to an ischemic brain injury; or said subject is at risk for sudden infant death syndrome (SIDS); or said subject is in intensive care unit patient with decreased respiratory drive; or said respiratory deficiency is acute respiratory distress syndrome (ARDS), or acute respiratory failure; or said respiratory deficiency is due to alcohol intoxication and/or a drug overdose; or said respiratory deficiency is due to a drug overdose.

7. The method of claim 1, wherein said method further comprises administering at least one monoaminergic agonist to said subject.

8. A stimulator configured to induce epidural in a cervical region of a subject according to claim 1.

9. The method of claim 1, wherein said neuromodulating utilizes:

a stimulator configured to induce epidural stimulation in a cervical region of a subject at a frequency and amplitude that improves, and/or regulates, and/or restores respiration in a subject with a respiratory deficiency; and one or more sensor selected from the group consisting of a sensor that detects chest wall movement and/or expansion.

10. The method of claim 9, wherein:

said stimulator is configured to induce epidural stimulation of a cervical spinal cord.

11. The method of claim 9, wherein:

said stimulator is coupled to a sensor that detects chest wall movement and/or expansion.

12. The method of claim 9, wherein feedback is provided to the stimulator from sensors assessing chest wall movement, and/or $O_2$ saturation, and/or end tidal $CO_2$ and uses this information to adjust stimulation parameters.

13. A method of removing a subject from a respirator, said method comprising:

inducing or maintaining respiration is a subject using a method of claim 1 while said subject is removed from the respirator (ventilator) and/or after said subject is removed from said respirator.

14. The method of claim 1, wherein there is no tonic respiratory muscle contraction during inspiration and expiration phases of breathing in said subject during neuromodulation of a cervical spinal cord.

* * * * *